(12) United States Patent  (10) Patent No.: US 9,345,740 B2
Kim  (45) Date of Patent: May 24, 2016

(54) IAP ANTAGONISTS

(71) Applicant: BRISTOL-MYERS SQUIBB COMPANY, Princeton, NJ (US)

(72) Inventor: Kyoung S. Kim, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/413,791

(22) PCT Filed: Jul. 10, 2013

(86) PCT No.: PCT/US2013/049828
§ 371 (c)(1),
(2) Date: Jan. 9, 2015

(87) PCT Pub. No.: WO2014/011712
PCT Pub. Date: Jan. 16, 2014

(65) Prior Publication Data
US 2015/0164974 A1   Jun. 18, 2015

Related U.S. Application Data

(60) Provisional application No. 61/669,698, filed on Jul. 10, 2012.

(51) Int. Cl.
*A61K 38/00* (2006.01)
*A61P 35/00* (2006.01)
*A61K 38/06* (2006.01)
*C07F 7/08* (2006.01)
*A61K 45/06* (2006.01)
*C07K 5/083* (2006.01)

(52) U.S. Cl.
CPC .............. *A61K 38/06* (2013.01); *A61K 45/06* (2013.01); *C07F 7/0812* (2013.01); *C07K 5/0806* (2013.01)

(58) Field of Classification Search
CPC ........ A61K 38/00; A61K 38/03; A61K 38/55
See application file for complete search history.

(56) References Cited

FOREIGN PATENT DOCUMENTS

WO   WO 2009/020589   2/2009

*Primary Examiner* — James H Alstrum Acevedo
*Assistant Examiner* — Kaipeen Yang
(74) *Attorney, Agent, or Firm* — Elliott Korsen

(57) ABSTRACT

There are disclosed compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

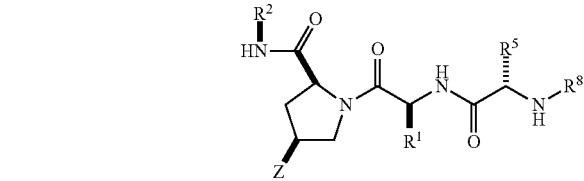

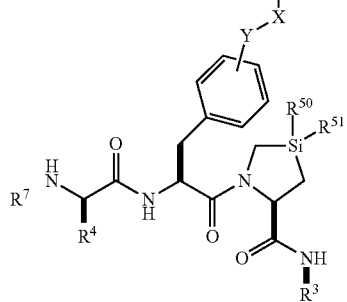

(II)

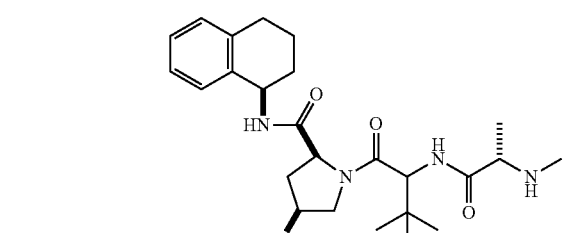

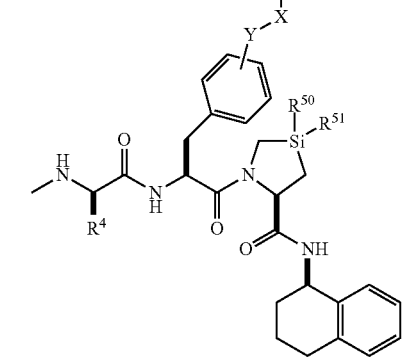

(IV)

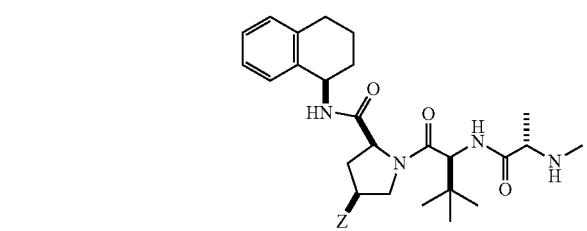

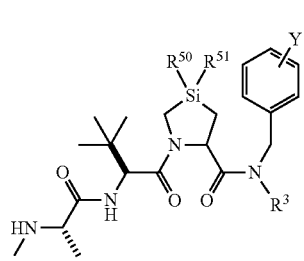

7 Claims, No Drawings

IAP ANTAGONISTS

FIELD OF THE INVENTION

The invention relates generally to compounds that modulate the activity of inhibitors of apoptosis (IAPB), pharmaceutical compositions containing said compounds and methods of treating proliferative disorders and disorders of dysregulated apoptosis, such as cancer, utilizing the compounds of the invention.

BACKGROUND OF THE INVENTION

Apoptosis or programmed cell death is a genetically and biochemically regulated mechanism that plays an important role in development and homeostasis in invertebrates as well as vertebrates.

Aberrancies in apoptosis that lead to premature cell death have been linked to a variety of developmental disorders. Deficiencies in apoptosis that result in the lack of cell death have been linked to cancer and chronic viral infections.

Caspases are cysteine-containing aspartate specific proteases that play a key role in effecting apoptosis. Once activated from their inactive zymogen form by proteolytic processing, caspases digest vital cell proteins from within the cell. Since caspases are such strong proteases, tight control of this family of proteins is necessary to prevent premature cell death. In addition to proteolytic processing, caspases are also regulated by a family of molecules known as Inhibitors of Apoptosis Proteins (IAP). IAPB are naturally occurring intracellular proteins that suppress caspase-dependent apoptosis. SMAC, an intracellular protein also known as DIABLO, functions to modulate the activity of IAPB. In normal healthy cells, SMAC and IAPB function together to maintain healthy cells. However, in certain disease states, e.g., cancers and other proliferative disorders, the activities of IAPB are not adequately modulated and therefore, prevent apoptosis and cause or exacerbate abnormal proliferation and survival.

IAP antagonists, also known as SMAC mimetics, are synthetic molecules that mimic the structure and IAP modulating activity of the four N-terminal amino acids of SMAC (AVPI). When administered to a subject suffering proliferative disorders, the compounds antagonize IAP activities causing an increase in apoptosis among abnormally proliferating cells.

IAPB are found in all organisms ranging from *Drosophila* to human and are known to be overexpressed in many human cancers. IAPB comprise one to three Baculovirus IAP repeat (BIR) domains. The BIR domain is a zinc binding domain of about 70 residues comprising 4 alpha-helices and 3 beta strands, with cysteine and histidine residues that coordinate the zinc ion. The BIR 2 and 3 domains contain a conserved inhibitor of apoptosis binding motif (IBM) capable of binding caspases—and inhibiting their proteolytic activity.

As an example, human X-chromosome linked IAP (XIAP) inhibits the executioner caspases-3, and -7 as well as the Apaf-1-cytochrome C mediated activation of the initiator caspase-9. Caspases-3 and -7 are inhibited by the BIR2 domain of XIAP, while the BIR3 domain of XIAP is responsible for the inhibition of caspase-9 activation. XIAP is expressed ubiquitously in most adult and fetal tissues. Overexpression of XIAP in tumor cells has been demonstrated to confer protection of the tumor cells against a variety of pro-apoptotic stimuli and promotes resistance to chemotherapy. Consistent with this, a strong correlation between XIAP protein levels and survival has been demonstrated for patients with acute myelogenous leukemia.

Other BIR2-3 containing IAP family members, while capable of binding caspases, do not directly inhibit their proteolytic activity. Rather they inhibit apoptosis by affecting signaling activities of key proteins in cell survival pathways. Like XIAP, these IAPB possess a carboxyl-terminal RING finger domain capable of conjugating ubiquitin to specific protein substrates. As an example, cellular IAPB 1 and 2 (cIAP1/2), ubiquitinate RIPK, a signaling intermediate of tumor necrosis death receptor (TNF-DR) activation. Ubiquitinated RIPK is unable to activate caspase-8 in the context of DR activation by TNF family DR ligands. On the contrary, the long ubiquitin chains attached to RIPK provide a scaffold by which cell components of the NFκB cell survival signaling cascade can attach and become activated.

In normal cells undergoing apoptosis, the IAP-mediated inhibition is removed by the mitochondrial protein SMAC (second mitochondrial activator of caspases; also known as DIABLO). SMAC is synthesized as a precursor molecule of 239 amino acids; the N-terminal 55 residues serving as the mitochondria targeting sequence that is removed after import. The mature form of SMAC resides in the inter-membrane space of mitochondria. At the time of apoptosis induction, SMAC is released from mitochondria into the cytosol where, together with cytochrome c, it binds to XIAP, and eliminates its inhibitory effect on caspases. SMAC also binds cIAP1/2 and inhibits their ability to ubiquitinate RIPK. SMAC interacts with essentially all IAPB that have been examined to date and thus appears to be a master regulator of apoptosis in mammals.

Down-regulation of XIAP expression by antisense oligonucleotides has been shown to sensitize tumor cells to death induced by a wide range of pro-apoptotic agents, both in vitro and in vivo. SMAC/DIABLO-derived peptides have also been demonstrated to sensitize a number of different tumor induced select cell lines to undergo apoptosis as single agents, while other cell lines require an additional stimulus such as DR agonists or co-treatment with pro-apoptotic drugs. Because IAP inhibition appears to be a viable mechanism for promoting apoptosis and treating diseases and conditions that are sensitive to apoptosis, there is a continuing need to develop compounds that can inhibit IAP.

SUMMARY OF THE INVENTION

The present invention provides compounds, methods of modulating the activity of IAP, and methods for treating various medical conditions using said compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in the treatment and/or prophylaxis of multiple diseases or disorders associated with IAP inhibition, such as cancer and other maladies.

The compounds of the invention may be used in therapy.

The compounds of the invention may be used for the manufacture of a medicament for the treatment and/or prophylaxis of multiple diseases or disorders associated with IAP inhibition.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention wherein:

X is —(CR$^{16}$R$^{17}$)$_m$,

[structures shown]

or X is absent;

Y and Z are independently —O—, C=O, NR$^6$ or are absent;

R$^1$ is optionally substituted alkyl, optionally substituted cycloalkyl, optionally substituted alkylaryl or optionally substituted aryl;

R$^2$ and R$^3$ are independently optionally substituted alkyl, optionally substituted cycloalkyl, optionally substituted cycloalkylalkyl, optionally substituted arylalkyl or optionally substituted aryl;

R$^4$ and R$^5$ are independently optionally substituted alkyl or optionally substituted cycloalkyl;

R$^6$ is hydrogen or (C$_1$-C$_3$)alkyl;

R$^7$ and R$^8$ are independently hydrogen, optionally substituted alkyl or optionally substituted cycloalkyl;

R$^9$ and R$^{10}$ are independently hydrogen, optionally substituted alkyl, or R$^9$ and R$^{10}$ may be taken together to form a ring;

R$^{11}$ to R$^{14}$ are independently hydrogen, halogen, optionally substituted alkyl or OR$^{15}$;

R$^{15}$ is hydrogen, optionally substituted alkyl or optionally substituted cycloalkyl;

R$^{16}$ and R$^{17}$ are independently hydrogen, halogen or optionally substituted alkyl;

R$^{50}$ and R$^{51}$ are independently optionally substituted alkyl, or R$^{50}$ and R$^{51}$ are taken together to form a ring;

m and n are independently an integer from 0-4;

o and p are independently an integer from 0-3;

q is an integer from 0-4; and r is an integer from 0-1;

or a pharmaceutically acceptable salt, tautomer or stereoisomer thereof.

In a second aspect, the invention provides a compound of Formula (I) within the scope of the first aspect, wherein:

X is

[structures shown]

or X is absent;

R$^1$ is optionally substituted alkyl or optionally substituted alkylaryl;

R$^2$ and R$^3$ are independently optionally substituted alkyl, optionally substituted cycloalkyl, optionally substituted cycloalkylalkyl or optionally substituted arylalkyl;

R$^4$ and R$^5$ are independently optionally substituted alkyl;

R$^6$ is hydrogen or methyl;

R$^7$ and R$^8$ are independently hydrogen, optionally substituted alkyl or optionally substituted cycloalkyl;

or a pharmaceutically acceptable salt, tautomer or stereoisomer thereof.

In a third aspect, the invention provides a compound of Formula (I) within the scope of the first or second aspect, wherein:

R$^1$ is (C$_1$-C$_6$)alkyl;

R$^2$ and R$^3$ are independently alkyl, cycloalkyl, cycloalkylalkyl or phenylalkyl, wherein the phenyl group is substituted with one or more alkyl or halogen groups;

R$^4$ and R$^5$ are independently (C$_1$-C$_3$)alkyl;

R$^7$ and R$^8$ are independently (C$_1$-C$_3$)alkyl;

or a pharmaceutically acceptable salt, tautomer or stereoisomer thereof.

In a fourth aspect, the invention provides a compound of Formula (I) within the scope of the first, second or third aspect, wherein:

R$^1$ is t-butyl;

R$^2$ is 1,2,3,4-tetrahydronaphthalenyl;

R$^3$ is alkyl, cycloalkyl, cycloalkylalkyl or phenylalkyl, wherein the phenyl group is substituted with one or more fluoro groups;

R$^4$ and R$^5$ are independently methyl or ethyl;

R$^7$ and R$^8$ are independently methyl or ethyl;

R$^6$ is hydrogen;

R$^{50}$ and R$^{51}$ are independently methyl, ethyl or propyl;

or a pharmaceutically acceptable salt, tautomer or stereoisomer thereof.

In a fifth aspect, the invention provides a compound of Formula (II)

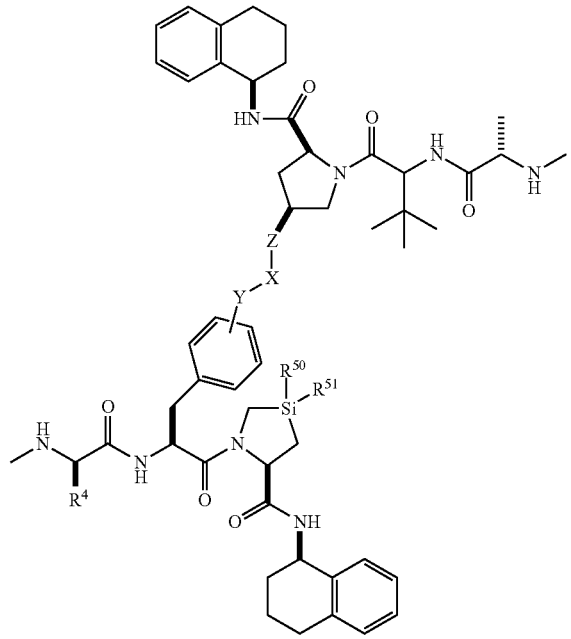

(II)

wherein:

X is —(CR$^{16}$R$^{17}$)$_m$,

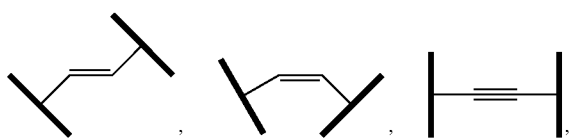

or X is absent;

Y and Z are independently —O—, C=O, NR$^6$ or are absent;

R$^4$ is optionally substituted alkyl or optionally substituted cycloalkyl;

R$^6$ is hydrogen or (C$_1$-C$_3$)alkyl;

R$^{50}$ and R$^{51}$ are independently methyl, ethyl or propyl;

or a pharmaceutically acceptable salt, tautomer or stereoisomer thereof.

In a sixth aspect, the invention provides a compound of Formula (III)

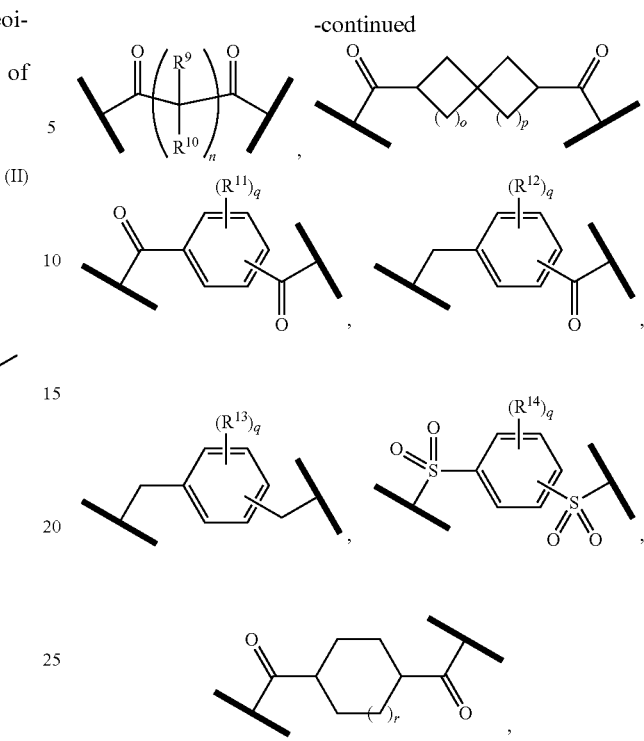

-continued

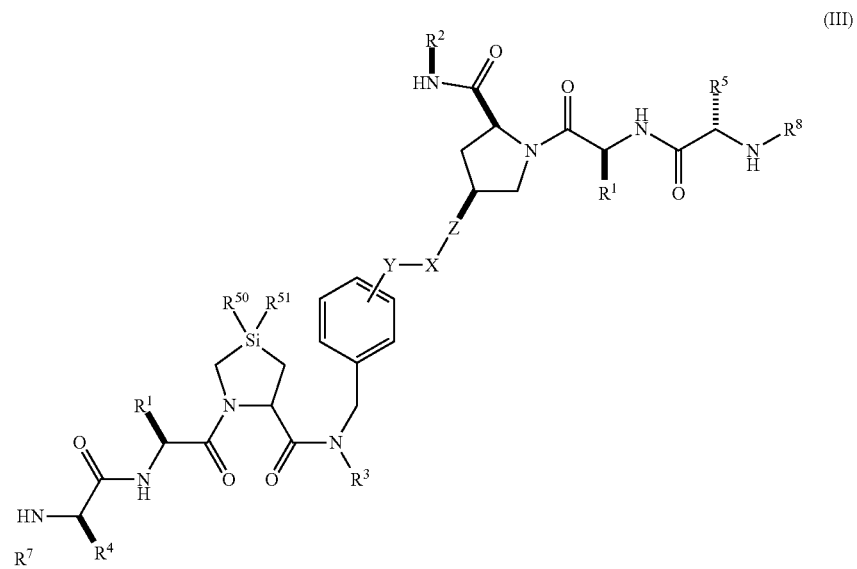

(III)

wherein:

X is —(CR$^{16}$R$^{17}$)$_m$,

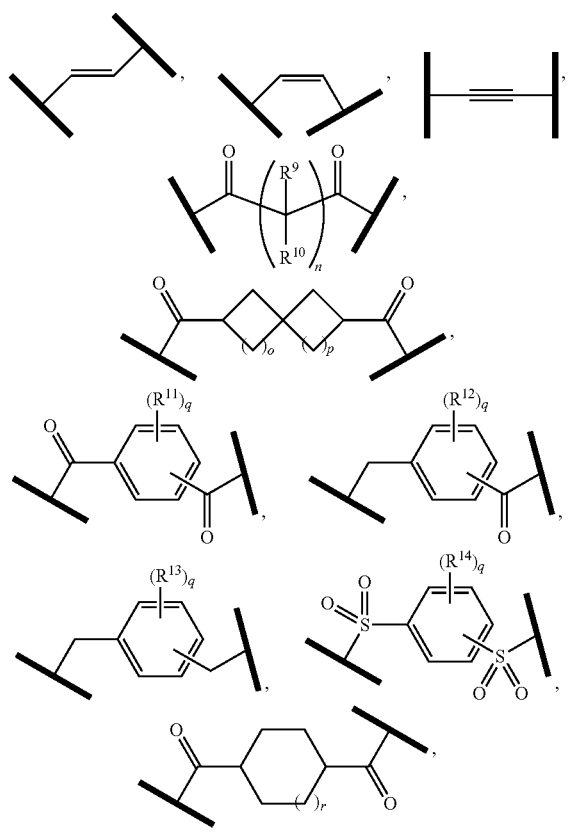

or X is absent;

Y and Z are independently —O—, C=O, NR$^6$ or are absent;

R$^1$ is optionally substituted alkyl, optionally substituted cycloalkyl, optionally substituted alkylaryl or optionally substituted aryl;

R$^2$ and R$^3$ are independently optionally substituted alkyl, optionally substituted cycloalkyl, optionally substituted cycloalkylalkyl, optionally substituted arylalkyl or optionally substituted aryl;

R$^4$ and R$^5$ are independently optionally substituted alkyl or optionally substituted cycloalkyl;

R$^6$ is hydrogen or (C$_1$-C$_3$)alkyl;

R$^7$ and R$^8$ are independently hydrogen, optionally substituted alkyl or optionally substituted cycloalkyl;

R$^9$ and R$^{10}$ are independently hydrogen, optionally substituted alkyl, or R$^9$ and R$^{10}$ may be taken together to form a ring;

R$^{11}$ to R$^{14}$ are independently hydrogen, halogen, optionally substituted alkyl or OR$^{15}$;

R$^{15}$ is hydrogen, optionally substituted alkyl or optionally substituted cycloalkyl;

R$^{16}$ and R$^{17}$ are independently hydrogen, halogen or optionally substituted alkyl;

R$^{50}$ and R$^{51}$ are independently optionally substituted alkyl, or R$^{50}$ and R$^{51}$ are taken together to form a ring;

m and n are independently an integer from 0-4;

o and p are independently an integer from 0-3;

q is an integer from 0-4; and r is an integer from 0-1;

or a pharmaceutically acceptable salt, tautomer or stereoisomer thereof.

In a seventh aspect, the invention provides a compound of Formula (IV)

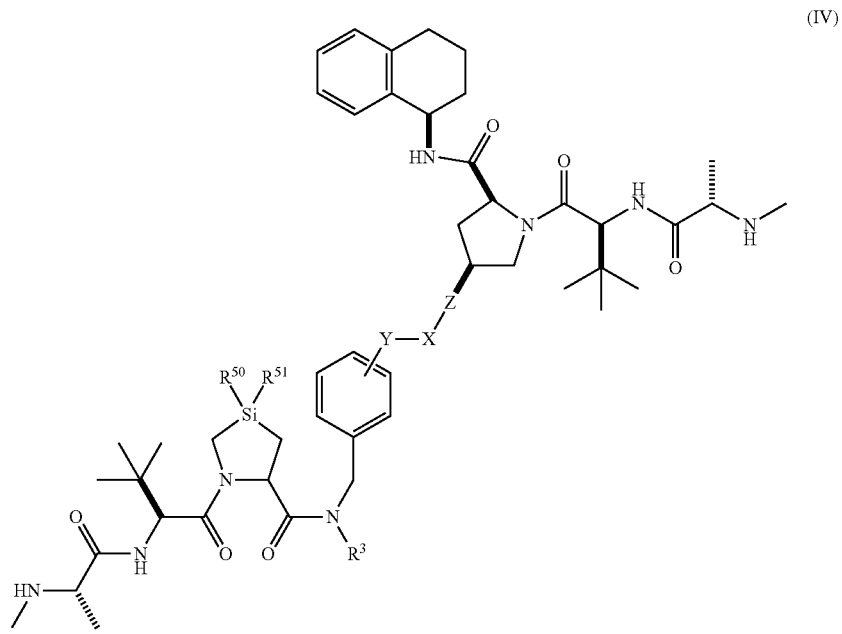

(IV)

wherein:

X is —(CR$^{16}$R$^{17}$)$_m$,

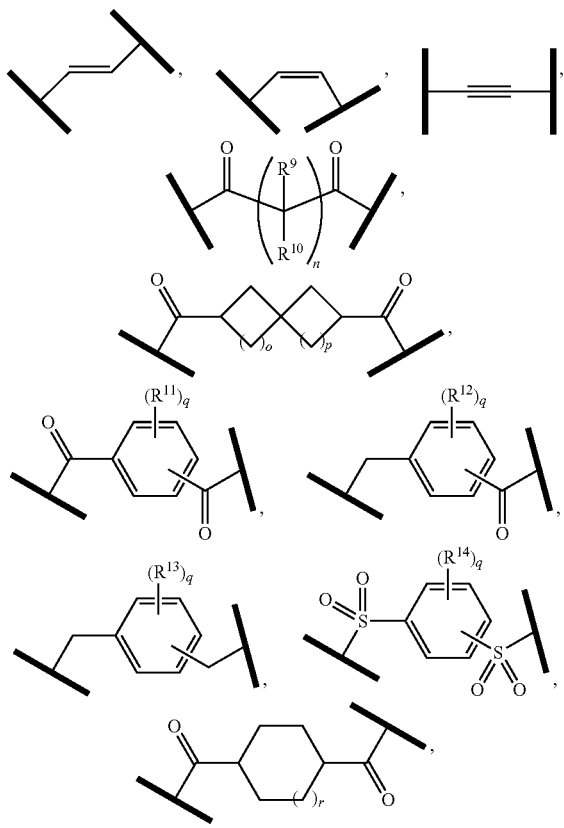

or X is absent;

Y and Z are independently —O—, C═O, NR$^6$ or are absent;

R$^3$ is optionally substituted alkyl, optionally substituted phenylalkyl, optionally substituted aryl or optionally substituted cycloalkyl;

R$^6$ is hydrogen or (C$_1$-C$_3$)alkyl;

R$^{50}$ and R$^{51}$ are independently methyl, ethyl or propyl;

or a pharmaceutically acceptable salt, tautomer or stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, R$^1$ is C$_1$-C$_6$alkyl;

In another embodiment, R$^1$ is t-butyl.

In another embodiment, R$^2$ and R$^3$ are independently cycloalkyl, or phenylalkyl, wherein the phenyl group is substituted with one or more alkyl or halogen groups.

In another embodiment, R$^2$ and R$^3$ are independently 1,2,3,4-tetrahydronaphthalenyl.

In another embodiment, the compounds of the invention have BIR3 IC$_{50}$ values≤0.20.

In another embodiment, the compounds of the invention have BIR3 IC$_{50}$ values≤0.07.

In another embodiment, the compounds of the invention have BIR3 IC$_{50}$ values≤0.02.

In another embodiment, the compounds of the invention have BIR3 IC$_{50}$ values≤0.005.

In another embodiment, the compounds of the invention have BIR2-3 IC$_{50}$ values≤0.40.

In another embodiment, the compounds of the invention have BIR2-3 IC$_{50}$ values≤0.10.

In another embodiment, the compounds of the invention have BIR2-3 IC$_{50}$ values≤0.010.

In another embodiment, the compounds of the invention have BIR2-3 IC$_{50}$ values≤0.005.

II. Other Embodiments of the Invention

In another embodiment, the present invention provides a composition comprising one or more compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with the inhibition of apoptosis.

In another aspect, the invention provides a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, the invention provides a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas, sarcomas including Kaposi's sarcoma, erythroblastoma, glioblastoma, meningioma, astrocytoma, melanoma, and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents; (iii) DNA-crosslinking agents; (iv) intercalating agents; (v) protein synthesis inhibitors; (vi) topoisomerase I poisons, such as camptothecin or topotecan; (vii) topoisomerase II poisons; (viii) microtubule-directed agents; (ix) kinase inhibitors; (x) miscellaneous investigational agents; (xi) hormones; and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

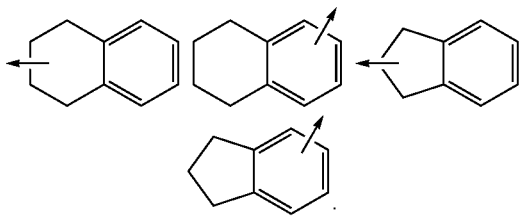

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heteroaryl" or "aromatic heterocyclic group" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As used herein, the term "heterocyclo", "heterocyclic" or "heterocyclyl" is intended to mean a 5-, 6- or 7-membered non-aromatic ring system containing from 1 to 4 heteroatoms selected from O, N or S. Examples of heterocycles include, but are not limited to, pyrrolidinyl, tetrahydrofuranyl, tetrahydropyranyl, piperidyl, pyrrolinyl, piperazinyl, imidazolinyl, morpholinyl, imidazolidinyl, pyrazolidinyl and pyrazolinyl.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWG include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl$)_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a di-substituted hydrazine, R4-M and R7-M, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "therapeutically effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

VI. Methods of Preparation

Compounds of the invention may be prepared according to the general routes illustrated in Schemes 1-9. Tautomers and solvates (e.g., hydrates) of the compounds are also within the scope of the present invention. Methods of solvation are generally known in the art. Accordingly, the compounds of the instant invention may be in the free or hydrate form, and may be obtained by methods exemplified by the following Schemes.

The substituents $R^{50}$ and $R^{51}$ as defined above are included as substituents on each of the silaproline derivatives shown in Schemes 1-9.

Dimeric silaproline derivative 25 can be prepared according to the synthetic route outlined in Scheme 1. Amide bond coupling of silaproline 1 (*Eur. J. Org. Chem.*, 807 (2000)) with a primary amine 2 ($R^3NH_2$) in the presence of standard coupling reagents, such as EDC and HOAt provides amide 3. Subsequent removal of the N-Boc protecting group with for example, TFA followed by coupling with phenylalanine derivative 5 affords the desired peptide 6. Removal of the N-Boc protecting group of 6 under acidic conditions (e.g., TFA) followed by coupling with amino acid 8 in the presence of a coupling reagent (e.g., HATU) provides peptide 9. Reduction of the nitro group of intermediate 9 using hydrogen and Pearlman's catalyst gave 10, which can then be coupled to 4-(methoxycarbonyl)benzoic acid (11) to afford peptide 12. Intermediate 13, derived from hydrolysis of ester 12 under basic conditions, can be coupled to pyrrolidine amine 14 using 4-(4,6-dimethoxy-1,3,5-triazin-2-yl)-4-methylmorpholinium chloride (DMT-MM) to give intermediate 15. Ester 15 can be hydrolyzed under basic conditions to give 16, which can be coupled to primary amine 17 ($R^2NH_2$) in the presence of standard coupling reagents, such as EDC and HOAt to afford amide 18. Hydrogenolysis of 18 led to pyrrolidine 19, which was coupled to N-Fmoc-protected amino acid 20. Removal of the Fmoc group of 21 with piperidine, followed by coupling of the requisite amine 22 with N-Boc amino acid 23 led to intermediate 24. Global deprotection of 24 under acidic conditions provides the desired analogues 25.

Scheme 1

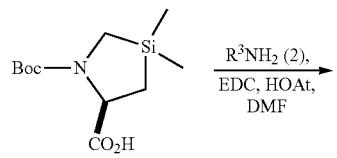

1

-continued
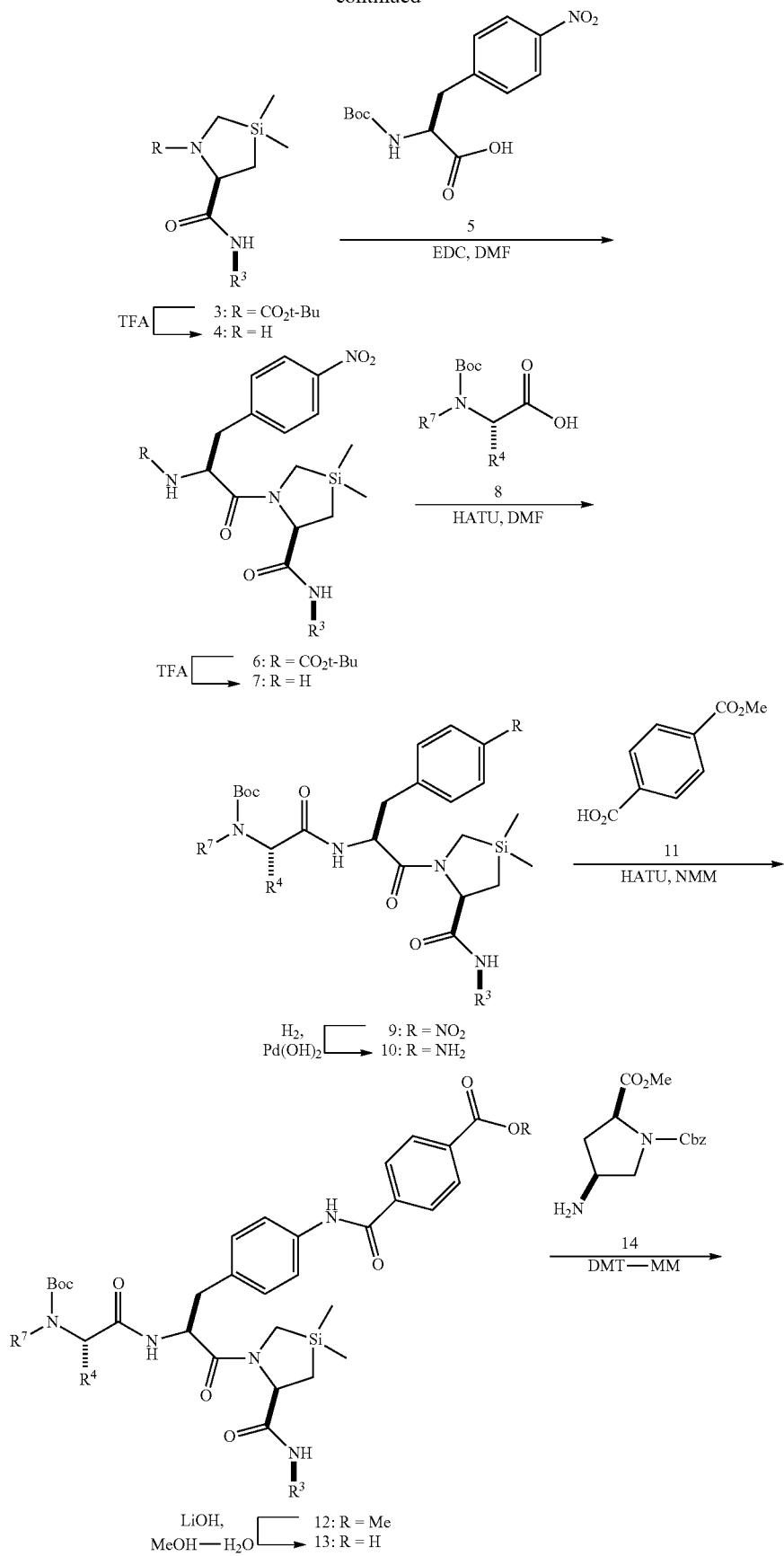

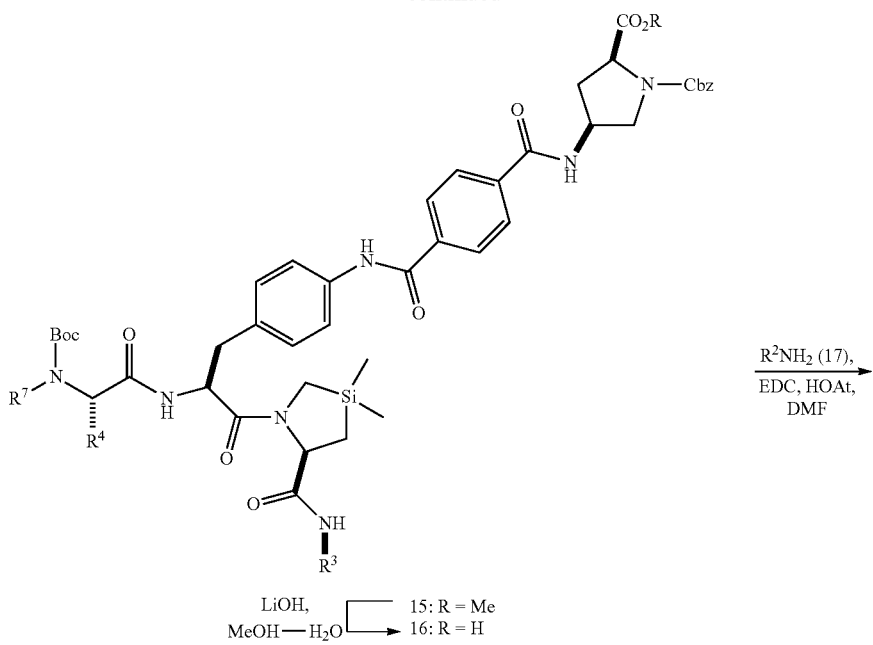
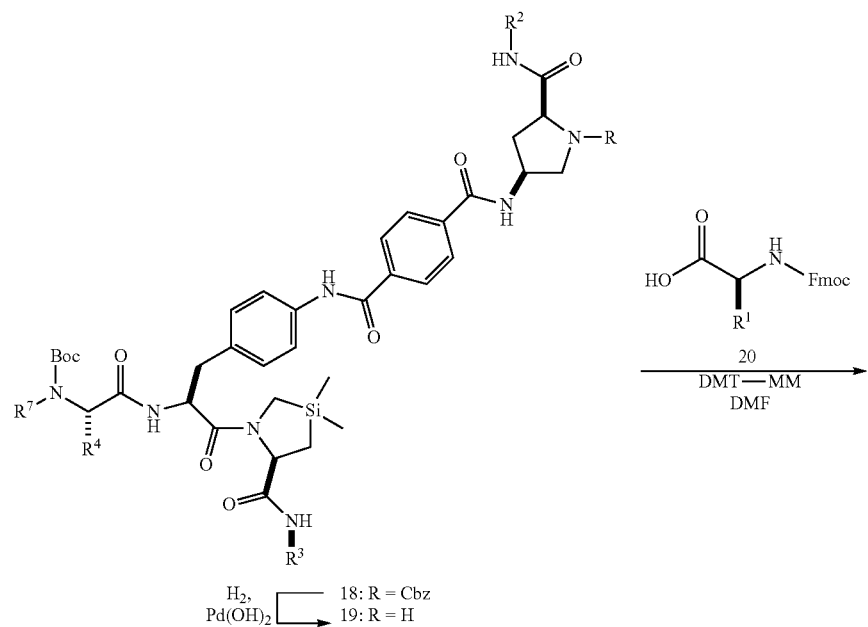

-continued

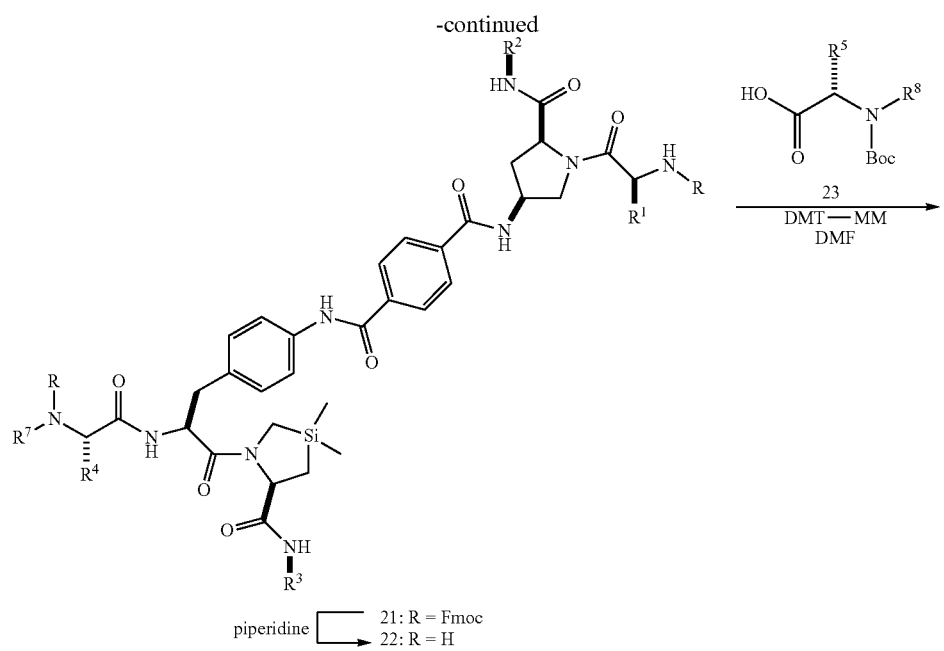

21: R = Fmoc
22: R = H
piperidine

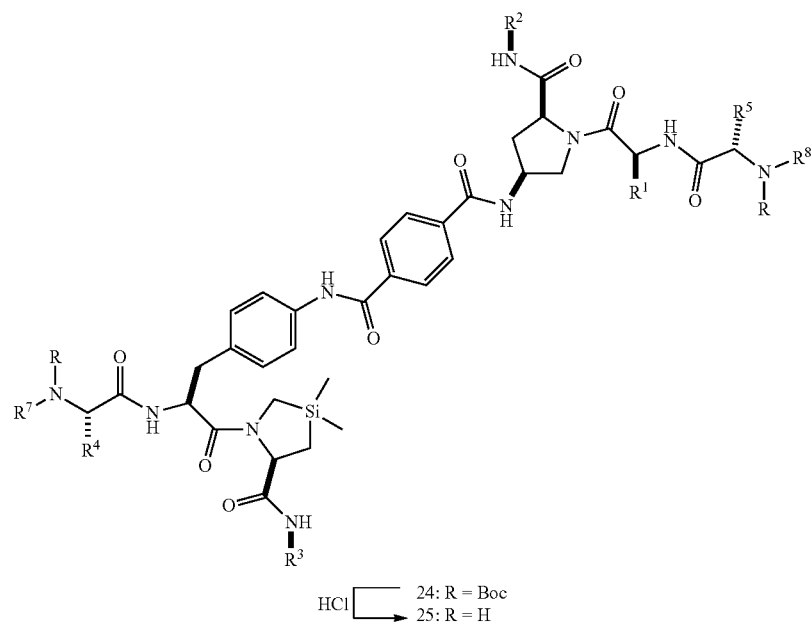

24: R = Boc
25: R = H
HCl

Urea analogues 34 can be prepared using the chemistry described in Scheme 2. Fmoc-protected aminoproline 26 can be converted to amide 28 by employing primary amines 27 and coupling reagents, such as EDC and HOAt. Removal of the N-Boc protecting group of 28 under acidic conditions, followed by coupling with the N-Boc amino acid 29 can furnish 30. Removal of the N-Boc group of intermediate 30, followed by coupling with N-Boc amino acid 31 led to tripeptide derivative 32. Removal of the N-Fmoc group of 32 with piperidine provided the key peptide intermediate 33. Synthesis of the heterodimeric analogues 34 can occur through a two-step procedure employing the carbamoyl chlorides derived from aniline derivative 10, followed by removal of the N-Boc moieties under acidic conditions (e.g., HCl).

Scheme 2

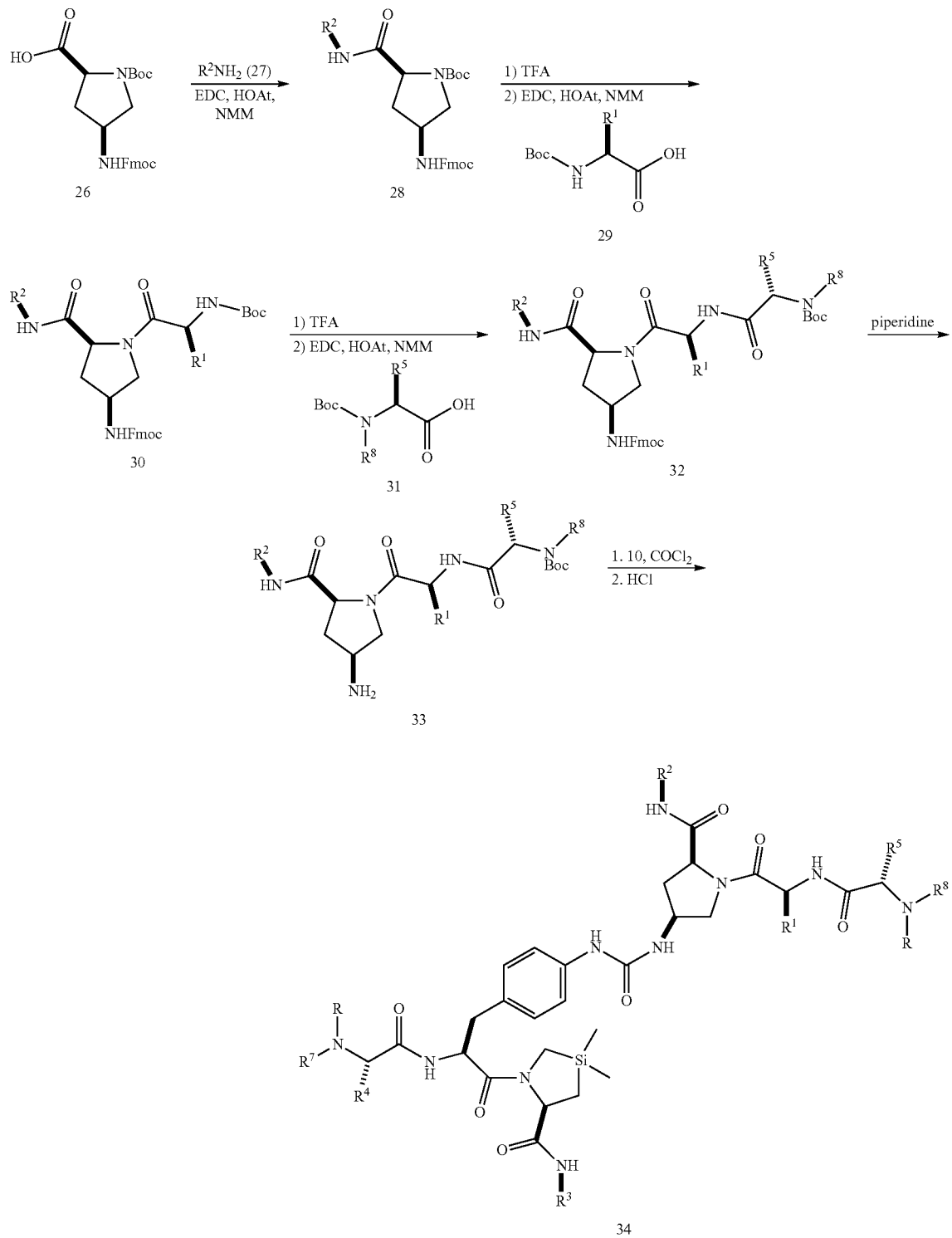

With the availability of intermediate 33, analogues 25 can be prepared using the alternative route outlined in Scheme 3. Coupling of silaproline derivative 4 to the Fmoc amino acid 35 using for example, DMT-MM can furnish dipeptide 36. Hydrolysis of the t-butyl ester 36 under acidic conditions, followed by coupling with the key peptide intermediate 33 in the presence of HATU can provide dimer 38. Removal of the N-Fmoc group of intermediate 38 with piperidine followed by coupling of the requisite amine 39 with N-Boc amino acid 8 led to peptide 24. Global deprotection of 24 under acidic conditions affords the desired analogues 25.

Scheme 3
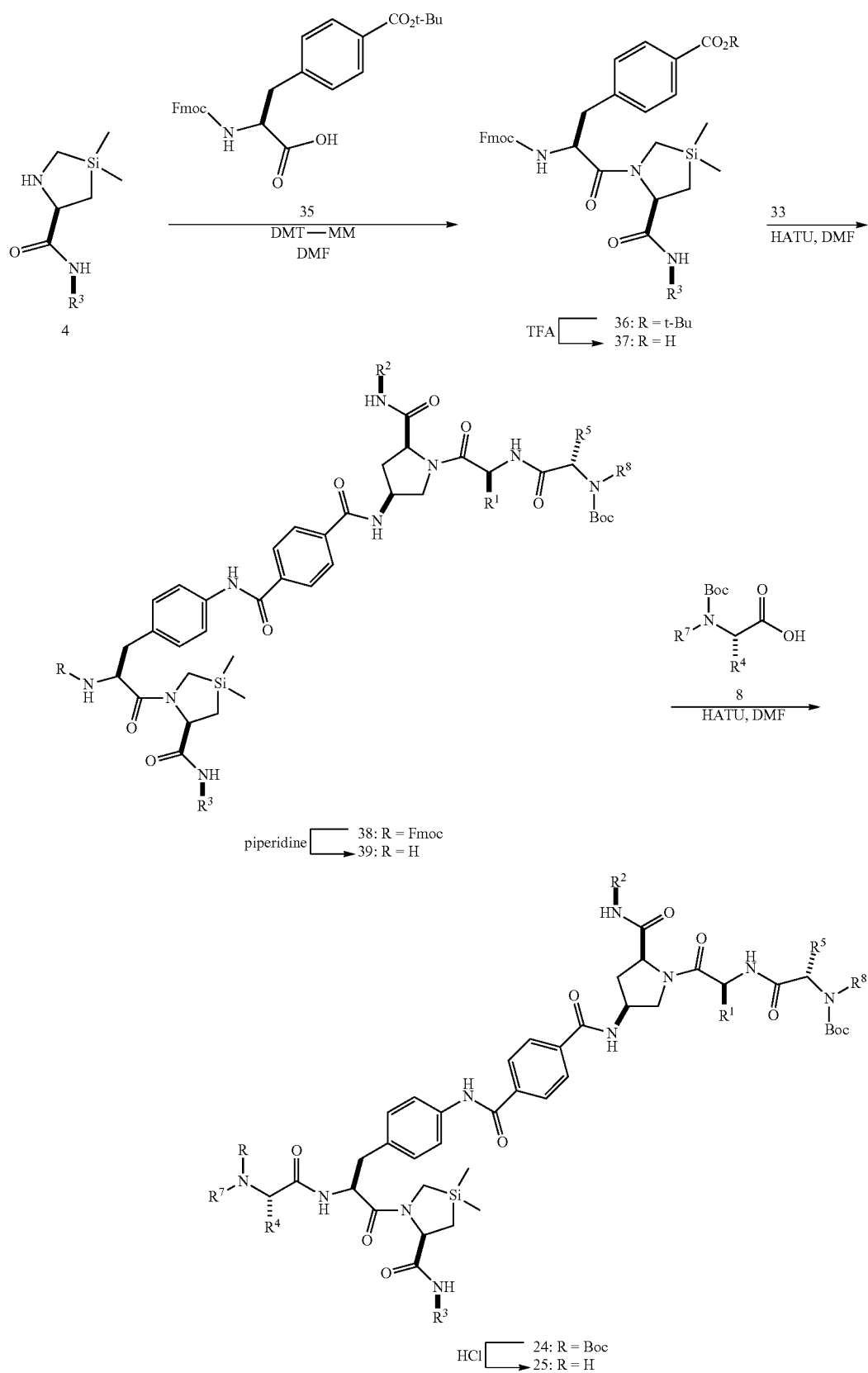

Heterodimeric ether analogues 50 can be prepared using the synthetic route outlined in Scheme 4. Deprotonation of the hydroxyproline derivative 40 with sodium hydride followed treatment with methyl 4-(bromomethyl)benzoate (41) affords the benzyl ether derivative 42. Following the same iterative steps of N-Boc deprotection and standard amide bond coupling as described above led to intermediate 47. Base-promoted hydrolysis of the ester 47 followed by coupling of the intermediate carboxylic acid 48 with aniline 10 in the presence of a coupling reagent (e.g., DMT-MM) furnished the dimer 49. Removal of the N-Boc groups of 49 provided the desired analogues 50.

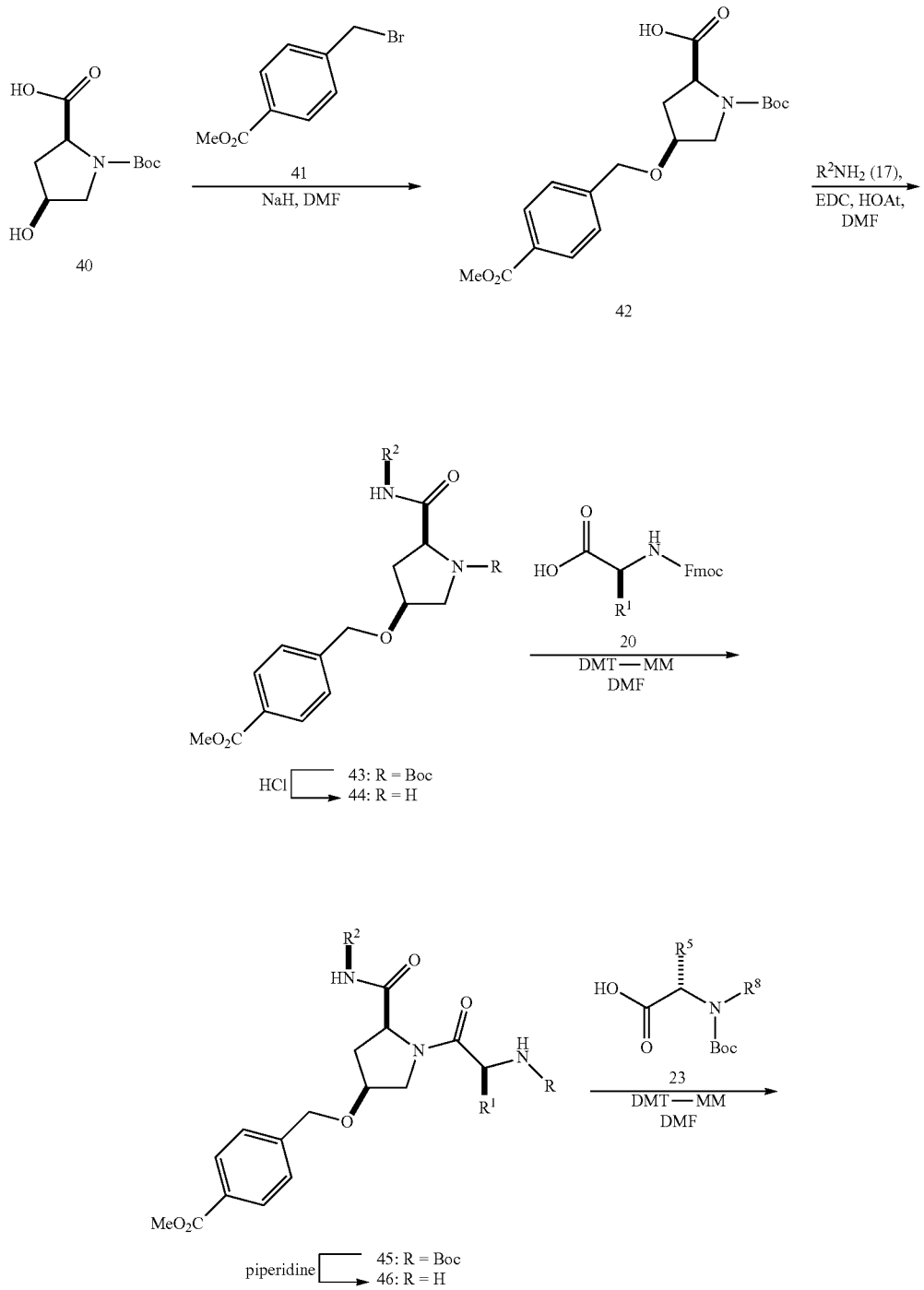

Scheme 4

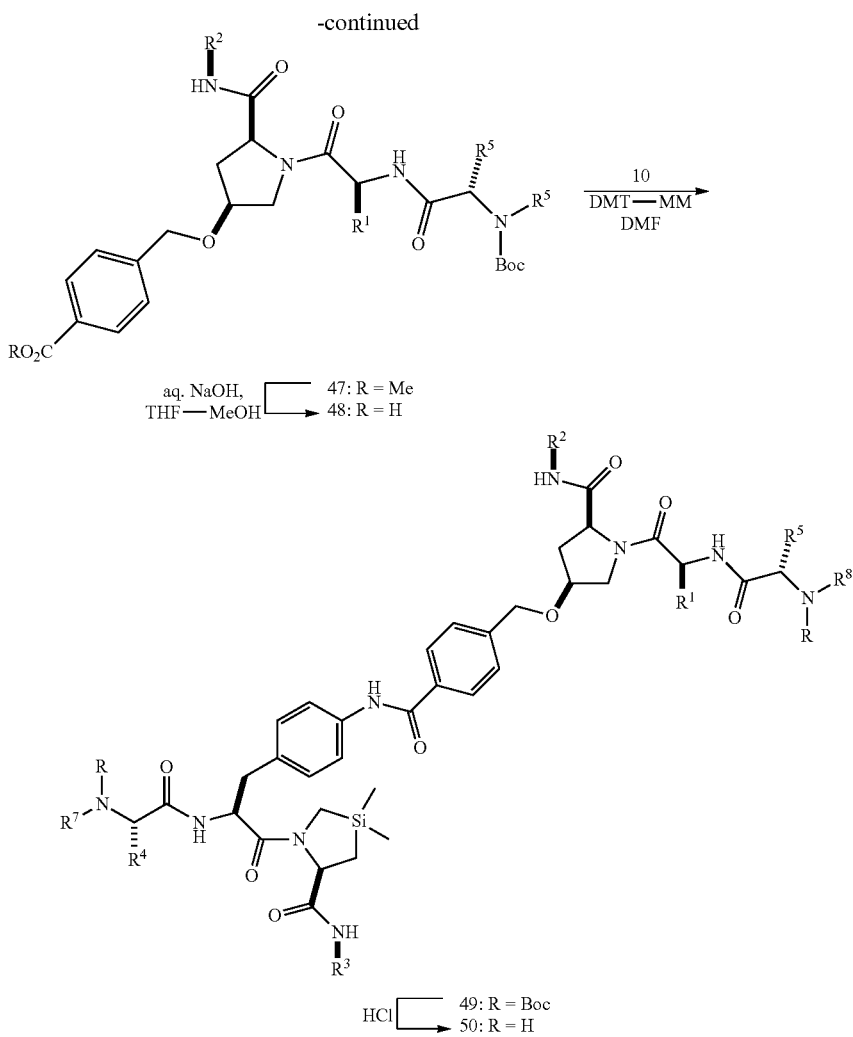

47: R = Me
48: R = H
(aq. NaOH, THF—MeOH)

49: R = Boc
50: R = H
(HCl)

The acetylene-based heterodimeric analogues 59 can be prepared using the synthetic route outlined in Scheme 5. Iodophenylalanine derivative 52, derived from silaproline derivative 4 and amino acid 51, can be coupled to methyl 4-ethynylbenzoate (53) to afford intermediate 54. Removal of the N-Boc group of 54 with HCl, followed by coupling with amino acid 8, using standard amide bond forming conditions led to intermediate 56. Hydrolysis of ester 56 under basic conditions, followed by coupling of intermediate acid 57 with tetrapeptide 33 gave heterodimer 58. Global deprotection of 58 under acidic conditions affords the desired analogues 59.

Scheme 5

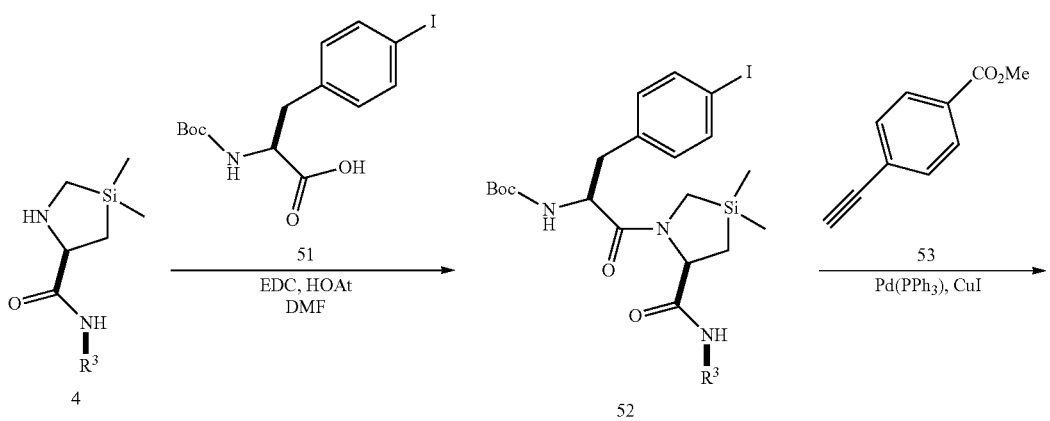

-continued
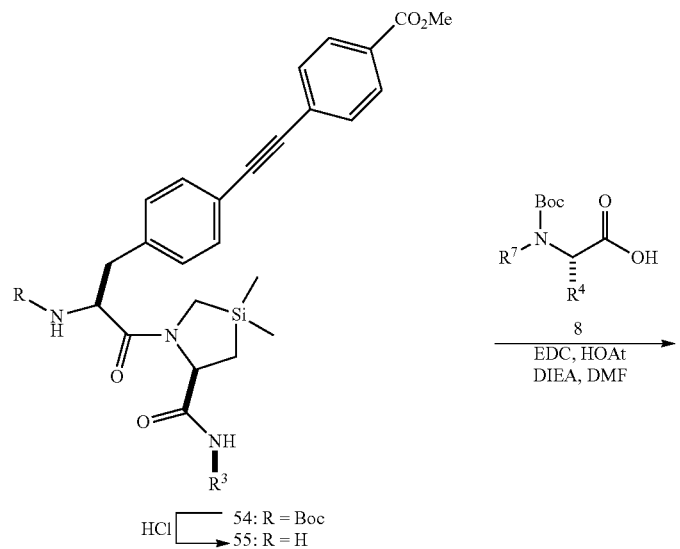
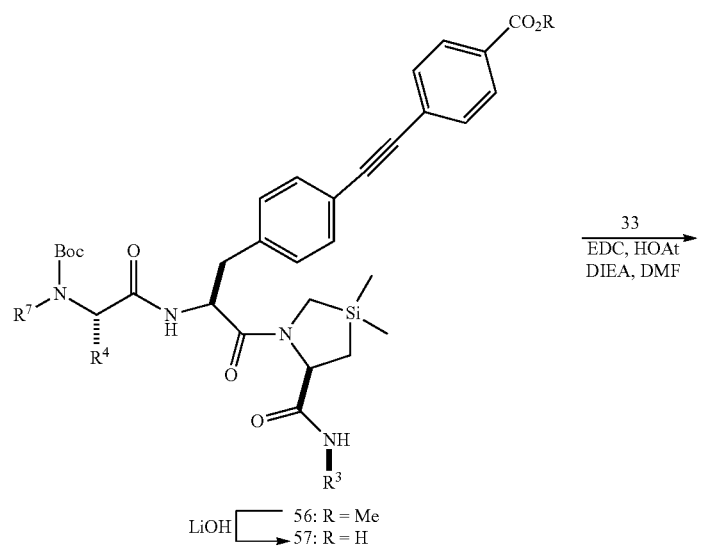

-continued
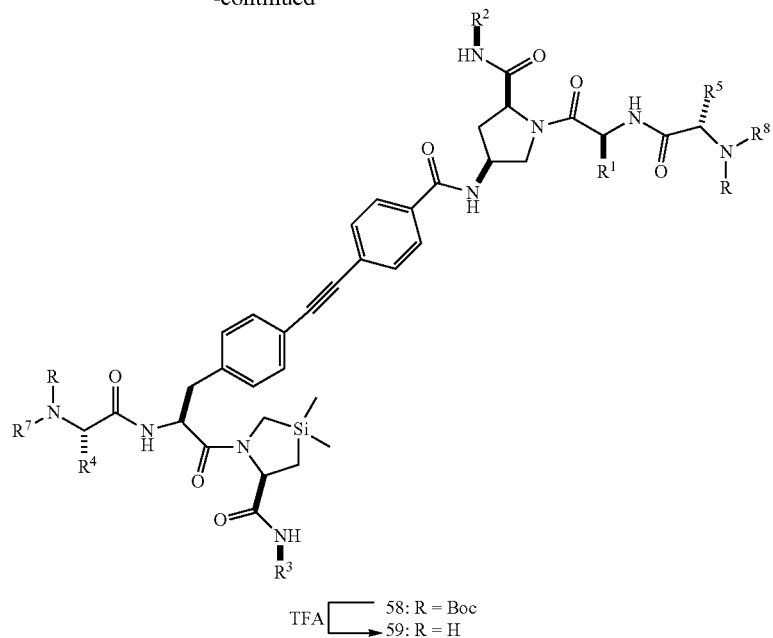
Reduction of the acetylene moiety of intermediate 58, followed by removal of the N-Boc groups of 60 under acidic conditions provided the desired analogues 61 (Scheme 6).
Scheme 6
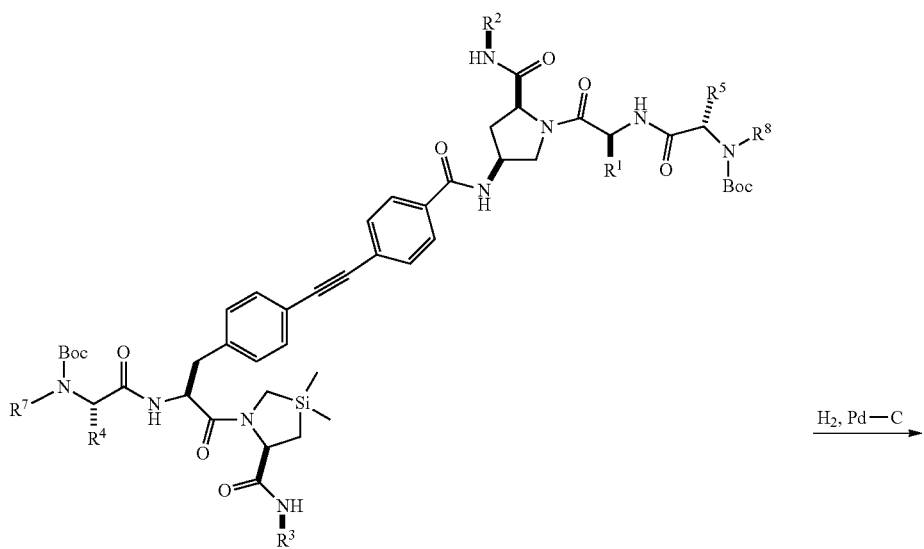

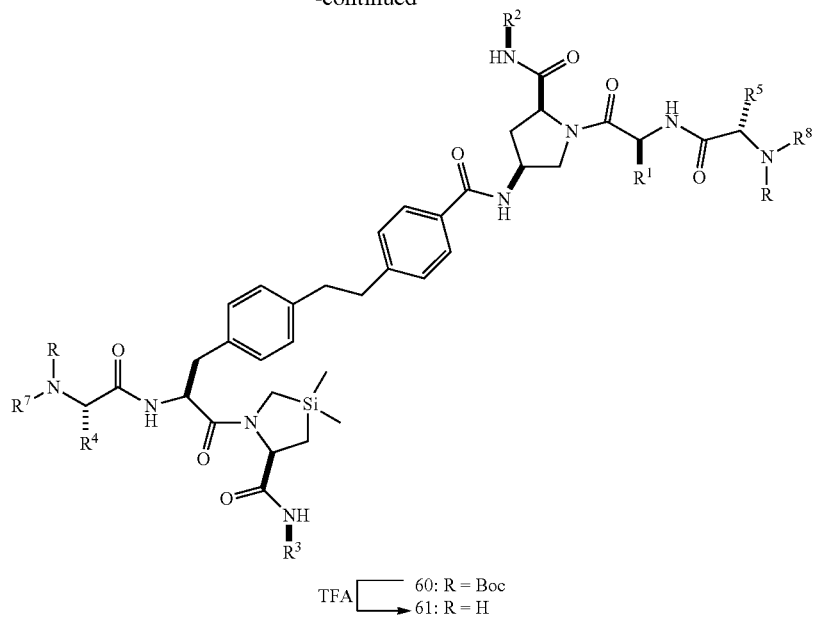
60: R = Boc
61: R = H (TFA)
The biphenyl heterodimeric analogues 68 can be prepared according to the synthetic sequence outlined in Scheme 7. Iodophenylalanine derivative 52 can be coupled with boronic acid 62 to afford the biphenyl dipeptide 63. Intermediate 63 can then be converted to the desired analogues 68 using chemistry described above.
Scheme 7
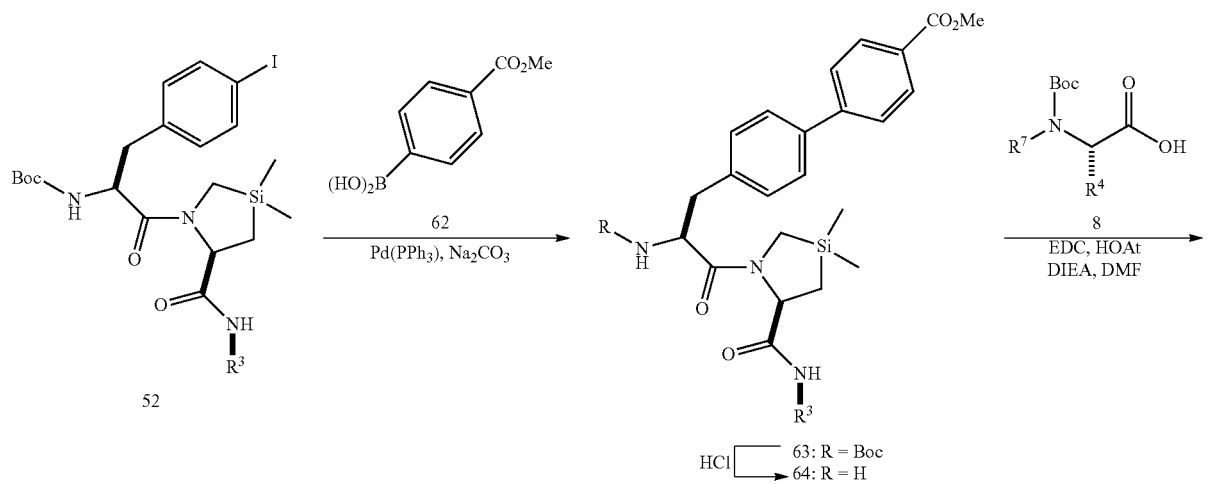
63: R = Boc
64: R = H (HCl)

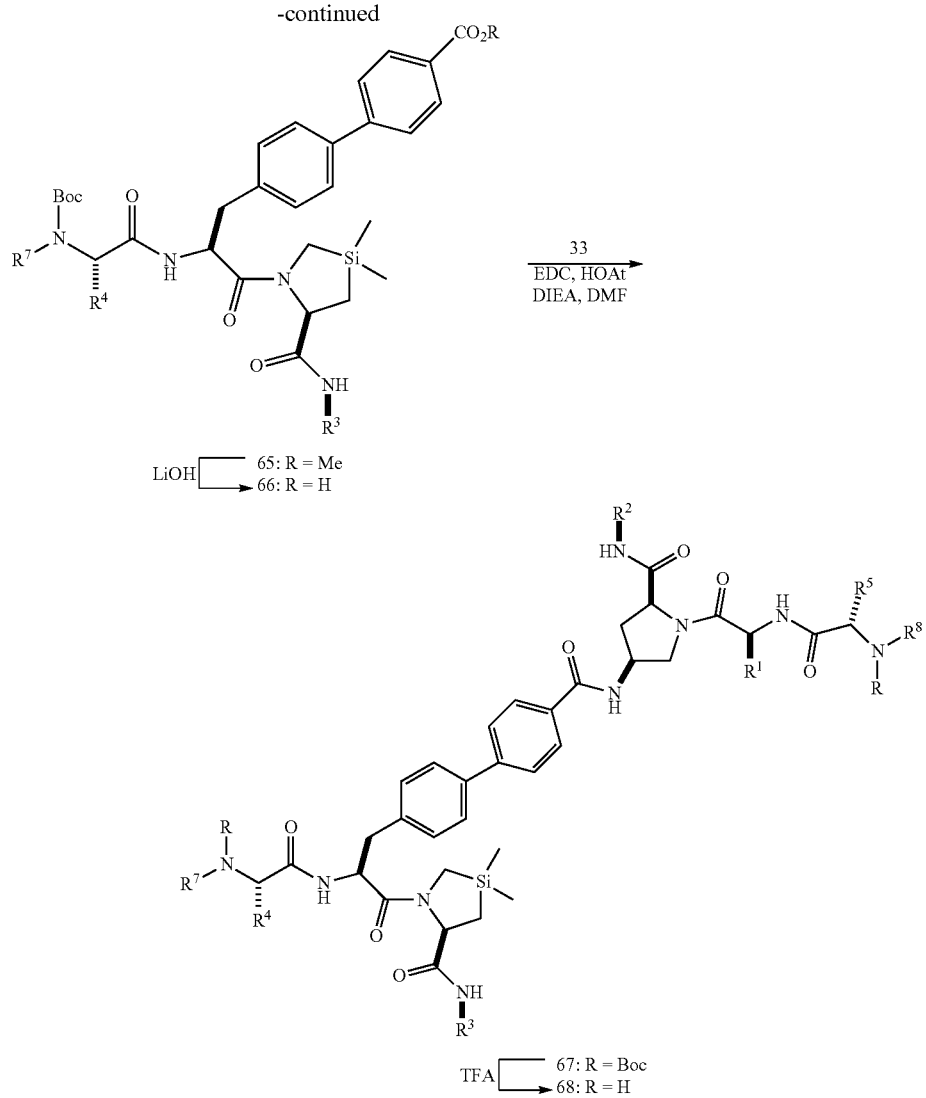

The acetylene-based heterodimeric analogues 73 can be prepared using the synthetic route outlined in Scheme 8. Iodophenylalanine derivative 69, derived from the base-promoted hydrolysis of proline derivative 52, can be coupled with N-Boc amino acid 8 to afford intermediate 70. Key peptide intermediate 33 can be coupled with propiolic acid (53) to furnish the required acetylene derivative 71. Coupling of phenyliodide 70 with acetylene 71 led to heterodimer 72. Removal of the N-Boc groups of 72 under acidic conditions provided the desired analogues 73.

Scheme 8

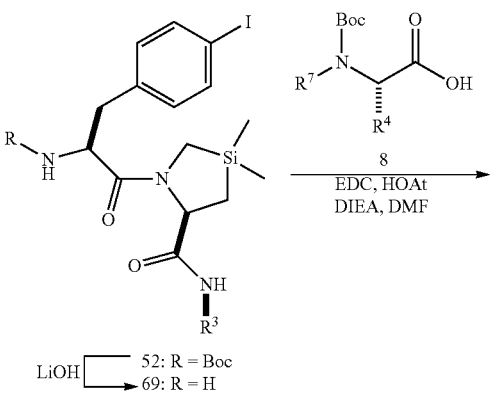

-continued

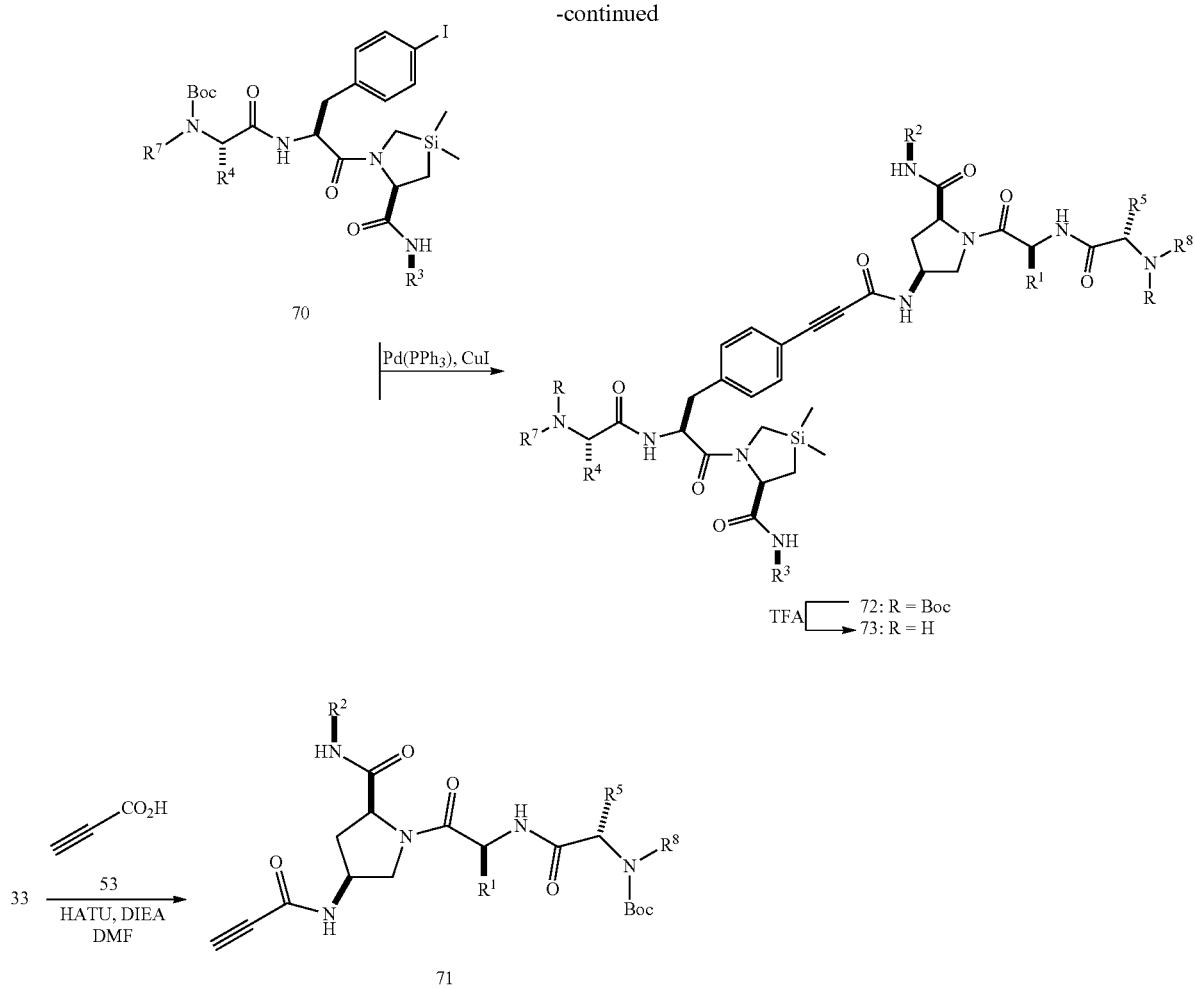

The synthetic route to prepare P3-P4' linked analogues (e.g., 83) is outlined in Scheme 9. Silaproline intermediate 1 can be coupled to secondary amine 74 using for example, DMT-MM to provide amide 75. Removal of the N-Boc protecting group of 75 under acidic conditions followed by coupling of the requisite acid 76 with N-Boc amino acid 77 affords peptide 78. Removal of the N-Boc protecting group of 78 under acidic conditions followed by coupling of the requisite acid 79 with N-Boc amino acid 8 gave peptide 80. Base-promoted hydrolysis of the ester 80 provided the carboxylic acid 81, which was coupled to peptide 33 to give dimer 82. Global deprotection of 82 under acidic conditions furnished the desired analogues 83.

Scheme 9

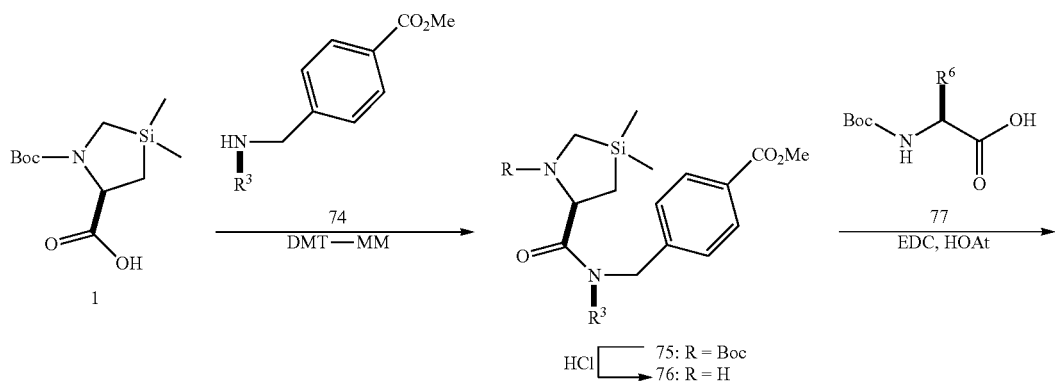

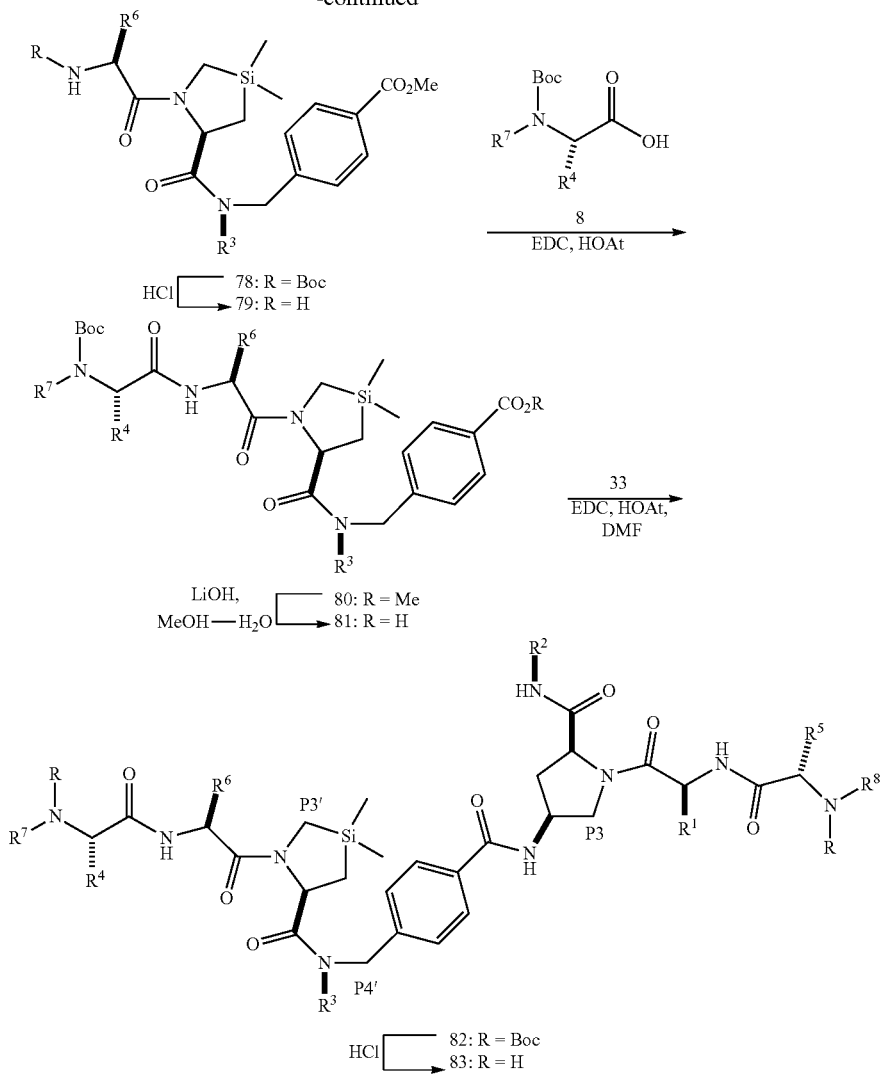

EXAMPLES

General Experimental

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked REDISEP® $R_f$ silica gel columns on a CombiFlash Companion machine.

Preparative Reverse Phase HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 PHENOMENEX® Luna S5 ODS 21×100 mm (flow rate=20 mL/min), or YMC S5 ODS 20×100 mm (flow rate=20 mL/min) or Waters XBridge C18 19×250 mm (flow rate=20 mL/min). Preparative Supercritical Fluid Chromatography (SFC) was performed using 78% $CO_2$/MeOH buffered with 0.1% diethylamine and detection at 220 nm on a CHIRALPAK® AS-H IDS 25×3 cm column (flow rate=85 mL/min).

All final products were characterized by $^1H$ NMR, RP HPLC and electrospray ionization (ESI) or atmospheric pressure ionization (API) mass spectrometry (MS). $^1H$ NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

Abbreviations

AcOH acetic acid
$Ac_2O$ acetic anhydride
ADDP 1,1'-(azodicarbonyl)dipiperidine
aq. aqueous
Bn benzyl
Boc t-butyl carbamate
$Boc_2O$ di-t-butyl dicarbonate
Bu butyl Cbz benzyl carbamate
conc. concentrated
DCE dichloroethane
DCM dichloromethane
DIAD diisopropyl azodicarboxylate
DIEA diisopropylethylamine
DMAP 4-N,N-dimethylaminopyridine
DMF dimethyl formamide
DMSO dimethyl sulfoxide
DMT-MM 4-(4,6-dimethoxy-1,3,5-triazin-2-yl)-4-methyl-morpholinium chloride
EDC 1-(dimethylaminopropyl)-3-ethylcarbodiimide hydrochloride
Et ethyl
EtOAc ethyl acetate
EtOH ethanol
$Et_2O$ diethyl ether
$Et_3N$ triethylamine
Fmoc 9-fluorenylmethyl carbamate
h hour(s)
HATU O-(7-azabenzotriazol-1-yl)-N,N,N',N'-tetramethyluronium hexafluorophosphate
HOAt 1-hydroxy-7-azabenzotriazole
HPLC high pressure liquid chromatography
i-PrOH isopropanol
KOAc potassium acetate
min minute(s)
Me methyl
MeCN acetonitrile
MeOH methanol
$Me_2NH$ dimethyl amine
NaHMDS sodium bis(trimethylsilyl)amide
$Na(OAc)_3BH$ sodium triacetoxyborohydride
n-BuLi n-butyl lithium
NCS N-chlorosuccinimide
NMM N-methylmorpholine
NMP n-methylpyrrolidinone
NMR nuclear magnetic resonance
OTf trifluoromethylsulfonyloxy
Pd/C palladium on carbon
$Pd(dppf)_2Cl_2$ [1,1'-bis(diphenylphosphino)ferrocene]dichloropalladium(II)
$Pd(OAc)_2$ palladium acetate
$Pd(PPh_3)_4$ tetrakis(triphenylphosphine)palladium
$Pd_2(dba)_3$ tris(dibenzylideneacetone)dipalladium(0)
Ph phenyl
PhMe toluene
$Ph_2TfN$ 1,1,1-trifluoro-N-phenyl-N-(trifluoromethyl)sulfonyl methanesulfonamide
$PPh_3$ triphenyl phosphorus
rt room temperature
sat. saturated
t-Bu tertiary butyl
t-BuOH tertiary butanol
TFA trifluoroacetic acid
$Tf_2O$ trifluoromethylsulfonic anhydride
THF tetrahydrofuran
TMS trimethylsilyl
TsO p-toluenesulfonyl Example 1

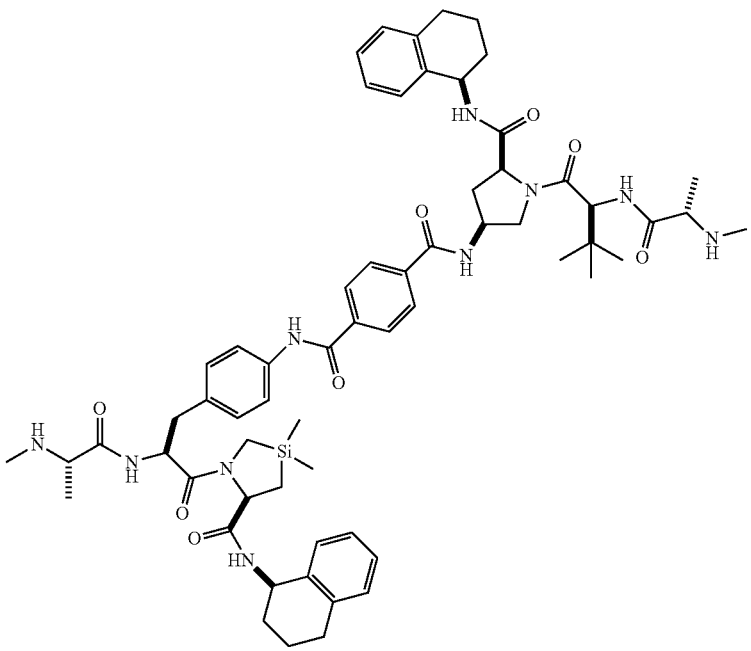

N1-((3S,5S)-1-(S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N4-(4-((S)-3-(R)-3,3-dimethyl-5-(((R)-1,2,3,4-tetrahydronaphthalen-1-yl)carbamoyl)-1,3-azasilolidin-1-yl)-2-((S)-2-(methylamino)propanamido)-3-oxopropyl)phenyl)terephthalamide

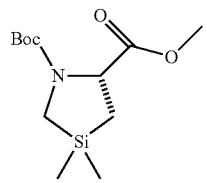

A) (R)-1-tert-Butyl-5-methyl 3,3-dimethyl-1,3-azasilolidine-1,5-dicarboxylate The title compound was prepared according to a literature procedure found in the following reference: *Eur. J. Org. Chem.*, 807-811 (2000). To a solution of (2R,5R)-2-(((iodomethyl)dimethylsilyl)methyl)-5-isopropyl-3,6-dimethoxy-2,5-dihydropyrazine (8.4 g, 21 mmol) in MeOH (50 mL) was added HCl (3 N, 25 mL, 74 mmol). The reaction mixture was stirred at rt for 18 h. The reaction mixture was concentrated in vacuo and the residue was co-evaporated four times with MeOH to remove the water. The residue was dissolved in ethyl ether (50 mL) and DCM (20 mL). Upon the addition of DIEA (12 mL, 68 mmol) at ice bath temperature, a white solid appeared. The reaction mixture was stirred at rt for 3 h. To the reaction mixture was added BOC$_2$O (12 mL, 53 mmol) and the reaction mixture was stirred at rt for 2 h. The product was extracted with EtOAc (3×) and the combined organic extracts were washed with brine (2×), dried over MgSO$_4$, filtered and concentrated in vacuo. The residue was purified by flash column chromatography on SiO$_2$ (eluting with 20% EtOAc/hexane) to afford the title compound (3.9 g, 68%). $^1$H NMR (400 MHz, CDCl$_3$) δ 4.89-4.53 (m, 1H), 3.71 (s, 3H), 2.96-2.81 (m, 1H), 2.80-2.63 (m, 1H), 1.52-1.35 (m, 9H), 1.36-1.21 (m, 1H), 1.10 (dd, J=15.1, 3.4 Hz, 1H), 0.29-0.16 (m, 6H); MS(ESI$^+$) m/z 274.1 (M+H)$^+$.

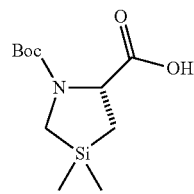

B) (R)-1-(tert-Butoxycarbonyl)-3,3-dimethyl-1,3-azasilolidine-5-carboxylic acid To a solution of (R)-1-tert-butyl 5-methyl 3,3-dimethyl-1,3-azasilolidine-1,5-dicarboxylate (3.1 g, 11.3 mmol, *Eur. J. Org. Chem.*, 807-811 (2000)) in THF (10 mL) and MeOH (15 mL) was added a solution of lithium hydroxide monohydrate (2.9 g, 68 mmol) in water (15 mL). The resulting reaction mixture was stirred at rt for 4 h and the pH was adjusted to 1 using 1N HCl. The resulting aqueous layer was extracted with ethyl ether (2×). The organic solution was dried over MgSO$_4$ and concentrated in vacuo to afford the title compound as a glassy material (2.9 g, 99%). $^1$H NMR (400 MHz, CDCl$_3$) δ 4.91-4.53 (m, 1H), 3.06-2.47 (m, 2H), 1.61-1.04 (m, 11H), 0.27 (d, J=6.8 Hz, 6H); MS(ESI$^+$) m/z 260.1 (M+H)$^+$.

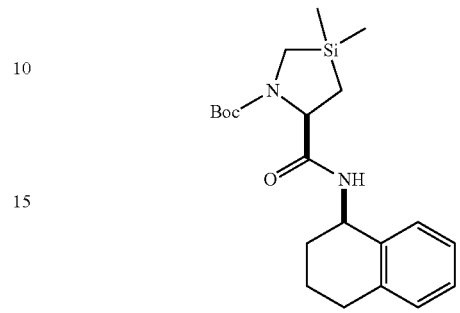

C) (R)-tert-Butyl 3,3-dimethyl-5-(((R)-1,2,3,4-tetrahydronaphthalen-1-yl)carbamoyl)-1,3-azasilolidine-1-carboxylate To a solution of (R)-1-(tert-butoxycarbonyl)-3,3-dimethyl-1,3-azasilolidine-5-carboxylic acid (1.0 g, 3.9 mmol) in DMF (9 mL) at 0° C. was added EDC (1.3 g, 6.6 mmol) and 3H-[1,2,3]-triazolo[4,5-b]pyridin-3-ol (0.53 g, 3.9 mmol). The resulting mixture was stirred for 5 minutes and treated with a solution of (R)-1,2,3,4-tetrahydronaphthalen-1-amine (Alfa Aesar, 0.60 g, 4.1 mmol) in DMF (4 mL) and then DIEA (0.94 mL, 5.4 mmol). The reaction mixture was stirred at rt for 1.5 h and diluted with ethyl acetate and brine. The organic layer was separated, washed with brine, dried over MgSO$_4$, and concentrated in vacuo. The residue was purified by flash column chromatography on SiO$_2$ (eluting with 20% EtOAc/hexane) to afford the title compound (1.25 g, 83%). $^1$H NMR (400 MHz, CDCl$_3$) δ 7.22-7.02 (m, 4H), 5.22-4.61 (m, 2H), 3.16-2.65 (m, 3H), 2.52 (d, J=14.5 Hz, 1H), 2.12-1.95 (m, 1H), 1.88-1.76 (m, 3H), 1.52-1.28 (m, 11H), 0.43-0.16 (m, 6H); MS(ESI$^+$) m/z 389.4 (M+H)$^+$.

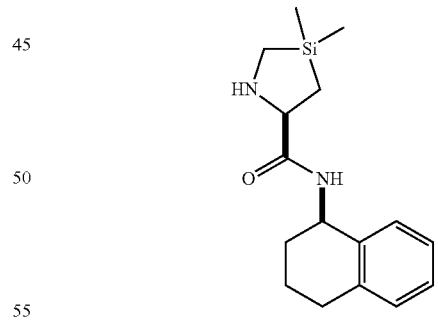

D) (R)-3,3-Dimethyl-N—((R)-1,2,3,4-tetrahydronaphthalen-1-yl)-1,3-azasilolidine-5-carboxamide To a solution of (R)-tert-butyl-3,3-dimethyl-5-((R)-1,2,3,4-tetrahydronaphthalen-1-ylcarbamoyl)-1,3-azasilolidine-1-carboxylate (4.9 g, 12 mmol) in CH$_2$Cl$_2$ (50 mL) was added TFA (7 mL) at rt. After 4 h, the reaction mixture was concentrated in vacuo to obtain (R)-3,3-dimethyl-N—((R)-1,2,3,4-tetrahydronaphthalen-1-yl)-1,3-azasilolidine-5-carboxamide TFA salt (5.0 g, 12 mmol, 100% yield) as a white solid, which was used directly in the next step. ¹H NMR (400 MHz, CD₃OD) δ 7.14-7.25 (m, 4H), 5.12 (t, J=5.5 Hz, 1H), 4.0 (dd, J=11.9, 6.6 Hz, 1H), 2.79 (m, 2H), 2.76 (d, J=4.5 Hz, 1H), 2.45 (dd, J=15, 4.5 Hz, 1H), 1.85-2.06 (m, 4H), 1.53 (dd, J=15, 6.8 Hz, 1H), 1.08 (dd, J=15, 4.5 Hz, 1H), 0.41 (3H), 0.38 (s, 3H); MS(ESI⁺) m/z 289 (M+H)⁺.

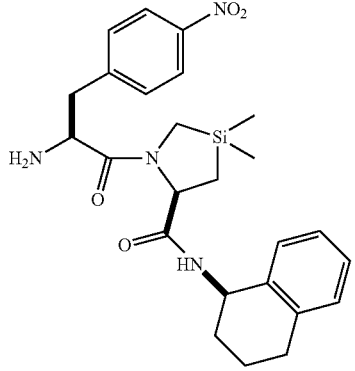

E) (R)-1-(S)-2-Amino-3-(4-nitrophenyl)propanoyl)-3,3-dimethyl-N—((R)-1,2,3,4-tetrahydronaphthalen-1-yl)-1,3-azasilolidine-5-carboxamide To a solution of (S)-2-((tert-butoxycarbonyl)amino)-3-(4-nitrophenyl)propanoic acid (89 mg, 0.29 mmol) in DMF (1.5 mL) at rt was added 4-(4,6-dimethoxy-1,3,5-triazin-2-yl)-4-methylmorpholin-4-ium chloride (86 mg, 0.31 mmol) followed by a solution of (R)-3,3-dimethyl-N—((R)-1,2,3,4-tetrahydronaphthalen-1-yl)-1,3-azasilolidone-5-carboxamide TFA salt (0.11 g, 0.26 mmol) and DIEA (115 μL) in DMF (2 mL). After 2.5 h, the reaction mixture was mixed with water and EtOAc. The organic layer was separated, washed with 1N HCl, and then aq. NaHCO₃ solution, dried over MgSO₄ and concentrated in vacuo to obtain the crude coupling product as a glassy material. MS(ESI⁻) m/z 581 (M+H)⁺.

The crude coupling product obtained above was mixed with CH₂Cl₂ (10 mL) and TFA (1 mL) at rt. After 2.5 h, the reaction mixture was concentrated in vacuo to obtain the title compound as the TFA salt (0.15 g, 0.25 mmol, 97% yield. The glassy material was used directly in the next step without further purification. ¹H NMR (400 MHz, CD₃OD) δ 8.19 (d, J=8.6 Hz, 2H), 7.62 (d, J=8.6 Hz, 2H), 7.29 (d, J=7.5 Hz, 1H), 7.15-7.01 (m, 3H), 4.96 (dd, J=10.1, 4.0 Hz, 1H), 4.83-4.75 (m, 1H), 3.47 (dd, J=14.5, 5.3 Hz, 1H), 3.32-3.22 (m, 2H), 3.15 (d, J=13.0 Hz, 1H), 2.88-2.73 (m, 2H), 2.08-1.69 (m, 4H), 1.41-1.03 (m, 3H), 0.34 (s, 3H), 0.29 (s, 3H); MS(ESI⁺) m/z 481 (M+H)⁺.

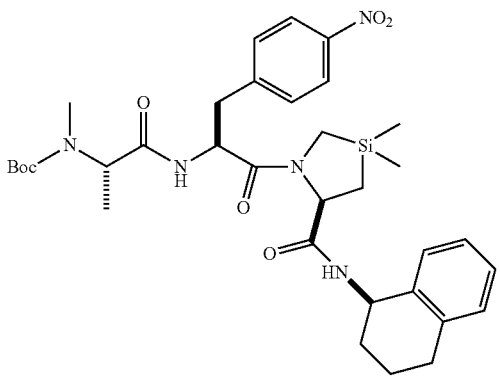

F) tert-Butyl ((S)-1-(((S)-1-(R)-3,3-dimethyl-5-((R)-1,2,3,4-tetrahydronaphthalen-1-yl)carbamoyl)-1,3-azasilolidin-1-yl)-3-(4-nitrophenyl)-1-oxopropan-2-yl)amino)-1-oxopropan-2-yl)(methyl)carbamate To a solution of (S)-2-((tert-butoxycarbonyl)(methyl)amino)propanoic acid (251 mg, 1.24 mmol) in DMF (5 mL) at rt was added HATU (470 mg, 1.24 mmol) followed by a solution of (R)-1-(S)-2-amino-3-(4-nitrophenyl)propanoyl)-3,3-dimethyl-N—((R)-1,2,3,4-tetrahydronaphthalen-1-yl)-1,3-azasilolidine-5-carboxamide (540 mg, 1.12 mmol) and DIEA (196 μL, 1.12 mmol) in DMF (5 mL). The reaction mixture was stirred at rt for 2 h and mixed with EtOAc and water. The organic layer was separated, washed with 1N HCl followed by aq. NaHCO₃ solution, dried over MgSO₄ and concentrated in vacuo to obtain the title compound (520 mg, 0.78 mmol, 69.5% yield) as a white solid. The product was used directly in the next step without further purification. ¹H NMR (400 MHz, CDCl₃) δ 8.13 (d, J=8.6 Hz, 2H), 7.29 (d, J=7.5 Hz, 1H), 7.21-7.2 (m, 5H), 6.77 (br. S, 1H), 6.39 (d, J=8.6 Hz, 1H), 5.25-5.06 (m, 3H), 4.60 (br. s, 1H), 3.37-3.04 (m, 2H), 2.85-2.73 (m, 3H), 2.54 (s, 3H), 2.11-1.75 (m, 4H), 1.47 (s, 9H), 1.31 (m, 1H), 1.23 (d, J=7.0 Hz, 3H), 1.03 (m, 1H), 0.45 (s, 3H), 0.29 (s, 3H); MS(ESI⁺) m/z 666 (M+H)⁺.

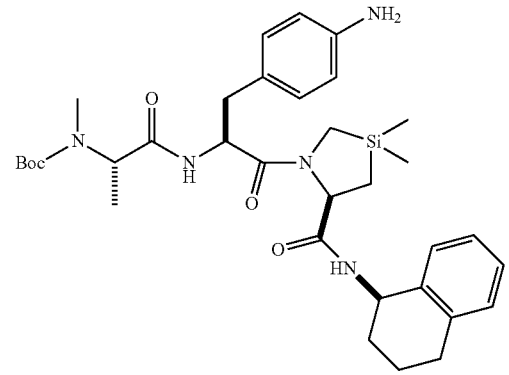

G) tert-Butyl ((S)-1-(((S)-3-(4-aminophenyl)-1-(R)-3,3-dimethyl-5-(((R)-1,2,3,4-tetrahydronaphthalen-1-yl)carbamoyl)-1,3-azasilolidin-1-yl)-1-oxopropan-2-yl)amino)-1-oxopropan-2-yl)(methyl)carbamate The compound tert-butyl-((S)-1-(((S)-1-(((R)-3,3-dimethyl-5-(((R)-1,2,3,4-tetrahydronaphthalen-1-yl)carbamoyl)-1,3-azasilolidin-1-yl)-3-(4-nitrophenyl)-1-oxopropan-2-yl)amino)-1-oxopropan-2-yl)(methyl)carbamate (520 mg) obtained above was mixed with MeOH (25 mL) and 20% Pd(OH)₂ (100 mg) on carbon and the mixture was stirred under 1 atm of H₂ gas for 2 h. The reaction mixture was filtered and the filtrate was concentrated in vacuo to obtain the title compound (500 mg, 0.79 mmol, 70% yield) as a white solid. ¹H NMR (400 MHz, CDCl₃) δ 7.19 (d, J=7.3 Hz, 2H), 7.00 (d, J=7.9 Hz, 2H), 6.67-6.53 (m, 4H), 5.17-5.06 (m, 3H), 3.46 (s, 1H), 2.95 (s, 1H), 2.90-2.70 (m, 5H), 2.66-2.58 (m, 2H), 2.50 (s, 3H), 1.92-1.75 (m, 4H), 1.47 (s, 9H), 1.38 (m, 1H), 1.20 (d, J=7.0 Hz, 3H), 1.01-0.91 (m, 2H), 0.43-0.41 (m, 1H), 0.42 (s, 3H), 0.27 (s, 3H); MS(ESI⁺) m/z 636 (M+H)⁺.

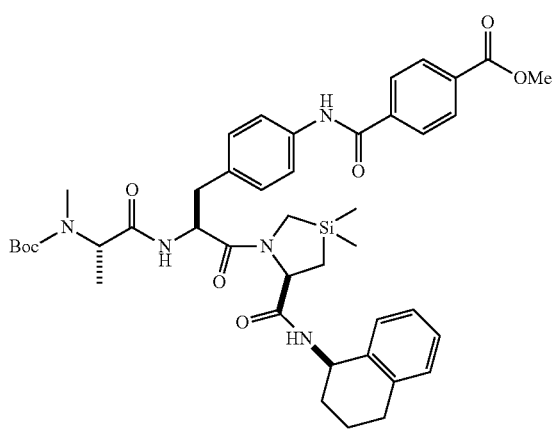

H) Methyl 4-((4-((S)-2-((S)-2-((tert-butoxycarbonyl) (methyl)amino)propanamido)-3-((R)-3,3-dimethyl-5-(R)-1,2,3,4-tetrahydronaphthalen-1-yl)carbamoyl)-1,3-azasilolidin-1-yl)-3-oxopropyl)phenyl) carbamoyl)benzoate To a solution of 4-(methoxycarbonyl)benzoic acid (49.9 mg, 0.277 mmol) in DMF (1.5 mL) at rt was added HATU (105 mg, 0.277 mmol). The reaction mixture was stirred for 10 minutes and treated with a solution of tert-butyl ((S)-1-(S)-3-(4-aminophenyl)-1-(R)-3,3-dimethyl-5-(((R)-1,2,3,4-tetrahydronaphthalen-1-yl)carbamoyl)-1,3-azasilolidin-1-yl)-1-oxopropan-2-yl)amino)-1-oxopropan-2-yl)(methyl) carbamate (160 mg, 0.25 mmol) and DIEA (65.9 μL, 0.377 mmol) in DMF (3 mL). The reaction mixture was stirred for 1 h and directly purified by preparative HPLC to provide the title compound (160 mg, 0.200 mmol, 80% yield) as a white solid. MS(ESI⁺) m/z 799.4 (M+H)⁺.

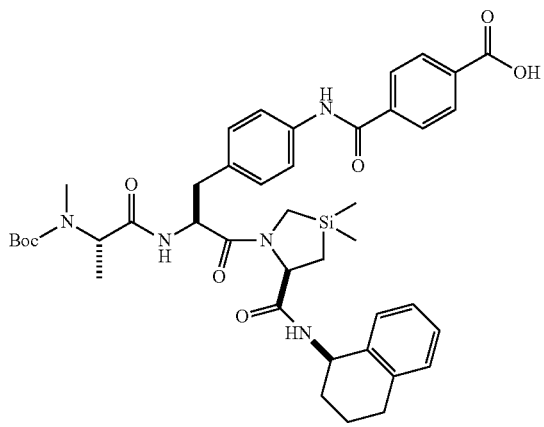

I) 4-((4-((S)-2-((S)-2-((tert-Butoxycarbonyl)(methyl) amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)carbamoyl) benzoic acid A solution of methyl 4-((4-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)carbamoyl)benzoate (160 mg, 0.200 mmol) and LiOH (300 mg) in MeOH (6 mL) and H₂O (2 mL) was stirred at rt for 2.5 h. Most of the MeOH was removed in vacuo and the residue was mixed with EtOAc and 1N HCl (60 mL). The organic layer was separated, dried over MgSO₄ and concentrated in vacuo to obtain the title compound (140 mg, 0.179 mmol, 71% yield) as a white solid. MS(ESI⁺) m/z 784.4 (M+H)⁺.

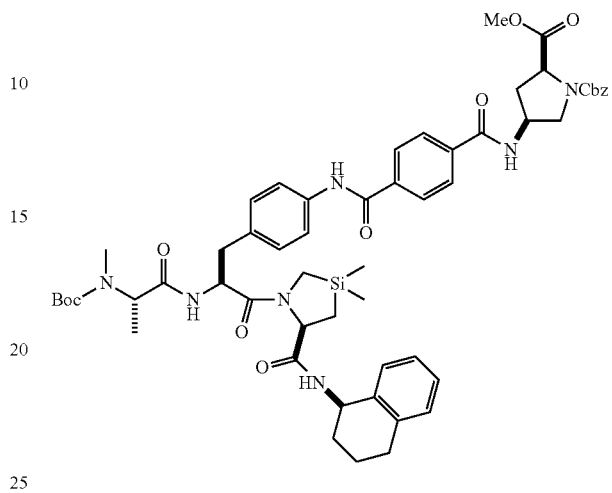

J) (2S,4S)-1-Benzyl 2-methyl 4-(4-((4-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)carbamoyl)benzamido) pyrrolidine-1,2-dicarboxylate To a solution of 4-((4-((S)-2-((S)-2-((tert-butoxycarbonyl) (methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)carbamoyl)benzoic acid (140 mg, 0.179 mmol) in DMF (2.5 mL) at rt was added 4-(4,6-dimethoxy-1,3,5-triazin-2-yl)-4-methylmorpholinium chloride (55 mg). The reaction mixture was stirred for 10 minutes and treated with a solution of (2S,4S)-1-benzyl 2-methyl 4-aminopyrrolidine-1,2-dicarboxylate, HCl (61.8 mg, 0.196 mmol) and DIEA (78 μL, 0.446 mmol). The resulting mixture was stirred at rt for 1 h and directly purified by preparative HPLC to provide the title compound (117 mg, 0.112 mmol, 63% yield) as a white solid. MS(ESI⁺) m/z 1044.5 (M+H)⁺.

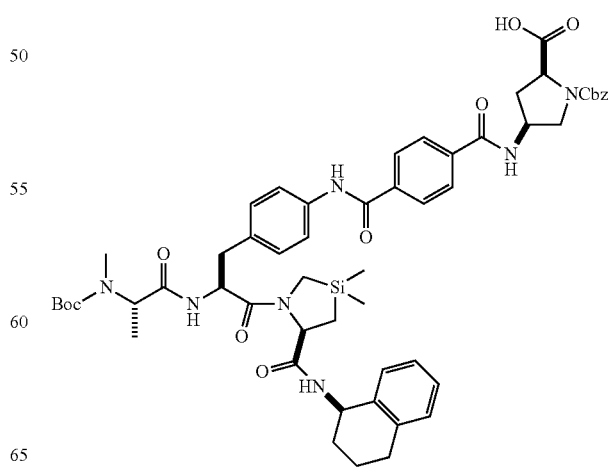

K) (2S,4S)-1-(Benzyloxy)carbonyl)-4-(4-((4-((S)-2-((S)-2-((tert-butoxycarbonyl)(methyl)amino)propanamido)-3-(R)-3,3-dimethyl-5-(((R)-1,2,3,4-tetrahydronaphthalen-1-yl)carbamoyl)-1,3-azasilolidin-1-yl)-3-oxopropyl)phenyl)carbamoyl)benzamido) pyrrolidine-2-carboxylic acid (2S,4S)-1-Benzyl 2-methyl 4-(4-((4-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)carbamoyl)benzamido)pyrrolidine-1,2-dicarboxylate (117 mg) was mixed with a solution of LiOH.H$_2$O (190 mg) in water (2 mL) and MeOH (4 mL) at rt. After 1.5 h, most of the methanol was removed in vacuo and the residue was mixed with EtOAc (60 mL) and 1N HCl (60 mL). The organic layer was separated, washed with water, dried over MgSO$_4$ and concentrated in vacuo to obtain the title compound (115 mg, 0.112 mmol, 100% yield) as a white solid. MS(ESI$^+$) m/z 1030.4 (M+H)$^+$.

carboxylic acid (0.12 g, 0.11 mmol) in DMF (2 mL) at rt was added 4-(4,6-dimethoxy-1,3,5-triazin-2-yl)-4-methylmorpholinium chloride (35 mg, 0.13 mmol). After 5 minutes, a solution of (R)-1,2,3,4-tetrahydronaphthalen-1-amine (18 mg, 0.12 mmol) and DIEA (29 µL, 0.17 mmol) in DMF (1.5 mL) was added. The reaction mixture was stirred for 1 h and directly purified by preparative HPLC to afford the title compound (92 mg, 0.08 mmol, 71.1% yield) as a white solid. MS(ESI$^+$) m/z 1159.6 (M+H)$^+$.

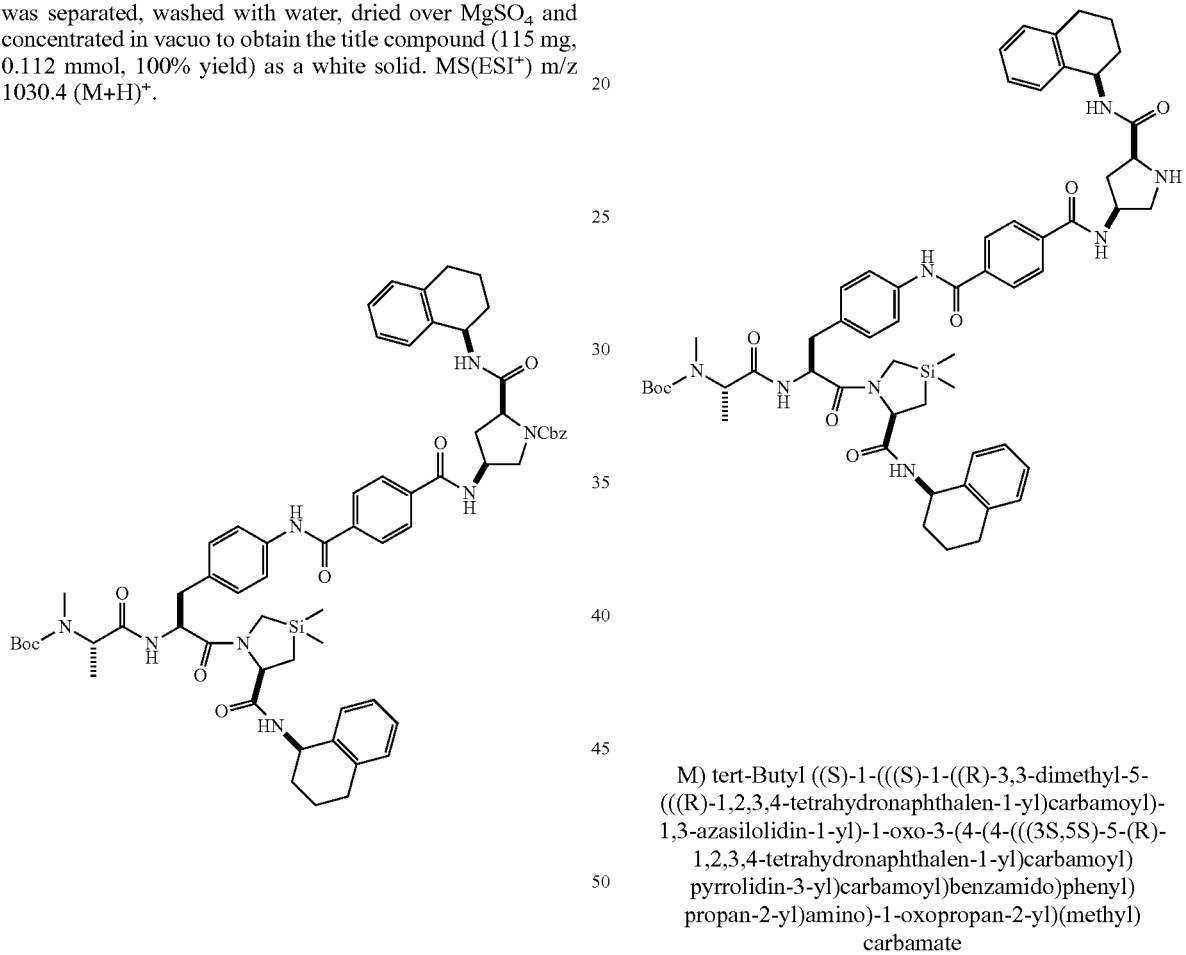

M) tert-Butyl ((S)-1-(((S)-1-((R)-3,3-dimethyl-5-(((R)-1,2,3,4-tetrahydronaphthalen-1-yl)carbamoyl)-1,3-azasilolidin-1-yl)-1-oxo-3-(4-(4-(((3S,5S)-5-(R)-1,2,3,4-tetrahydronaphthalen-1-yl)carbamoyl) pyrrolidin-3-yl)carbamoyl)benzamido)phenyl) propan-2-yl)amino)-1-oxopropan-2-yl)(methyl) carbamate L) (2S,4S)-Benzyl 4-(4-((4-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl) phenyl)carbamoyl)benzamido)-2-(R)-1,2,3,4-tetrahydronaphthalen-1-yl)carbamoyl)pyrrolidine-1-carboxylate To a solution of (2S,4S)-1-((benzyloxy)carbonyl)-4-(4-((4-((S)-2-((S)-2-((tert-butoxycarbonyl)(methyl)amino)propanamido)-3-((R)-3,3-dimethyl-5-((R)-1,2,3,4-tetrahydronaphthalen-1-yl)carbamoyl)-1,3-azasilolidin-1-yl)-3-oxopropyl)phenyl)carbamoyl) benzamido)pyrrolidone-2-

(2S,4S)-Benzyl 4-(4-((4-((S)-2-((tert-butoxycarbonyl)(methyl)amino)propanamido)-3-((R)-3,3-dimethyl-5-((R)-1,2,3,4-tetrahydronaphthalen-1-yl)carbamoyl)-1,3-azasilolidin-1-yl)-3-oxopropyl)phenyl)carbamoyl)benzamido)-2-((R)-1,2,3,4-tetrahydronaphthalen-1-yl)carbamoyl) pyrrolidone-1-carboxylate (92 mg, 0.08 mmol) was mixed with 20% Pd(OH)$_2$ on carbon (35 mg) in MeOH (10 mL). The reaction mixture was stirred under 1 atm of H$_2$ gas at rt for 3 h. The solids were removed and the filtrate was concentrated in vacuo to obtain the title compound (75 mg, 0.07 mmol, 66% yield) as a white solid. MS(ESI$^+$) m/z 1026.1 (M+H)$^+$.

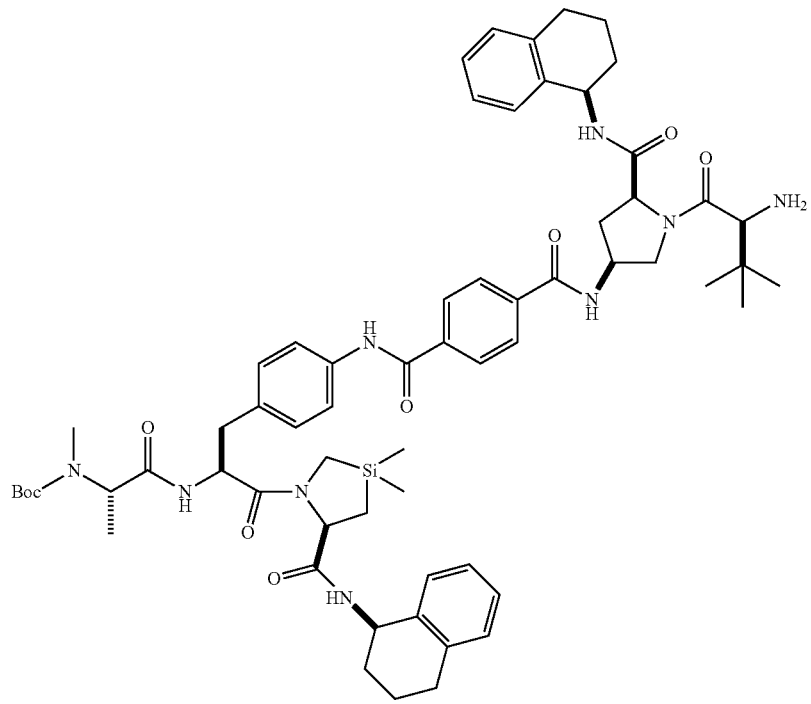

N) tert-Butyl ((S)-1-(((S)-3-(4-(4-(((3S,5S)-1-(S)-2-amino-3,3-dimethylbutanoyl)-5-((R)-1,2,3,4-tetrahydronaphthalen-1-yl)carbamoyl)pyrrolidin-3-yl)carbamoyl)benzamido)phenyl)-1-(R)-3,3-dimethyl-5-((R)-1,2,3,4-tetrahydronaphthalen-1-yl)carbamoyl)-1,3-azasilolidin-1-yl)-1-oxopropan-2-yl)amino)-1-oxopropan-2-yl)(methyl)carbamate, hydrochloride salt To a solution of (S)-2-(((((9H-fluoren-9-yl)methoxy)carbonyl)amino)-3,3-dimethylbutanoic acid (28 mg, 0.080 mmol) in DMF (1.2 mL) at rt was added 4-(4,6-dimethoxy-1,3,5-triazin-2-yl)-4-methylmorpholinium chloride (21 mg, 0.08 mmol). The reaction mixture was stirred for 10 minutes and treated with a solution of tert-butyl ((S)-1-(((S)-1-(R)-3,3-dimethyl-5-((R)-1,2,3,4-tetrahydronaphthalen-1-yl)carbamoyl)-1,3-azasilolidin-1-yl)-1-oxo-3-(4-(4-(((3S,5S)-5-((R)-1,2,3,4-tetrahydronaphthalen-1-yl)carbamoyl)pyrrolidin-3-yl)carbamoyl)benzamido)phenyl)propan-2-yl)amino)-1-oxopropan-2-yl)(methyl)carbamate (75 mg, 0.073 mmol) and DIEA (20 µL) in DMF (2 mL). The mixture was stirred at rt for 1 h and mixed with EtOAc and water. The organic layer was separated, washed with 1N HCl, followed by sat. aq NaHCO$_3$ solution. The organics were dried over MgSO$_4$ and concentrated in vacuo to obtain the title compound, which was used directly in the next step. MS(ESI$^+$) m/z 1361.6 (M+H)$^+$.

The coupling product obtained above was mixed with CH$_2$Cl$_2$ (4 mL) and piperidine (0.3 mL) at ambient temperature. After stirring for 35 minutes at rt, the solution was treated with HOAc (0.3 mL), and the mixture was mostly concentrated in vacuo. The resulting residue was purified by preparative HPLC to obtain the title compound as the TFA salt (27 mg, 32% yield, white solid). MS(ESI$^+$) m/z 1139.3 (M+H)$^+$.

O) N1-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N4-(4-((S)-3-((R)-3,3-dimethyl-5-(((R)-1,2,3,4-tetrahydronaphthalen-1-yl)carbamoyl)-1,3-azasilolidin-1-yl)-2-((S)-2-(methylamino)propanamido)-3-oxopropyl)phenyl)terephthalamide To a solution of amine ((S)-2-((tert-butoxycarbonyl)(methyl)amino)propanoic acid (4.6 mg, 0.023 mmol) in DMF (1 mL) at rt was added 4-(4,6-dimethoxy-1,3,5-triazin-2-yl)-4-methylmorpholinium chloride (6.5 mg, 0.025 mmol). The reaction mixture was stirred for 10 minutes and treated with a solution of tert-butyl ((S)-1-(((S)-3-(4-(4-(((3S,5S)-1-((S)-2-amino-3,3-dimethylbutanoyl)-5-(((R)-1,2,3,4-tetrahydronaphthalen-1-yl)carbamoyl)pyrrolidin-3-yl)carbamoyl)benzamido)phenyl)-1-((R)-3,3-dimethyl-5-(((R)-1,2,3,4-tetrahydronaphthalen-1-yl)carbamoyl)-1,3-azasilolidin-1-yl)-1-oxopropan-2-yl)amino)-1-oxopropan-2-yl)(methyl)carbamate (26 mg, 0.021 mmol) and DIEA (10 µL) in DMF (1.5 mL). The mixture was stirred at rt for 1 h and directly purified by preparative HPLC to obtain the desired coupling product. MS(ESI$^+$) m/z 1324.9 (M+H)$^+$.

The above residue was dissolved in CH$_2$Cl$_2$ (3 mL) and treated with 0.4 mL of 4N HCl in dioxane at rt. After stirring for 50 minutes at rt, the reaction mixture was concentrated in vacuo and the residue was mixed with water and lyophilized to obtain the title compound (18 mg, 0.014 mmol, 69% yield) as a white solid. MS(ESI$^+$) m/z 1123.8 (M+H)$^+$.

Example 2

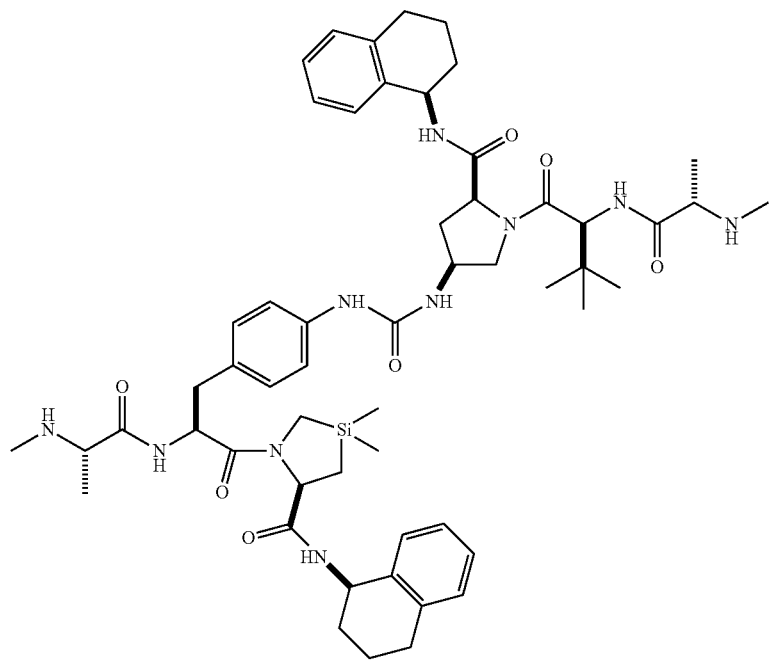

(R)-1-((S)-3-(4-(3-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)ureido)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide

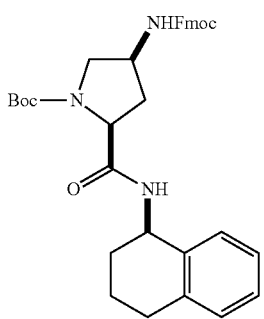

A) (2S,4S)-tert-Butyl 4-((((9H-fluoren-9-yl)methoxy)carbonyl)amino)-2-(((R)-1,2,3,4-tetrahydronaphthalen-1-yl)carbamoyl)pyrrolidine-1-carboxylate To a solution of (2S,4S)-Boc-4-(Fmoc-amino)-proline (Chem-Impex, 6.00 g, 13.3 mmol) in DMF (20 mL) at 0° C. were added EDC (3.05 g, 15.9 mmol), HOAt (2.17 g, 15.9 mmol) and NMM (4.38 mL, 39.8 mmol). The reaction mixture was stirred at ice bath temperature for 20 min then treated with a solution of (R)-1,2,3,4-tetrahydronaphthalen-1-amine (Alfa Aesar, 2.15 g, 14.6 mmol) in DMF (2 mL). The reaction mixture was stirred at rt for 1 h and cold water (100 mL) was added to the reaction mixture. The solid that formed was collected by filtration and washed with cold water (100 mL). The solid was dissolved in $CH_2Cl_2$ (200 mL) and the organic solution was washed with 5% aq. citric acid solution and brine, dried over $MgSO_4$, and filtered. The filtrate was concentrated in vacuo. The residue was dissolved in $CH_2Cl_2$ and purified by flash column chromatography (gradient elution from 10 to 30% EtOAc in $CH_2Cl_2$) provided the title compound (6.70 g, 87%) as a light tan solid. $^1$H NMR (400 MHz, $CDCl_3$) δ 7.79 (d, J=7.5 Hz, 2H), 7.67 (d, J=7.3 Hz, 2H), 7.42 (td, J=7.2, 4.0 Hz, 2H), 7.37-7.03 (m, 6H), 5.22 (br. s., 1H), 4.57-4.23 (m, 5H), 3.68-3.49 (m, 2H), 2.91-2.74 (m, 2H), 2.52 (d, J=13.4 Hz, 1H), 2.35-2.21 (m, 1H), 2.14 (d, J=5.1 Hz, 1H), 1.97-1.80 (m, 3H), 1.44 (s, 9H); MS(ESI$^+$) m/z 582.2 (M+H)$^+$.

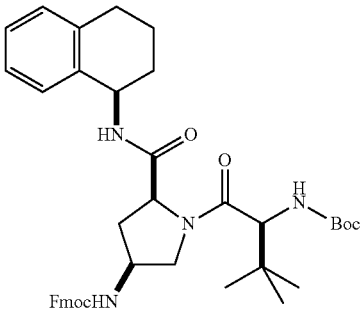

B) tert-Butyl ((S)-3,3-dimethyl-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate To a solution of (2S,4S)-tert-butyl 4-((((9H-fluoren-9-yl)methoxy)carbonyl)amino)-2- (((R)-1,2,3,4-tetrahydronaphthalen-1-yl)carbamoyl)pyrrolidine-1-carboxylate (6.70 g, 11.5 mmol) in CH₂Cl₂ (50 mL) at rt was added TFA (15 mL) dropwise. The reaction mixture was stirred at rt for 2 h, and then concentrated in vacuo. The residue was dissolved in CH₂Cl₂ (200 mL) and washed with aq. K₂HPO₄ solution (50 mL). The organic layer was dried over MgSO₄, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 100%), which was used directly in the next step.

To a solution of (S)-2-((tert-butoxycarbonyl)amino)-3,3-dimethylbutanoic acid (3.19 g, 13.8 mmol) in DMF (20 mL) at 0° C. were added EDC (3.31 g, 17.3 mmol), HOAt (2.35 g, 17.3 mmol) and NMM (3.80 mL, 34.5 mmol). The reaction mixture was stirred at ice bath temperature for 20 min, then treated with a suspension of (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 11.5 mmol) in DMF (5 mL). The reaction mixture was stirred at rt for 1 h and cold water (200 mL) was added to the reaction mixture. The solid that formed was collected by filtration and washed with of cold water (100 mL). The solid was dissolved in CH₂Cl₂ (200 mL). The organic solution was washed with aq. NaHCO₃ solution, 5% aq. citric acid solution and brine, dried over MgSO₄ and filtered. The filtrate was concentrated in vacuo. The residue was dissolved in CH₂Cl₂ and purified using flash column chromatography (gradient elution from 10 to 30% EtOAc in CH₂Cl₂) provided the title compound (7.10 g, 89%) as a light tan solid. MS(ESI⁻) m/z 695.5 (M+H)⁻.

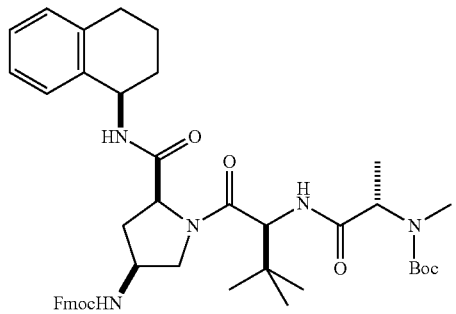

C) tert-Butyl ((S)-1-(((S)-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate (7.10 g, 10.2 mmol) in CH₂Cl₂ (50 mL) at rt was added TFA (15 mL) dropwise. The reaction mixture was stirred at rt for 2 h, and then concentrated in vacuo. The residue was dissolved in CH₂Cl₂ (200 mL) and washed with aq. K₂HPO₄ solution (50 mL). The organic layer was dried over MgSO₄, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (6.08 g, 100%), which was used directly in the next step.

To a solution of (S)-2-((tert-butoxycarbonyl)(methyl)amino)propanoic acid (Chem-Impex, 2.49 g, 12.3 mmol) in DMF (20 mL) at 0° C. were added EDC (2.94 g, 15.3 mmol), HOAt (2.09 g, 15.3 mmol) and NMM (2.81 mL, 25.6 mmol). The reaction mixture was stirred at ice bath temperature for 20 min, and then treated with a solution of (9H-fluoren-9-yl)methyl ((3S,5S)-5-(((R)-1,2,3,4-tetrahydronaphthalen-1-yl)carbamoyl)pyrrolidin-3-yl)carbamate (6.45 g, 10.2 mmol) in DMF (5 mL). The reaction mixture was stirred at rt for 2 h and then cold water (200 mL) was added to the reaction mixture. The solid that formed was collected by filtration and washed with cold water (100 mL). The solid was dissolved in CH₂Cl₂ (200 mL). The organic solution was washed with aq. NaHCO₃ solution, 5% aq. citric acid solution and brine, dried over MgSO₄, and filtered. The filtrate was concentrated in vacuo. The residue was dissolved in CH₂Cl₂ and purified by flash column chromatography (gradient elution from 10 to 40% EtOAc in CH₂Cl₂) provided the title compound (6.14 g, 77%) as a light tan solid. MS(ESI⁺) m/z 780.5 (M+H)⁺.

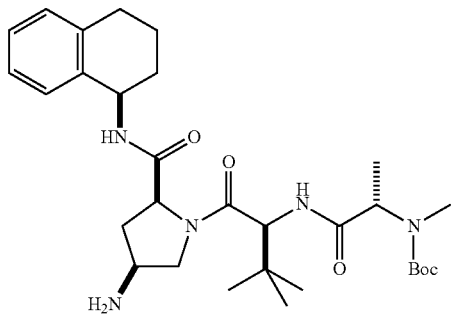

D) tert-Butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (6.14 g, 7.87 mmol) in CH₂Cl₂ (40 mL) was added piperidine (4.67 mL, 47.2 mmol) dropwise. The reaction mixture was stirred at rt for 2 h and concentrated in vacuo. The residue was washed with methanol and the resulting solid was removed by filtration. The filtrate was concentrated in vacuo and purified by flash column chromatography (gradient elution from 0 to 10% MeOH/CH₂Cl₂) to give the title compound (3.48 g, 79%) as a light tan solid. MS(ESI⁺) m/z 558.4 (M+H)⁺.

E) (R)-1-((S)-3-(4-(3-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)ureido)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide To a solution of phosgene (120 μL of 20% in toluene by weight) in CH₂Cl₂ (1.5 mL) at −78° C. was added a solution of tert-butyl ((S)-1-(((S)-3-(4-aminophenyl)-1-((R)-3,3-dimethyl-5-(((R)-1,2,3,4-tetrahydronaphthalen-1-yl)carbamoyl)-1,3-azasilolidin-1-yl)-1-oxopropan-2-yl)amino)-1-oxopropan-2-yl)(methyl)carbamate (Compound G of Example 1, 54 mg, 0.09 mmol) and DIEA (50 μL) in CH₂Cl₂ (2 mL) with stirring under N₂ atm. After 30 minutes at −78° C., the mixture was concentrated in vacuo and the residue was dissolved in CH₂Cl₂ (2 mL), cooled to −30° C. and treated with a solution of tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (47 mg, 0.09 mmol) and DIEA (50 μL) in CH₂Cl₂ (2 mL). After 10 minutes, the reaction mixture was warmed to rt, stirred for 1 h, concentrated in vacuo and the residue was purified by preparative HPLC to provide the urea product as a white solid.

The urea product obtained above was mixed with CH₂Cl₂ (4 mL) and 4N HCl (1 mL) in dioxane at rt. After 1 h, the reaction mixture was concentrated in vacuo and the residue was purified by preparative HPLC to obtain the title compound as a 2 TFA salt (40 mg, 36%, white solid). MS(ESI⁺) m/z 1019.5 (M+H)⁺.

Example 3

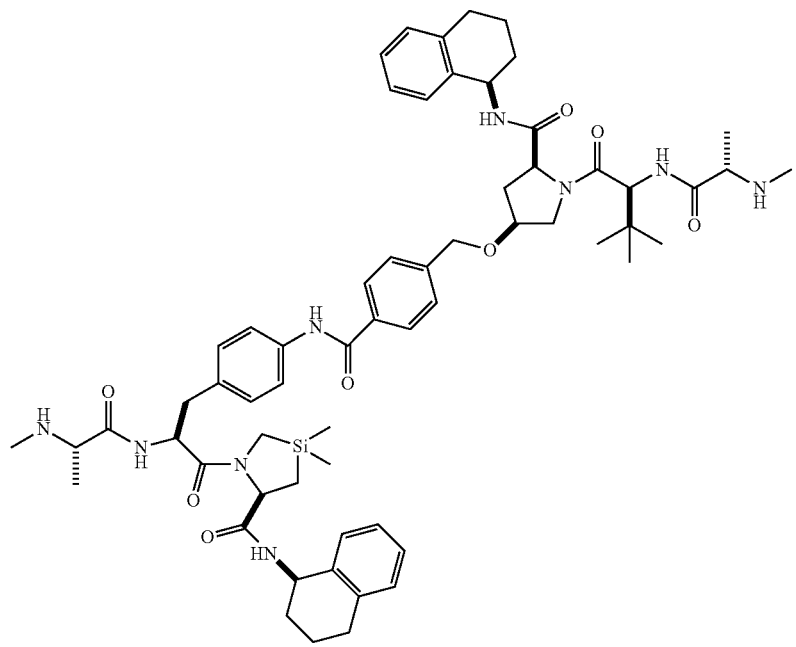

(R)-1-((S)-3-(4-(4-((((3S,5S)-1-((S)-3,3-Dimethyl-2-(S)-2-(methylamino)propanamido)butanoyl)-5-(((R)-1,2,3,4-tetrahydronaphthalen-1-yl)carbamoyl)pyrrolidin-3-yl)oxy)methyl)benzamido)phenyl)-(2-((S)-2-(methylamino)propanamido)propanoyl)-3,3-dimethyl-N—((R)-1,2,3,4-tetrahydronaphthalen-1-yl)-1,3-azasilolidine-5-carboxamide

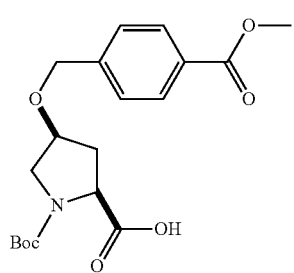

A) (2S,4S)-1-(tert-Butoxycarbonyl)-4-((4-(methoxycarbonyl)benzyl)oxy)pyrrolidine-2-carboxylic acid Sodium hydride (0.97 g, 24 mmol) was suspended in DMF (15 mL) under nitrogen at 0° C. A solution of (2S,4S)-1-(tert-butoxycarbonyl)-4-hydroxypyrrolidine-2-carboxylic acid (2.0 g, 8.7 mmol) in DMF (20 mL) was added dropwise. The reaction mixture was stirred at 0° C. for 10 min and treated with a solution of methyl 4-(bromomethyl)benzoate (2.3 g, 10 mmol) in DMF (5 mL). The reaction mixture was stirred at 0° C. for 1 h, and mixed with ethyl acetate and 1N HCl solution. The EtOAc layer was separated, washed with brine, and dried over MgSO₄. The filtrate was concentrated in vacuo and the residue was purified by flash chromatography (eluting with 20% EtOAc/DCM) to afford the title compound as a white solid (1.2 g, 37%). ¹H NMR (CDCl₃) δ 7.99 (d, J=8.1 Hz, 2H), 7.36 (d, J=3.5 Hz, 2H), 4.78-4.26 (m, 3H), 4.19-4.11 (m, 1H), 3.90 (s, 3H), 3.71-3.46 (m, 2H), 2.84-2.39 (m, 1H), 2.23-2.04 (m, 1H), 1.48 (br. s., 9H); MS(ESI⁺) m/z 324.0 (M-55)⁺.

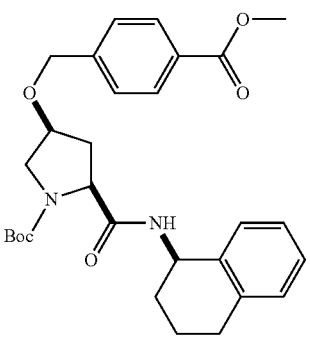

B) (2S,4S)-tert-Butyl 4-((4-(methoxycarbonyl)benzyl)oxy)-2-(((R)-1,2,3,4-tetrahydronaphthalen-1-yl)carbamoyl)pyrrolidine-1-carboxylate To a solution of (2S,4S)-1-(tert-butoxycarbonyl)-4-((4-(methoxycarbonyl)benzyl)oxy)pyrrolidine-2-carboxylic acid (1.2 g, 3.2 mmol) in DMF (10 mL) was added EDC (0.91 g, 4.7 mmol) and 3H-[1,2,3]-triazolo[4,5-b]pyridin-3-ol (0.43 g, 3.2 mmol). The reaction mixture was stirred at rt for 5 min and treated with a solution of (R)-1,2,3,4-tetrahydronaphthalen-1-amine (0.54 g, 3.6 mmol) in DMF (5 mL) and 4-methylmorpholine (0.70 mL, 6.3 mmol). The reaction mixture was stirred at rt for 1 h and diluted with ethyl acetate and brine. The organic layer was separated and washed successively with aq. NaHCO$_3$ solution, brine, and 1N HCl solution. The organics were dried over MgSO$_4$ and concentrated in vacuo. The resulting residue was purified by flash chromatography (eluting with 20% EtOAc/DCM) to afford the title compound as a white solid (1.3 g, 81%). $^1$H NMR (CDCl$_3$) δ 7.99 (d, J=8.4 Hz, 2H), 7.33 (d, J=6.8 Hz, 2H), 7.13-6.94 (m, 3H), 6.85-6.80 (m, 1H), 5.21-5.01 (m, 1H), 4.49-4.33 (m, 2H), 4.11 (d, J=3.1 Hz, 1H), 3.93 (s, 3H), 3.70-3.41 (m, 2H), 2.74 (d, J=3.3 Hz, 2H), 2.05 (s, 2H), 1.90-1.68 (m, 3H), 1.58 (s, 1H), 1.45 (s, 10H); MS(ESI$^+$) m/z 509.5 (M+H)$^+$.

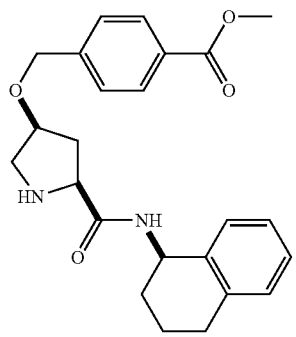

C) Methyl 4-((((3S,5S)-5-(((R)-1,2,3,4-tetrahydronaphthalen-1-yl)carbamoyl)pyrrolidin-3-yl)oxy)methyl)benzoate To a solution of (2S,4S)-tert-butyl 4-((4-(methoxycarbonyl)benzyl)oxy)-2-(((R)-1,2,3,4-tetrahydronaphthalen-1-yl)carbamoyl)pyrrolidine-1-carboxylate (1.31 g, 2.58 mmol) in DCM (10 mL) was added HCl (4.0 M solution in dioxane, 12.9 mL, 51.5 mmol). The reaction mixture was stirred at rt for 1.5 h and concentrated in vacuo to give the title compound as a HCl salt (1.15 g, 100%, white solid). $^1$H NMR (DMSO-d$_6$) δ 8.83 (d, J=8.4 Hz, 1H), 8.74 (d, J=8.6 Hz, 1H), 7.95 (d, J=8.4 Hz, 2H), 7.46 (d, J=8.4 Hz, 2H), 7.26-7.00 (m, 3H), 5.05-4.88 (m, 1H), 4.56 (q, J=12.8 Hz, 2H), 4.31 (br. s., 2H), 3.86 (s, 3H), 3.55-3.46 (m, 1.5H), 2.81-2.61 (m, 2.5H), 2.48-2.21 (m, 2H), 1.84-1.53 (m, 4H); MS(ESI$^+$) m/z 409.4 (M+H)$^+$.

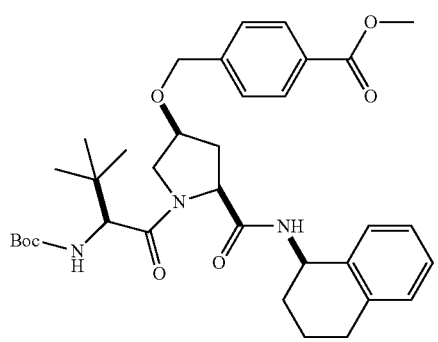

D) Methyl 4-(((((3S,5S)-1-((S)-2-((tert-butoxycarbonyl)amino)-3,3-dimethylbutanoyl)-5-(((R)-1,2,3,4-tetrahydronaphthalen-1-yl)carbamoyl)pyrrolidin-3-yl)oxy)methyl)benzoate To a solution of (S)-2-((tert-butoxycarbonyl)amino)-3,3-dimethylbutanoic acid (0.72 g, 3.1 mmol) in DMF (6 mL) were added EDC (0.74 g, 3.9 mmol) and 3H-[1,2,3]-triazolo[4,5-b]pyridin-3-ol (0.35 g, 2.58 mmol). After stirring for 5 min, a solution of methyl 4-(((((3S,5S)-5-(((R)-1,2,3,4-tetrahydronaphthalen-1-yl)carbamoyl)pyrrolidin-3-yl)oxy)methyl)benzoate, HCl (1.2 g, 2.6 mmol) in DMF (10 mL) and 4-methylmorpholine (1.1 mL, 10 mmol) were added. The resulting reaction mixture was stirred at rt for 1 h and diluted with brine and ethyl acetate. The organic layer was separated and washed successively with aq. NaHCO$_3$ solution and 1N HCl solution. The organic layer was dried over MgSO$_4$ and concentrated in vacuo. The residue was purified by flash chromatography (eluting with 20% EtOAc/DCM) to afford the title compound as a white solid (1.41 g, 88%). $^1$H NMR (CDCl$_3$) δ 8.00 (d, J=8.4 Hz, 2H), 7.39 (d, J=8.4 Hz, 2H), 7.13-6.82 (m, 4H), 5.21-4.95 (m, 2H), 4.77-4.63 (m, 2H), 4.44 (d, J=12.1 Hz, 1H), 4.28-4.11 (m, 2H), 3.91 (s, 3H), 3.70 (d, J=10.8 Hz, 1H), 2.71 (t, J=5.7 Hz, 2H), 2.14-1.72 (m, 5H), 1.41 (s, 9H), 1.10-0.92 (m, 1H), 0.78 (s, 9H); MS(ESI$^+$) m/z 622.6 (M+H)$^+$.

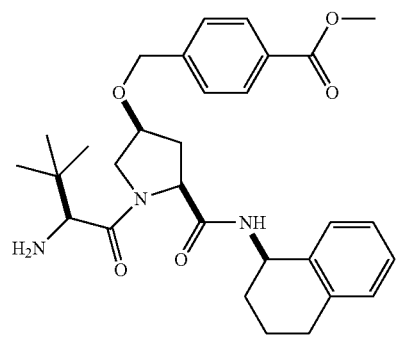

E) Methyl 4-(((((3S,5S)-1-(S)-2-amino-3,3-dimethylbutanoyl)-5-(((R)-1,2,3,4-tetrahydronaphthalen-1-yl)carbamoyl)pyrrolidin-3-yl)oxy)methyl)benzoate To a solution of methyl 4-(((((3S,5S)-1-((S)-2-((tert-butoxycarbonyl)amino)-3,3-dimethylbutanoyl)-5-(((R)-1,2,3,4-tetrahydronaphthalen-1-yl)carbamoyl)pyrrolidin-3-yl)oxy)methyl)benzoate (1.40 g, 2.25 mmol) in DCM (8 mL)

was added HCl (4.0 M solution in dioxane, 8.4 mL, 33.8 mmol). The reaction mixture was stirred at rt for 1.5 h and concentrated in vacuo to give the title compound as a HCl salt (1.26 g, 100%, white solid). $^1$H NMR (DMSO-$d_6$) δ 8.31-8.17 (m, 1H), 7.94 (d, J=8.1 Hz, 2H), 7.48 (d, J=8.1 Hz, 1.5H), 7.25 (d, J=7.5 Hz, 0.5H), 7.14-7.01 (m, 3H), 4.99-4.85 (m, 1H), 4.63 (s, 2H), 4.41 (t, J=8.0 Hz, 1H), 4.33-4.09 (m, 2H), 3.93 (d, J=5.5 Hz, 1H), 3.85 (s, 3H), 3.42 (dd, J=10.3, 6.8 Hz, 1H), 2.77-2.64 (m, 3H), 1.95-1.56 (m, 5H), 1.06 (s, 9H); MS(ESI$^+$) m/z 522.5 (M+H)$^+$.

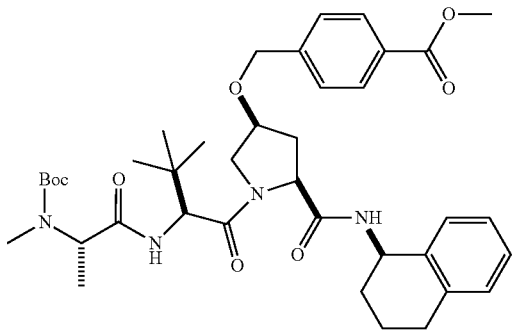

F) Methyl 4-((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoate To a solution of (S)-2-((tert-butoxycarbonyl)(methyl)amino)propanoic acid (0.53 g, 2.6 mmol) in DMF (8 mL) were added EDC (0.65 g, 3.4 mmol) and 3H-[1,2,3]-triazolo[4,5-b]pyridin-3-ol (0.31 g, 2.26 mmol). After 5 min, a solution of methyl 4-((((3S,5S)-1-((S)-2-amino-3,3-dimethylbutanoyl)-5-(((R)-1,2,3,4-tetrahydronaphthalen-1-yl)carbamoyl)pyrrolidin-3-yl)oxy)methyl)benzoate, HCl (1.26 g, 2.26 mmol) in DMF (8 mL) and 4-methylmorpholine (1.1 mL, 10.16 mmol) were added. The resulting reaction mixture was stirred at rt for 1 h and diluted with brine and ethyl acetate. The organic layer was separated and washed successively with aq. NaHCO$_3$ solution and 1N HCl solution. The organic layer was dried over MgSO$_4$ and concentrated in vacuo. The residue was purified by flash chromatography (eluting with 40% EtOAc/DCM) to afford the title compound as a white solid (1.35 g, 85%). $^1$H NMR (CDCl$_3$) δ 8.01 (d, J=8.4 Hz, 2H), 7.39 (d, J=8.4 Hz, 2H), 7.13-6.82 (m, 4H), 5.12-4.96 (m, 1H), 4.81-4.62 (m, 3H), 4.53-4.35 (m, 2H), 4.22 (dt, J=4.6, 2.2 Hz, 1H), 4.00 (dd, J=10.9, 4.7 Hz, 1H), 3.91 (s, 3H), 3.71 (d, J=11.0 Hz, 1H), 2.81-2.63 (m, 5H), 2.13-1.74 (m, 6H), 1.48 (s, 9H), 1.33-1.28 (m, 3H), 0.77 (s, 9H); MS(ESI$^+$) m/z 707.5 (M+H)$^+$.

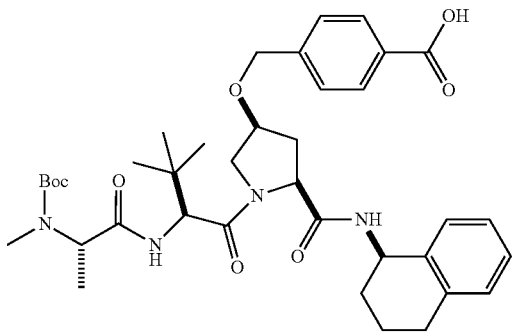

G) 4-((((3S,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoic acid To a solution of methyl 4-((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoate (1.35 g, 1.91 mmol) in THF (5 mL) and MeOH (3 mL) was added a solution of NaOH (0.31 g, 7.64 mmol) in water (6 mL). The reaction mixture was stirred at rt for 4 h, acidified with 1N HCl and extracted with ethyl acetate. The organic layer was separated, washed with brine, and dried over MgSO$_4$. The filtrate was concentrated in vacuo to give the title compound as a white solid (1.30 g, 98%). $^1$H NMR (DMSO-$d_6$) δ 8.01 (d, J=8.6 Hz, 0.5H), 7.91 (d, J=8.4 Hz, 1.5H), 7.43 (d, J=8.4 Hz, 2H), 7.24 (d, J=7.7 Hz, 1H), 7.15-6.98 (m, 3H), 4.98-4.83 (m, 1H), 4.60 (s, 2H), 4.47 (d, J=9.0 Hz, 1H), 4.34 (t, J=7.7 Hz, 1H), 4.21 (t, J=6.2 Hz, 1H), 4.12-4.05 (m, 1H), 3.86-3.71 (m, 1H), 3.54 (dd, J=10.2, 6.1 Hz, 1H), 2.81-2.65 (m, 5H), 2.45-2.36 (m, 1H), 2.02-1.92 (m, 1H), 1.86-1.56 (m, 4H), 1.40 (br. s., 9H), 1.26-1.15 (m, 3H), 1.03-0.86 (m, 9H); MS(ESI$^+$) m/z 693.6 (M+H)$^+$.

H) (R)-1-((S)-3-(4-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)oxy)methyl)benzamido)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide To a solution of 4-((((3S,5S)-1-((S)-2-((S)-2-((tert-butoxycarbonyl)(methyl)amino)propanamido)-3,3-dimethylbutanoyl)-5-((1,2,3,4-tetrahydronaphthalen-1-yl)carbamoyl)pyrrolidin-3-yl)oxy)methyl)benzoic acid (57 mg, 0.08 mmol) in DMF (2 mL) at rt was added HATU (32.9 mg, 0.09 mmol) followed by tert-butyl ((S)-1-(((S)-3-(4-aminophenyl)-1-(3,3-dimethyl-5-((1,2,3,4-tetrahydronaphthalen-1-yl)carbamoyl)-1,3-azasilolidin-1-yl)-1-oxopropan-2-yl)amino)-1-oxopropan-2-yl)(methyl)carbamate (50 mg, 0.08 mmol) and DIEA (17 μL, 0.09 mmol). The reaction mixture was stirred at rt overnight (14 h) and directly purified by preparative HPLC to afford the coupled product.

The crude coupled product obtained above was mixed with CH$_2$Cl$_2$ (7 mL) and 1.5 ml of 4N HCl in dioxane at rt. After 1 h at rt, the reaction mixture was concentrated in vacuo, mixed with water and lyophilized to obtain the title compound as a 2 HCl salt (38 mg, 39% yield, white solid). MS(ESI$^+$) m/z 1110.6 (M+H)$^+$.

Example 4

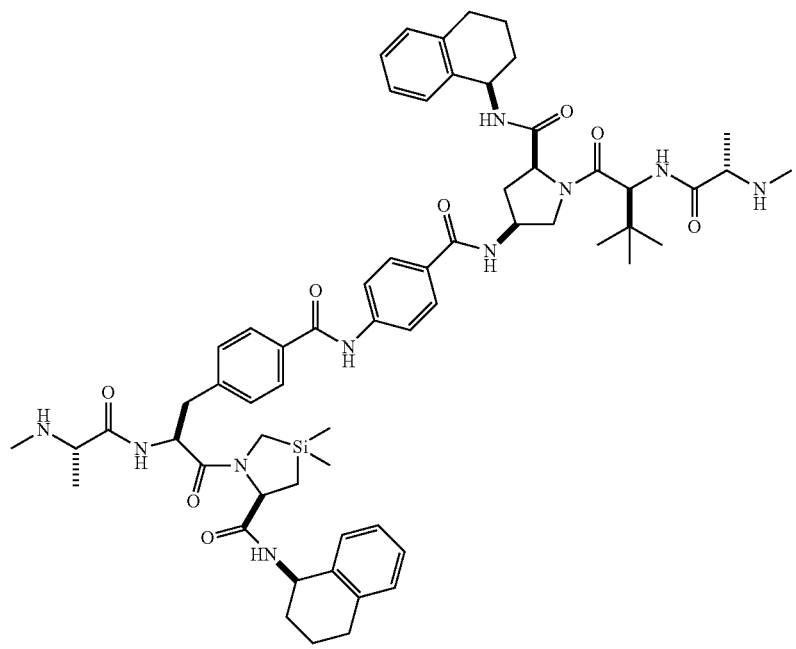

(R)-1-((S)-3-(4-((4-(((3S,5S)-1-((S)-3,3-Dimethyl-2-((S)-2-(methylamino)propanamido)butanoyl)-5-(R)-1,2,3,4-tetrahydronaphthalen-1-yl)carbamoyl)pyrrolidin-3-yl)carbamoyl)phenyl)carbamoyl)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide 6-dimethoxy-1,3,5-triazin-2-yl)-4-methylmorpholin-4-ium chloride (86 mg, 0.31 mmol) at rt followed by a solution of (R)-3,3-dimethyl-N—((R)-1,2,3,4-tetrahydronaphthalen-1-yl)-1,3-azasilolidine-5-carboxamide, TFA (105 mg, 0.261 mmol) and DIEA (115 µL) in DMF (2 mL). After 2 h, the reaction mixture was directly purified by preparative HPLC to afford the title compound (165 mg, 83% yield) as a white solid. $^1$H NMR (400 MHz, CDCl$_3$) δ 7.90 (d, J=8.1 Hz, 2H), 7.75 (d, J=7.5 Hz, 2H), 7.52 (t, J=6.7 Hz, 2H), 7.39-7.06 (m, 10H), 6.51 (d, J=8.4 Hz, 1H), 5.76 (d, J=8.8 Hz, 1H), 5.18-5.00 (m, 3H), 4.38-4.30 (m, 1H), 4.25-4.10 (m, 1H), 3.18 (d, J=13.4 Hz, 1H), 3.08-3.00 (m, 1H), 2.85-2.71 (m, 4H), 2.10-2.02 (m, 1H), 1.91-1.81 (m, 3H), 1.56 (s, 9H), 1.33 (dd, J=14.9, 1.7 Hz, 1H), 1.06 (dd, J=14.7, 10.1 Hz, 1H), 0.46 (s, 3H), 0.29 (s, 3H); MS(ESI$^+$) m/z 758.2 (M+H)$^+$.

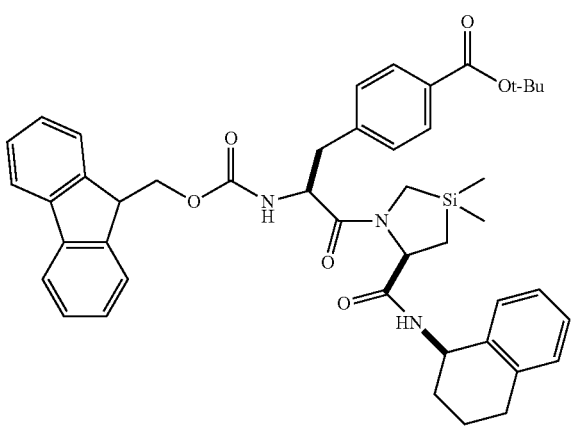

A) tert-Butyl 4-((S)-2-((((9H-fluoren-9-yl)methoxy)carbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)benzoate To a solution of (S)-2-((((9H-fluoren-9-yl)methoxy)carbonyl)amino)-3-(4-(tert-butoxycarbonyl)phenyl)propanoic acid (0.14 g, 0.29 mmol) in DMF (1.5 mL) was added 4-(4,

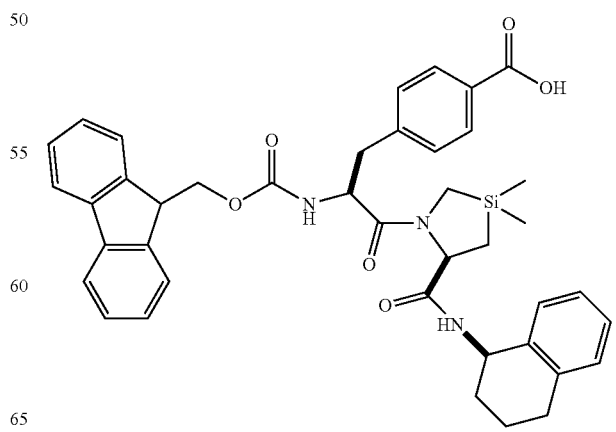

B) 4-((S)-2-((((9H-Fluoren-9-yl)methoxy)carbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)benzoic acid To a solution of tert-butyl 4-((S)-2-((((9H-fluoren-9-yl)methoxy)carbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)benzoate (0.17 g, 0.22 mmol) in CH$_2$Cl$_2$ (10 mL) was added TFA (1 mL) at rt. After 4 h, the reaction mixture was concentrated in vacuo to obtain the title compound (150 mg, 82% yield) as a white solid. $^1$H NMR (400 MHz, CDCl$_3$) δ 12.37 (br. s., 1H), 8.05 (d, J=8.4 Hz, 2H), 7.76 (d, J=7.5 Hz, 2H), 7.56 (dd, J=7.3, 4.4 Hz, 2H), 7.44-7.05 (m, 11H), 6.62-6.52 (m, 2H), 5.23-5.09 (m, 2H), 4.94 (t, J=6.9 Hz, 1H), 4.38-4.11 (m, 3H), 3.33 (d, J=13.2 Hz, 1H), 3.20 (dd, J=14.1, 4.8 Hz, 1H), 3.03-2.93 (m, 2H), 2.86-2.74 (m, 2H), 2.11-2.01 (m, 1H), 1.92-1.79 (m, 3H), 1.27 (d, J=6.6 Hz, 2H), 0.45 (s, 3H), 0.32 (s, 3H); MS(ESI$^+$) m/z 702.1 (M+H)$^+$.

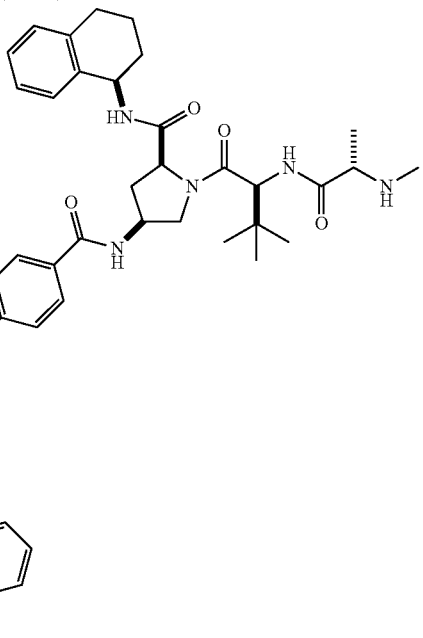

C) tert-Butyl ((S)-1-(((S)-1-((2S,4S)-4-(4-(4-((S)-2-((((9H-fluoren-9-yl)methoxy)carbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)benzamido)benzamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-(((S)-1-((2S,4S)-4-(4-aminobenzamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (62 mg, 0.09 mmol) in DMF (2 mL) at rt was added HATU (38.3 mg, 0.101 mmol) followed by a solution of 44-(S)-2-((((9H-fluoren-9-yl)methoxy)carbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)benzoic acid (64 mg, 0.09 mmol) and DIEA (30 µL) in DMF (2 mL). The reaction mixture was stirred at rt overnight and heated at 60° C. for 7 h. An additional 30 mg of HATU was added and the resulting mixture was stirred at rt over the weekend, then heated at 60° C. for 3 h. The reaction mixture was directly purified by preparative HPLC to afford the title compound (22 mg) as a glassy material. MS(ESI$^+$) m/z 1362.0 (M+H)$^+$.

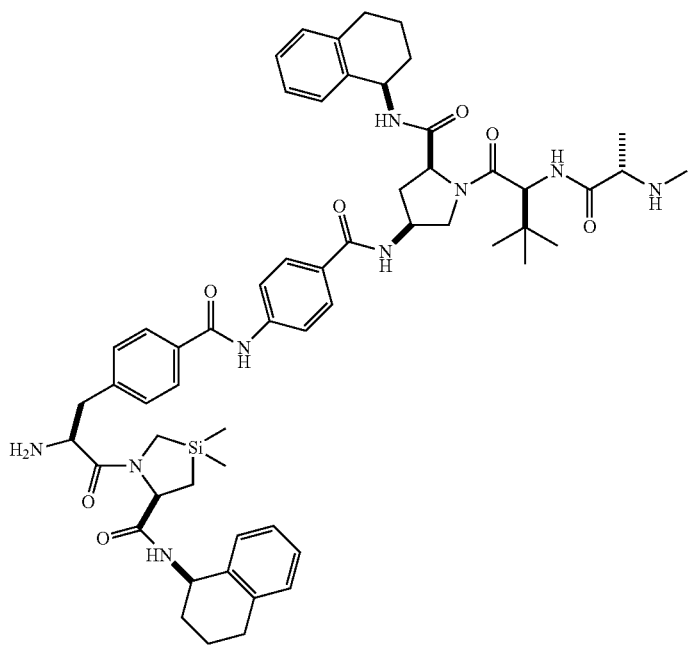

D) tert-Butyl ((S)-1-(((S)-1-((2S,4S)-4-(4-(4-((S)-2-amino-3-((R)-3,3-dimethyl-5-(((R)-1,2,3,4-tetrahydronaphthalen-1-yl)carbamoyl)-1,3-azasilolidin-1-yl)-3-oxopropyl)benzamido)benzamido)-2-((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-((S)-1-(((S)-1-((2S,4S)-4-(4-(4-((S)-2-(((9H-fluoren-9-yl)methoxy)carbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)benzamido)benzamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (22 mg) in CH$_2$Cl$_2$ (4 mL) was added piperidine (200 μL) at rt. After 1 h at rt, the reaction mixture was concentrated in vacuo and the resulting residue purified by preparative HPLC to afford the title compound as a TFA salt (20 mg, 100% yield, white solid). MS(ESI$^+$) m/z 1139.8 (M+H)$^+$.

E) (R)-1-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenyl)carbamoyl)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide To a solution of (S)-2-((tert-butoxycarbonyl)(methyl)amino)propanoic acid (3.3 mg, 0.016 mmol) in DMF (1 mL) at rt was added HATU (6.7 mg, 0.018 mmol) followed by a solution of tert-butyl ((S)-1-(((S)-1-((2S,4S)-4-(4-(4-((S)-2-amino-3-((R)-3,3-dimethyl-5-(((R)-1,2,3,4-tetrahydronaphthalen-1-yl)carbamoyl)-1,3-azasilolidin-1-yl)-3-oxopropyl)benzamido)benzamido)-2-((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate TFA salt (20 mg, 0.016 mmol) and DIEA (10 μL) in DMF (1.8 mL). After 1 h at rt, the reaction mixture was directly purified by preparative HPLC to afford the coupled product (21 mg) as a glassy material. MS(ESI$^+$) m/z 1324.3 (M+H)$^+$.

The coupled product obtained above was mixed with CH$_2$Cl$_2$ (4 mL) and 4N HCl in dioxane (1 mL) at rt. After 1 h, the mixture was concentrated in vacuo, and the resulting residue was mixed with water and lyophilized to obtain the title compound as a 2 HCl salt (14 mg, 70% yield, white solid). MS(ESI$^+$) m/z 1124.2 (M+H)$^+$.

Example 5

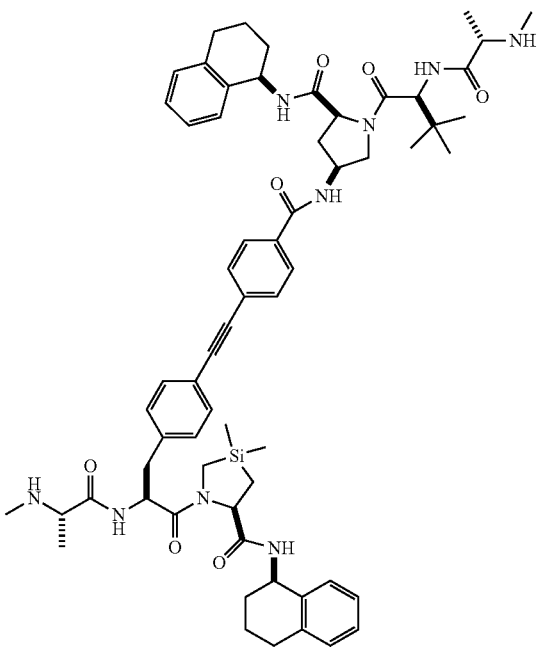

(R)-1-((S)-3-(4-((4-(((3S,5S)-1-((S)-3,3-Dimethyl-2-
((S)-2-(methylamino)propanamido)butanoyl)-5-
(((R)-1,2,3,4-tetrahydronaphthalen-1-yl)carbamoyl)
pyrrolidin-3-yl)carbamoyl)phenyl)ethynyl)phenyl)-
2-((S)-2-(methylamino)propanamido)propanoyl)-3,
3-dimethyl-N—((R)-1,2,3,4-tetrahydronaphthalen-1-
yl)-1,3-azasilolidine-5-carboxamide

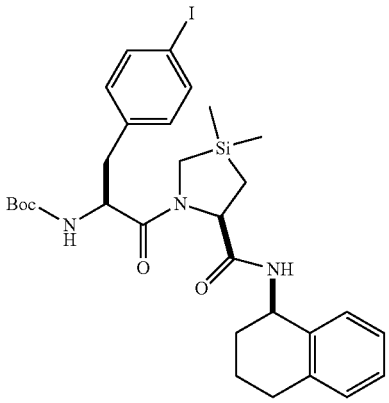

A) tert-Butyl ((S)-1-((R)-3,3-dimethyl-5-(((R)-1,2,3,
4-tetrahydronaphthalen-1-yl)carbamoyl)-1,3-azasilo-
lidin-1-yl)-3-(4-iodophenyl)-1-oxopropan-2-yl)car-
bamate To a solution of (S)-2-((tert-butoxycarbonyl)amino)-3-(4-iodophenyl)propanoic acid (0.77 g, 2.0 mmol) in DMF (4 mL) was added EDC (0.53 g, 2.8 mmol) at 0° C. The reaction mixture was stirred at 0° C. for 5 min, followed by addition of 3H-[1,2,3]-triazolo[4,5-b]pyridin-3-ol (0.22 g, 1.6 mmol) and a solution of (R)-3,3-dimethyl-N—((R)-1,2,3,4-tetrahydronaphthalen-1-yl)-1,3-azasilolidine-5-carboxamide HCl (0.53 g, 1.6 mmol) in DMF (3 mL) and DIEA (0.8 mL, 4.6 mmol). The resulting mixture was then stirred at rt for 1 h and diluted with ethyl acetate and brine. The organic layer was separated, washed with aq. NaHCO₃ solution, dried over MgSO₄ and concentrated in vacuo. The resulting oil was purified by flash chromatography (eluting with 20% EtOAc/DCM) to afford the title compound as a white solid (0.94 g, 87%). ¹H NMR (CDCl₃) δ 7.76-7.45 (m, 2H), 7.22-7.05 (m, 3.5H), 6.89 (d, J=8.1 Hz, 2H), 6.50 (d, J=8.1 Hz, 0.5H), 5.27-5.06 (m, 3H), 4.96-4.71 (m, 1H), 3.10 (d, J=13.4 Hz, 0.5H), 2.96-2.45 (m, 4.5H), 2.16-1.98 (m, 1H), 1.85 (dd, J=11.3, 5.8 Hz, 3H), 1.44-1.16 (m, 10H), 0.98 (dd, J=14.7, 10.1 Hz, 1H), 0.44 (s, 3H), 0.27 (s, 3H); MS(ESI⁺) m/z 662.4 (M+H)⁺.

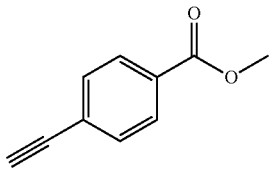

B) Methyl 4-ethynylbenzoate

To a solution of methyl 4-iodobenzoate (1.5 g, 5.72 mmol) and trimethylsilylacetylene (Aldrich, 1.58 mL, 11.45 mmol) in toluene (12 mL) were added Pd(PPh₃)₄ (0.66 g, 0.57 mmol), CuI (0.16 g, 0.86 mmol), and TEA (6.4 mL, 45.80 mmol). The resulting reaction mixture was purged with nitrogen for 3 min and stirred at rt for 3 h. The reaction mixture was diluted with ethyl acetate and NH₄Cl solution. The organic layer was separated, washed with brine, dried over MgSO₄ and concentrated in vacuo. The residue was purified by flash column chromatography (eluting with 10% EtOAc/hexane) to afford the title compound as a white solid (1.35 g, 96%). ¹H NMR (CDCl₃) δ 7.98 (d, J=8.6 Hz, 2H), 7.53 (d, J=8.6 Hz, 2H), 3.92 (s, 3H), 0.27 (s, 9H); MS(ESI⁺) m/z 233.1 (M+H)⁺.

To a solution of methyl 4-((trimethylsilyl)ethynyl)benzoate (1.35 g, 5.35 mmol) in THF (10 mL) was added TBAF (1 M solution in THF, 10.7 mL, 10.70 mmol). The resulting brown reaction mixture was stirred at rt for 3 h and concentrated in vacuo. The residue was purified by flash column chromatography (eluting with 5% EtOAc/hexane) to afford the title compound as a white solid (0.65 g, 76%). ¹H NMR (CDCl₃) δ 8.00 (d, J=8.6 Hz, 2H), 7.56 (d, J=8.6 Hz, 2H), 3.93 (s, 3H), 3.23 (s, 1H).

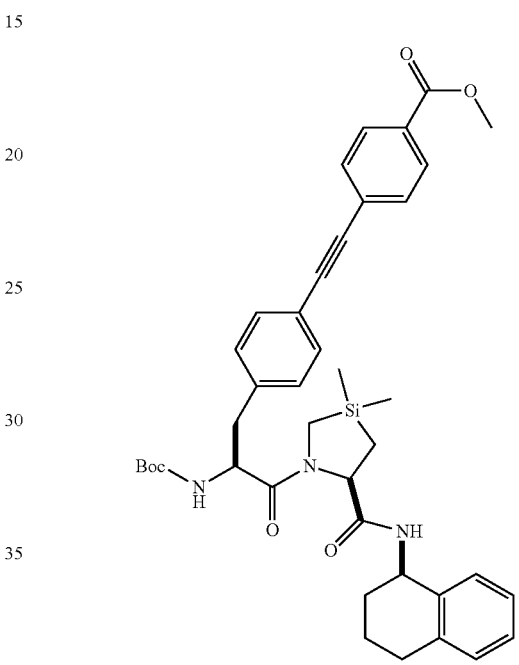

C) Methyl 4-((4-((S)-2-((tert-butoxycarbonyl)
amino)-3-((R)-3,3-dimethyl-5-(((R)-1,2,3,4-tetrahy-
dronaphthalen-1-yl)carbamoyl)-1,3-azasilolidin-1-
yl)-3-oxopropyl)phenyl)ethynyl)benzoate To a solution of tert-butyl ((S)-1-((R)-3,3-dimethyl-5-((R)-1,2,3,4-tetrahydronaphthalen-1-yl)carbamoyl)-1,3-azasilolidin-1-yl)-3-(4-iodophenyl)-1-oxopropan-2-yl)carbamate (90 mg, 0.14 mmol) in toluene (6 mL) were added methyl 4-ethynylbenzoate (33 mg, 0.20 mmol) and copper(I) iodide (5 mg, 0.027 mmol). The resulting suspension was purged with nitrogen stream for 3 min and treated with Pd(PPh₃)₄ (24 mg, 0.020 mmol) and TEA (0.15 mL, 1.09 mmol). The reaction mixture was stirred at rt for 3 h and diluted with ethyl acetate and brine. The organic layer was separated, washed with saturated aq. NH₄Cl solution, dried over MgSO₄ and concentrated in vacuo. The residue was purified by flash column chromatography (eluting with 15% EtOAc/DCM) to afford the title compound as a light yellow solid (91 mg, 96%). ¹H NMR (CDCl₃) δ 8.23-7.82 (m, 2H), 7.56 (d, J=8.4 Hz, 2H), 7.40 (d, J=8.1 Hz, 2H), 7.25-7.04 (m, 5.5H), 6.56 (d, J=8.4 Hz, 0.5H), 5.36-4.80 (m, 3.5H), 4.12 (q, J=7.3 Hz, 0.5H), 3.92 (s, 3H), 3.27-2.48 (m, 5H), 2.15-1.96 (m, 1H), 1.95-1.62 (m, 3H), 1.45-1.15 (m, 10.5H), 0.98 (dd, J=14.7, 10.1 Hz, 0.5H), 0.59-0.16 (m, 6H); MS(ESI⁺) m/z 694.5 (M+H)⁺.

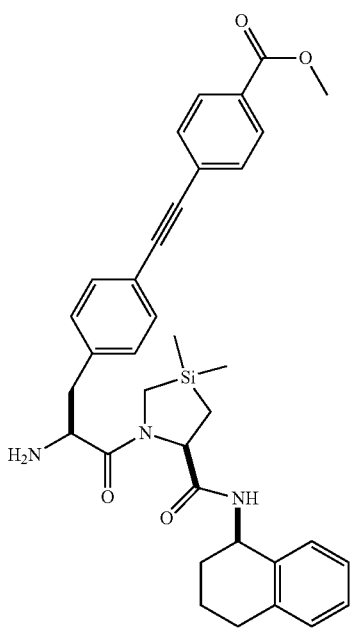

D) Methyl 4-((4-((S)-2-amino-3-((R)-3,3-dimethyl-5-(((R)-1,2,3,4-tetrahydronaphthalen-1-yl)carbamoyl)-1,3-azasilolidin-1-yl)-3-oxopropyl)phenyl)ethynyl)benzoate To a solution of methyl 4-((4-((S)-2-((tert-butoxycarbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)phenyl)ethynyl)benzoate (92 mg, 0.13 mmol) in DCM (2 mL) was added HCl (4.0 M solution in dioxane, 0.5 mL, 2.00 mmol). The reaction mixture was stirred at rt for 4 h and concentrated in vacuo to give the title compound as a HCl salt (80 mg, 95%, brown solid). MS(ESI⁺) m/z 594.5 (M+H)⁺.

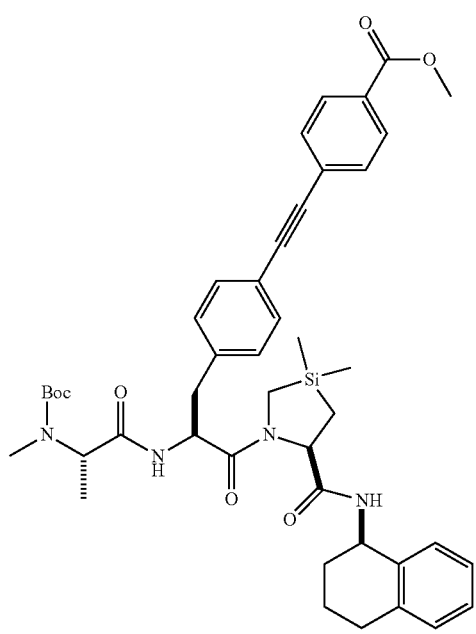

E) Methyl 4-((4-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)ethynyl)benzoate To a solution of (S)-2-((tert-butoxycarbonyl)(methyl)amino)propanoic acid (34 mg, 0.17 mmol) in DMF (2 mL) were added EDC (41 mg, 0.22 mmol) and 3H-[1,2,3]-triazolo[4,5-b]pyridin-3-ol (17 mg, 0.13 mmol), followed by a solution of methyl 4-((4-((S)-2-amino-3-((R)-3,3-dimethyl-5-(((R)-1,2,3,4-tetrahydronaphthalen-1-yl)carbamoyl)-1,3-azasilolidin-1-yl)-3-oxopropyl)phenyl)ethynyl)benzoate HCl salt (80 mg, 0.13 mmol) in DMF (2 mL) and DIEA (0.07 mL, 0.38 mmol). The reaction mixture was stirred at rt for 1 h and diluted with ethyl acetate and brine. The organic layer was separated, washed with brine, dried over MgSO₄ and concentrated in vacuo to give the title compound as a yellow solid (85 mg, 86%). ¹H NMR (CDCl₃) δ 8.10-7.91 (m, 2H), 7.63-7.50 (m, 2H), 7.40 (d, J=8.1 Hz, 2H), 7.24-7.00 (m, 5.5H), 6.56 (d, J=8.6 Hz, 0.5H), 5.26-5.06 (m, 2.5H), 4.11 (q, J=7.0 Hz, 0.5H), 3.92 (s, 3H), 3.21-2.55 (m, 6H), 2.49 (s, 3H), 2.14-1.70 (m, 5H), 1.47 (s, 9H), 1.31-0.90 (m, 5H), 0.52-0.19 (m, 6H); MS(ESI⁺) m/z 779.6 (M+H)⁺.

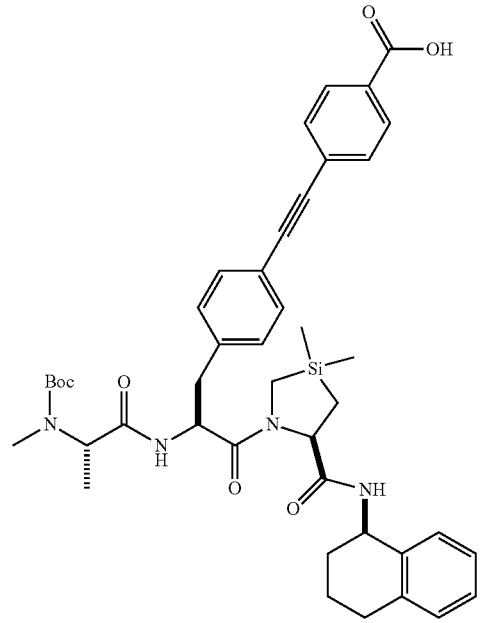

F) 4-((4-((S)-2-((S)-2-((tert-Butoxycarbonyl)(methyl)amino)propanamido)-3-((R)-3,3-dimethyl-5-((R)-1,2,3,4-tetrahydronaphthalen-1-yl)carbamoyl)-1,3-azasilolidin-1-yl)-3-oxopropyl)phenyl)ethynyl)benzoic acid To a solution of crude methyl 4-((4-((S)-2-((S)-2-((tert-butoxycarbonyl)(methyl)amino)propanamido)-3-(R)-3,3-dimethyl-5-((R)-1,2,3,4-tetrahydronaphthalen-1-yl)carbamoyl)-1,3-azasilolidin-1-yl)-3-oxopropyl)phenyl)ethynyl)benzoate (85 mg, 0.11 mmol) in THF (2 mL) and MeOH (2 mL) was added LiOH solution (1.1 mL, 2.2 mmol). The resulting mixture was stirred at rt overnight and then treated with 1N HCl solution to adjust its pH to 1. The resulting suspension was extracted with ethyl acetate (2×). The organic layer was separated, dried over MgSO₄ and concentrated in vacuo. The residue was purified by preparative HPLC to provide the title compound as a white solid (24 mg, 28%). MS(ESI⁺) m/z 765.5 (M+H)⁺.

G) (R)-1-((S)-3-(4-((4-(((3S,5S)-1-((S)-3,3-Dimethyl-2-((S)-2-(methylamino)propanamido)butanoyl)-5-((R)-1,2,3,4-tetrahydronaphthalen-1-yl)carbamoyl)pyrrolidin-3-yl)carbamoyl)phenyl)ethynyl)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide To a solution of 4-((4-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)phenyl)ethynyl)benzoic acid (60 mg, 0.08 mmol) in DMF (2 mL) was added EDC (27 mg, 0.14 mmol) with stirring. After 3 min, 3H[1,2,3]-triazolo[4,5-b]pyridin-3-ol (11 mg, 0.08 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (53 mg, 0.09 mmol) and DIEA (0.03 mL, 0.16 mmol) were added. The reaction mixture was stirred at rt for 3 h and diluted with ethyl acetate and brine. The organic layer was separated and concentrated in vacuo. The residue was purified by flash column chromatography (eluting with 60% EtOAc/DCM) to afford the coupling product.

To a solution of the crude coupling product (16 mg, 0.01 mmol) in DCM (1.5 mL) was added TFA (0.3 mL, 3.89 mmol). The reaction mixture was stirred at rt for 40 min and concentrated in vacuo. The residue was purified by preparative HPLC to provide the title compound as a 2TFA salt (13 mg, 11%, white solid). MS(ESI⁺) m/z 1105.8 (M+H)⁺.

Example 6

(R)-1-((S)-3-(4-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenethyl)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide A mixture of 4-((4-((S)-2-((S)-2-((tert-butoxycarbonyl)(methyl)amino)propanamido)-3-(R)-3,3-dimethyl-5-((R)-1,2,3,4-tetrahydronaphthalen-1-yl)carbamoyl)-1,3-azasilolidin-1-yl)-3-oxopropyl)phenyl)ethynyl)benzoic acid (30 mg, 0.023 mmol) and 10% Pd-C (6 mg, 0.011 mmol) in MeOH (2 mL) was stirred under 1 atm of H₂ gas for 3 h. The reaction mixture was filtered through a CELITE® pad and the filtrate was concentrated in vacuo. The reduced product (25 mg, 0.019 mmol) was mixed with DCM (1.0 mL) and TFA (0.2 mL, 2.6 mmol) at rt. The reaction mixture was stirred for 1 h, concentrated in vacuo and the residue was purified by preparative HPLC to give the title compound as a white solid after lyophilization (19 mg, 60%). MS(ESI⁺) m/z 1108.8 (M+H)⁺.

Example 7

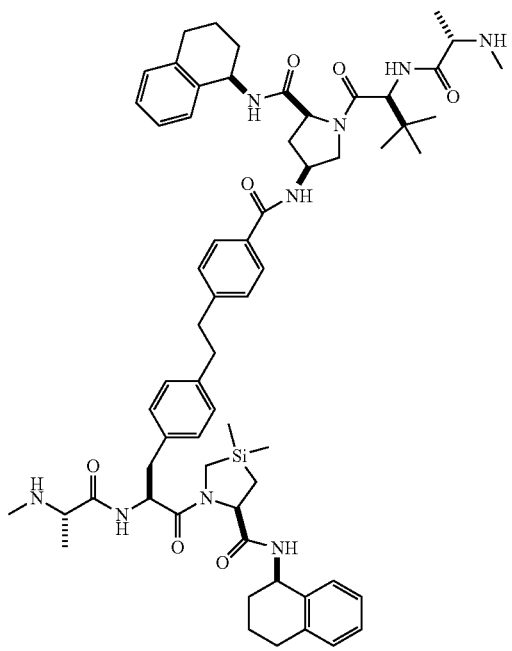

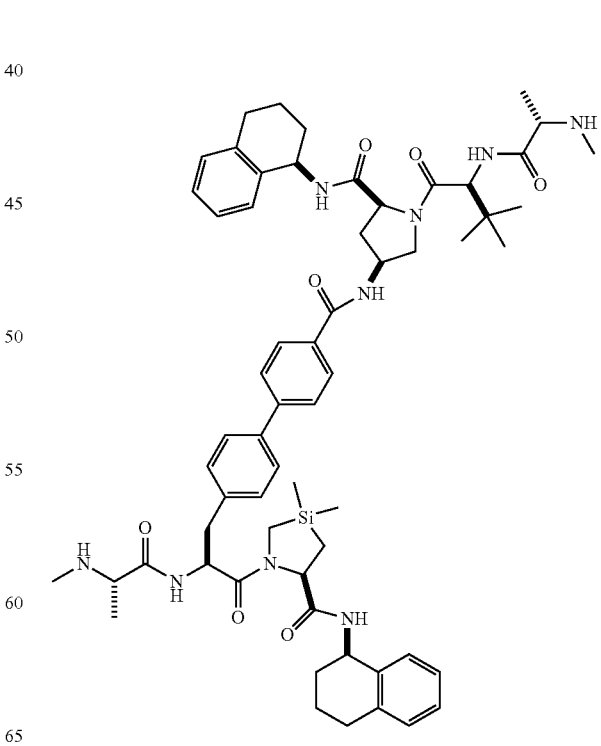

(R)-1-((S)-3-(4'-(((3S,5S)-1-((S)-3,3-Dimethyl-2-((S)-2-(methylamino)propanamido)butanoyl)-5-((R)-1,2,3,4-tetrahydronaphthalen-1-yl)carbamoyl)pyrrolidin-3-yl)carbamoyl)-[1,1'-biphenyl]-4-yl)-2-((S)-2-(methylamino)propanamido)propanoyl)-3,3-dimethyl-N—(R)-1,2,3,4-tetrahydronaphthalen-1-yl)-1,3-azasilolidine-5-carboxamide

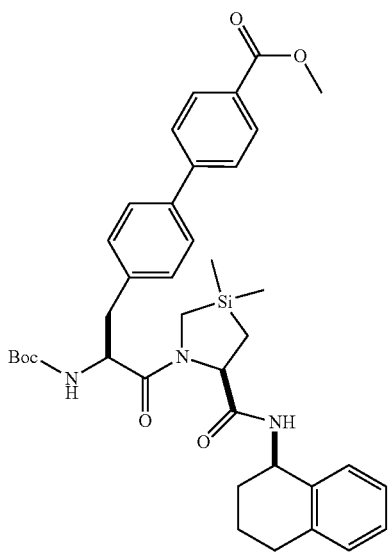

A) Methyl 4'-((S)-2-((tert-butoxycarbonyl)amino)-3-(R)-3,3-dimethyl-5-((R)-1,2,3,4-tetrahydronaphthalen-1-yl)carbamoyl)-1,3-azasilolidin-1-yl)-3-oxopropyl)-[1,1'-biphenyl]-4-carboxylate To a solution of tert-butyl ((S)-1-(R)-3,3-dimethyl-5-((R)-1,2,3,4-tetrahydronaphthalen-1-yl)carbamoyl)-1,3-azasilolidin-1-yl)-3-(4-iodophenyl)-1-oxopropan-2-yl)carbamate (Compound A of Example 5, 90 mg, 0.14 mmol) in toluene (6 mL) were added (4-(methoxycarbonyl)phenyl)boronic acid (49 mg, 0.27 mmol) and K₂CO₃ (38 mg, 0.27 mmol). The resulting suspension was purged with nitrogen for 3 min and treated with Pd(PPh₃)₄ (24 mg, 0.02 mmol). The resulting reaction mixture was stirred at 80° C. for 3 h, and eventually turned brown. Additional (4-(methoxycarbonyl)phenyl)boronic acid (49.0 mg, 0.272 mmol), K₂CO₃ (38 mg, 0.27 mmol), water (1 mL) and Pd(PPh₃)₄ (24 mg, 0.020 mmol) were then added. The reaction mixture was purged with N₂ and stirred at 80° C. for 2 h then at rt overnight. The reaction mixture was diluted with ethyl acetate and brine. The organic layer was separated, washed with brine and dried over MgSO₄. The filtrate was concentrated in vacuo and the residue was purified by flash column chromatography (eluting with 30% EtOAc/hexane) to afford the title compound as a light yellow solid (30 mg, 33%). $^1$H NMR (CDCl₃) δ 8.34 (d, J=8.1 Hz, 1H), 8.21 (d, J=8.1 Hz, 1H), 8.13-8.02 (m, 2H), 7.94-7.82 (m, 1H), 7.69-7.57 (m, 2H), 7.51 (d, J=8.1 Hz, 1H), 7.34-7.28 (m, 1H), 7.18-7.03 (m, 2.5H), 6.60 (d, J=8.1 Hz, 0.5H), 5.40-5.27 (m, 1H), 5.16-4.91 (m, 2H), 4.06-3.90 (m, 3H), 3.22-2.94 (m, 2H), 2.89-2.66 (m, 3H), 1.94-1.77 (m, 3H), 1.50-1.19 (m, 11H), 1.13-0.90 (m, 2H), 0.51-0.26 (m, 6H); MS(ESI⁻) m/z 670.5 (M+H)⁻.

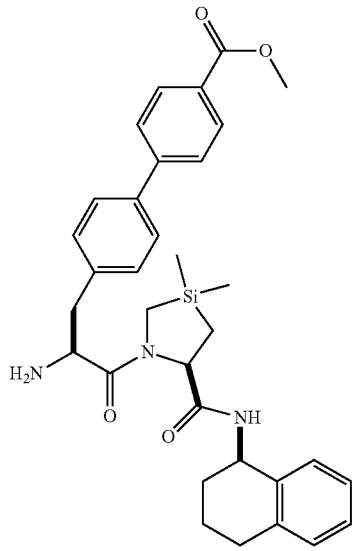

B) Methyl 4'-((S)-2-amino-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylate To a solution of methyl 4'-((S)-2-((tert-butoxycarbonyl)amino)-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylate (30 mg, 0.045 mmol) in DCM (2 mL) was added HCl (4.0 M solution in dioxane) (0.34 mL, 1.34 mmol). The reaction mixture was stirred at rt for 3 h. The reaction mixture was concentrated in vacuo to give the title compound HCl salt as a light yellow solid (25 mg, 92%). MS(ESI⁺) m/z 570.5 (M+H)⁺.

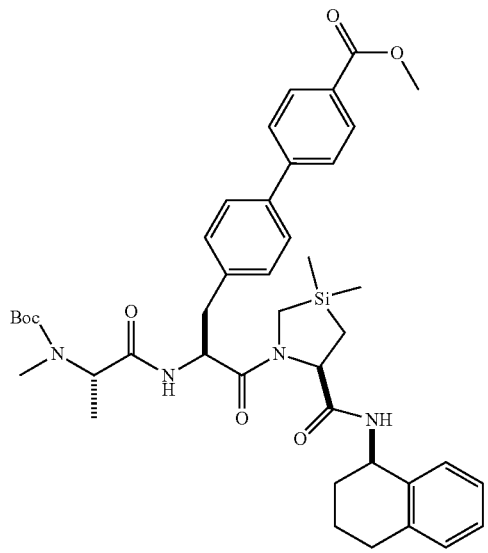

C) Methyl 4'-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylate To a solution of (S)-2-((tert-butoxycarbonyl)(methyl)amino)propanoic acid (11 mg, 0.054 mmol) in DMF (1 mL) were added EDC (14 mg, 0.074 mmol) and 3H-[1,2,3]-triazolo[4,5-b]pyridin-3-ol (6 mg, 0.04 mmol). After 5 min, a solution of methyl 4'-((S)-2-amino-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylate, HCl (25 mg, 0.041 mmol) in DMF (1 mL) and DIEA (0.02 mL, 0.12 mmol) were added. The resulting mixture was stirred at rt for 1 h and diluted with ethyl acetate and brine. The organic layer was separated, washed with aq. NaHCO$_3$ solution and dried over MgSO$_4$. The filtrate was concentrated in vacuo and the residue was purified by flash column chromatography (eluting with 35% EtOAc/DCM) to afford the title compound as a white solid (20 mg, 64%). $^1$H NMR (CDCl$_3$) δ 8.12-7.98 (m, 3H), 7.64-7.43 (m, 4H), 7.25-7.17 (m, 2H), 7.13-7.03 (m, 2.5H), 6.59 (d, J=8.6 Hz, 0.5H), 5.25 (td, J=8.4, 5.1 Hz, 1H), 5.13 (d, J=8.4 Hz, 2H), 3.94 (s, 3H), 3.07-2.98 (m, 2H), 2.83-2.61 (m, 5H), 2.10-1.97 (m, 1H), 1.90-1.79 (m, 3H), 1.51-1.42 (m, 11H), 1.31-1.13 (m, 5H), 1.03-0.93 (m, 1H), 0.49-0.21 (m, 6H); MS(ESI$^+$) m/z 755.6 (M+H)$^+$.

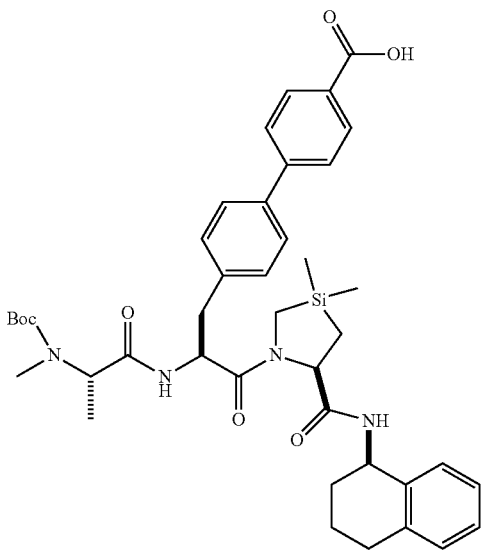

D) 4'-((S)-2-((S)-2-((tert-Butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylic acid To a solution of methyl 4'-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylate (40 mg, 0.053 mmol) in THF (1 mL) and MeOH (0.5 mL) was added LiOH solution (0.48 mL, 0.95 mmol). The resulting mixture was stirred at rt overnight and acidified (1N HCl) to pH 1. The resulting mixture was extracted with ethyl acetate (2x). The organic layer was separated, dried over MgSO$_4$ and concentrated in vacuo to give the title compound. MS(ESI$^+$) m/z 741.5 (M+H)$^+$.

E) (R)-1-((S)-3-(4'-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)-[1,1'-biphenyl]-4-yl)-2-((S)-2-(methylamino)propanoyl)-3,3-dimethyl-N—((R)-1,2,3,4-tetrahydronaphthalen-1-yl)-1,3-azasilolidine-5-carboxamide To a solution of the crude 4'-((S)-2-((S)-2-((tert-butoxycarbonyl)(methyl)amino)propanamido)-3-((R)-3,3-dimethyl-5-(((R)-1,2,3,4-tetrahydronaphthalen-1-yl)carbamoyl)-1,3-azasilolidin-1-yl)-3-oxopropyl)-[1,1'-biphenyl]-4-carboxylic acid (40 mg, 0.054 mmol) in DMF (1 mL) was added EDC (19 mg, 0.097 mmol). After 3 min, 3H-[1,2,3]-triazolo[4,5-b]pyridin-3-ol (7 mg, 0.054 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (36 mg, 0.065 mmol) and DIEA (0.02 mL, 0.11 mmol) were added. The reaction mixture was stirred at rt for 18 h and diluted with ethyl acetate and brine. The organic layer was separated and concentrated in vacuo.

To the crude residue mixture (20 mg, 0.016 mmol) in DCM (1.5 mL) was added TFA (0.3 mL, 3.89 mmol). The reaction mixture was stirred at rt for 40 min and concentrated in vacuo. The resulting residue was purified by preparative HPLC to provide the title compound as a 2TFA salt (11 mg, 14%, white solid). MS(ESI$^+$) m/z 1080.8 (M+H)$^+$.

Example 8

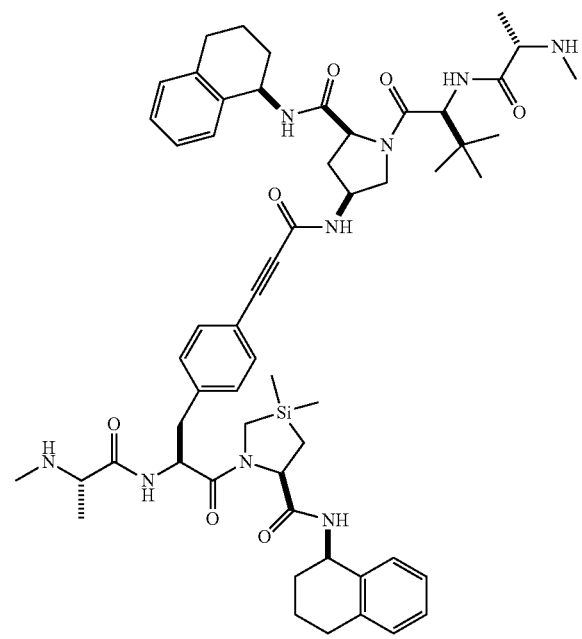

(R)-1-((S)-3-(4-(3-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)amino)-3-oxoprop-1-yn-1-yl)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide

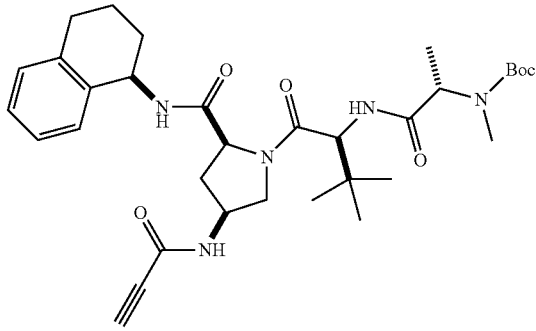

A) tert-Butyl ((S)-1-(((S)-3,3-dimethyl-1-oxo-1-((2S,4S)-4-propiolamido-2-(((R)-1,2,3,4-tetrahydronaphthalen-1-yl)carbamoyl)pyrrolidin-1-yl)butan-2-yl)amino)-1-oxopropan-2-yl)(methyl)carbamate To a solution of propiolic acid (0.06 mL, 0.90 mmol) in DMF (2 mL) at 0° C. was added HATU (123 mg, 0.32 mmol) followed by tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (100 mg, 0.18 mmol) and DIEA (0.06 mL, 0.36 mmol). The reaction mixture was stirred at rt for 1 h and diluted with ethyl acetate and brine. The organic layer was separated, washed with aq. NaHCO₃ solution, dried over MgSO₄ and concentrated in vacuo. The residue was purified by flash column chromatography (eluting with 90% EtOAc/hexane) to afford the title compound as a white solid (76 mg, 70%). ¹H NMR (CDCl₃) δ 8.60 (d, J=6.6 Hz, 1H), 7.85 (d, J=8.6 Hz, 1H), 7.25 (m, 1H), 7.16-6.98 (m, 3H), 5.23-5.08 (m, 1H), 4.73 (d, J=8.8 Hz, 1H), 4.63-4.48 (m, 1H), 4.32 (d, J=8.6 Hz, 1H), 3.96 (dd, J=10.9, 5.0 Hz, 1H), 3.75 (d, J=11.0 Hz, 1H), 2.80-2.70 (m, 5H), 2.43 (d, J=13.9 Hz, 1H), 2.18 (ddd, J=14.0, 8.9, 6.4 Hz, 1H), 2.06-1.94 (m, 1H), 1.91-1.80 (m, 4H), 1.46 (s, 10H), 1.30-1.25 (m, 3H), 0.76 (s, 9H); MS(ESI⁺) m/z 610.4 (M+H)⁺.

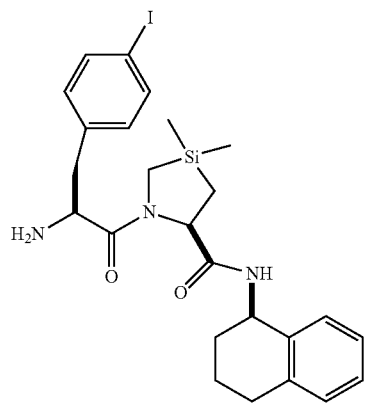

B) (R)-1-((S)-2-Amino-3-(4-iodophenyl)propanoyl)-3,3-dimethyl-N—(R)-1,2,3,4-tetrahydronaphthalen-1-yl)-1,3-azasilolidine-5-carboxamide To a solution of tert-butyl ((S)-1-(R)-3,3-dimethyl-5-((R)-1,2,3,4-tetrahydronaphthalen-1-yl)carbamoyl)-1,3-azasiloli-din-1-yl)-3-(4-iodophenyl)-1-oxopropan-2-yl)carbamate (0.64 g, 0.97 mmol) in DCM (6 mL) was added HCl (4.0 M solution in dioxane, 5 mL, 20 mmol). The reaction mixture was stirred at rt for 1.5 h and concentrated in vacuo to give the title compound as a HCl salt (580 mg, 99%, white solid). MS(ESI⁺) m/z 526.3 (M+H)⁺.

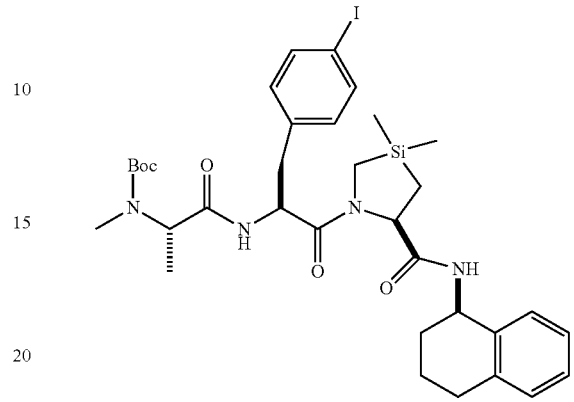

C) tert-Butyl ((S)-1-(((S)-1-(R)-3,3-dimethyl-5-((R)-1,2,3,4-tetrahydronaphthalen-1-yl)carbamoyl)-1,3-azasilolidin-1-yl)-3-(4-iodophenyl)-1-oxopropan-2-yl)amino)-1-oxopropan-2-yl)(methyl)carbamate To a solution of (S)-2-((tert-butoxycarbonyl)(methyl)amino)propanoic acid (256 mg, 1.26 mmol) in DMF (5 mL) 0° C. was added EDC (316 mg, 1.65 mmol). After 10 min, 3H-[1,2,3]-triazolo[4,5-b]pyridin-3-ol (132 mg, 0.97 mmol) was added, followed by a solution of (R)-1-((S)-2-amino-3-(4-iodophenyl)propanoyl)-3,3-dimethyl-N—(R)-1,2,3,4-tetrahydronaphthalen-1-yl)-1,3-azasilolidine-5-carboxamide, HCl (580 mg, 0.97 mmol) in DMF (3 mL) and DIEA (0.51 mL, 2.91 mmol). The reaction mixture was stirred at rt for 1.5 h and diluted with ethyl acetate and brine. The organic layer was separated, washed with brine, dried over MgSO₄ and concentrated in vacuo. The residue was purified by flash column chromatography (eluting with 30% EtOAc/DCM) to afford the title compound as a white solid (590 mg, 81%). ¹H NMR (CDCl₃) δ 7.69-7.46 (m, 2H), 7.24-7.01 (m, 4H), 6.85 (d, J=8.1 Hz, 2H), 6.51 (d, J=8.6 Hz, 1H), 5.25-5.01 (m, 3H), 3.12 (d, J=13.2 Hz, 1H), 2.94-2.72 (m, 3H), 2.68-2.60 (m, 1H), 2.50 (s, 3H), 2.11-1.97 (m, 1H), 1.91-1.72 (m, 3H), 1.59 (s, 2H), 1.47 (s, 9H), 1.36 (dd, J=14.7, 1.5 Hz, 1H), 1.21 (d, J=7.0 Hz, 3H), 1.05-0.83 (m, 1H), 0.49-0.33 (m, 3H), 0.30-0.04 (m, 3H); MS(ESI⁺) m/z 747.4 (M+H)⁺.

D) (R)-1-((S)-3-(4-(3-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)amino)-3-oxoprop-1-yn-1-yl)phenyl)-2-((S)-2-(methylamino)propanamido)propanoyl)-3,3-dimethyl-N—((R)-1,2,3,4-tetrahydronaphthalen-1-yl)-1,3-azasilolidine-5-carboxamide To a solution of tert-butyl ((S)-1-(((S)-1-((R)-3,3-dimethyl-5-(((R)-1,2,3,4-tetrahydronaphthalen-1-yl)carbamoyl)-1,3-azasilolidin-1-yl)-3-(4-iodophenyl)-1-oxopropan-2-yl)amino)-1-oxopropan-2-yl)(methyl)carbamate (85 mg, 0.11 mmol) in toluene (6 mL) were added tert-butyl ((S)-1-(((S)-3,3-dimethyl-1-oxo-1-((2S,4S)-4-propiolamido-2-((R)-1,2,3,4-tetrahydronaphthalen-1-yl)carbamoyl)pyrrolidin-1-yl)butan-2-yl)amino)-1-oxopropan-2-yl)(methyl)carbamate (74 mg, 0.12 mmol) and copper(I) iodide (6.5 mg, 0.034 mmol). The resulting suspension was purged with nitrogen for 3 min and treated with Pd(PPh₃)₄ (26 mg, 0.023 mmol) and TEA (0.13 mL, 0.91 mmol). The resulting reaction mixture was stirred at rt for 20 h and diluted with ethyl acetate and brine. The organic layer was separated, washed with saturated aq. NH₄Cl solution dried over MgSO₄ and concentrated in vacuo. The residue was purified by preparative HPLC to give the intermediate as a light yellow solid (25 mg, 18%). MS(ESI⁺) m/z 1229.0 (M+H)⁺.

To a solution of the above intermediate (20 mg, 0.016 mmol) in DCM (2 mL) was added TFA (0.4 mL, 5.19 mmol). The reaction mixture was stirred at rt for 30 min and concentrated in vacuo. The residue was purified by preparative HPLC. Fractions containing the product were combined, concentrated and lyophilized to give the title compound as a 2TFA salt (14 mg, 66%, white solid). MS(ESI⁺) m/z 1028.8 (M+H)⁺.

Example 9

A) (R)-tert-Butyl 5-(((R)-1-(2-fluorophenyl)ethyl)(4-(methoxycarbonyl)benzyl)carbamoyl)-3,3-dimethyl-1,3-azasilolidine-1-carboxylate To a solution of (R)-1-(tert-butoxycarbonyl)-3,3-dimethyl-1,3-azasilolidine-5-carboxylic acid (0.25 g, 0.96 mmol) in DCM (5 mL) were added 4-(4,6-dimethoxy[1.3.5]triazin-2-yl)-4-methylmorpholinium chloride hydrate (0.60 g, 2.2 mmol) and a solution of (R)-methyl 4-(((1-(2-fluorophenyl)ethyl)amino)methyl)benzoate (250 mg, 0.87 mmol) in DCM (2 mL) followed by DIEA (0.30 mL, 1.74 mmol). The resulting suspension was stirred at rt overnight and diluted with DCM and brine. The organic layer was separated, washed with brine, dried over MgSO₄ and concentrated in vacuo. The residue was purified by flash column chromatography (eluting with 20% EtOAc/DCM) to afford the title compound as a white solid (87 mg, 19%). MS(ESI⁺) m/z 529.3 (M+H)⁺.

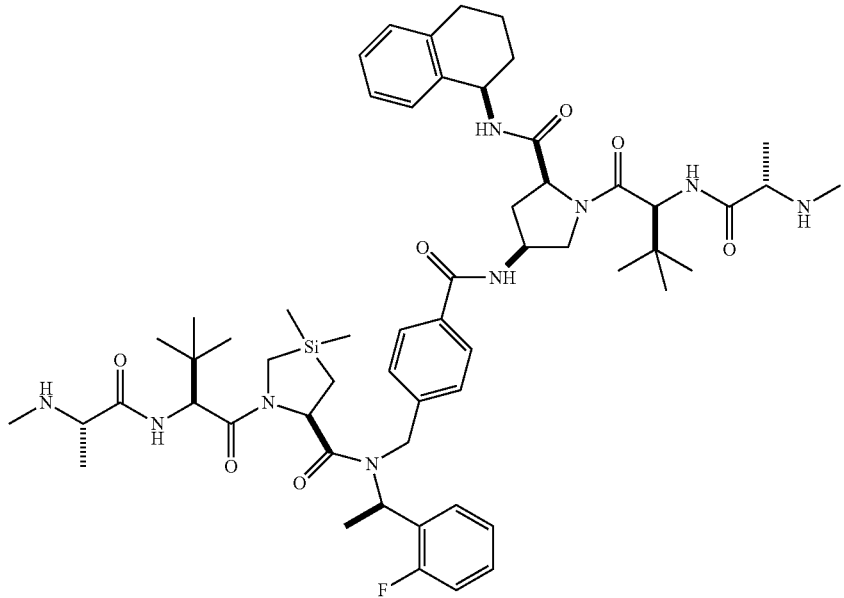

(R)-1-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N—((R)-1-(2-fluorophenyl)ethyl)-3,3-dimethyl-1,3-azasilolidine-5-carboxamide

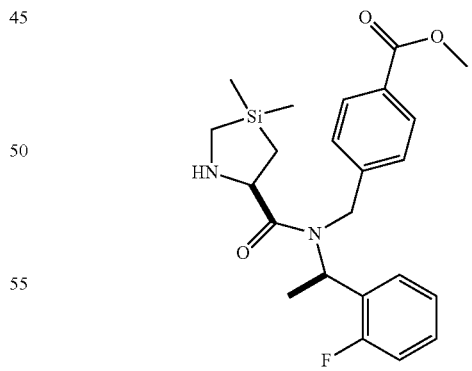

B) Methyl 4-(((R)—N—((R)-1-(2-fluorophenyl)ethyl)-3,3-dimethyl-1,3-azasilolidine-5-carboxamido)methyl)benzoate To a solution of (R)-tert-butyl 5-(((R)-1-(2-fluorophenyl)ethyl)(4-(methoxycarbonyl)benzyl)carbamoyl)-3,3-dimethyl-1,3-azasilolidine-1-carboxylate (85 mg, 0.16 mmol) in

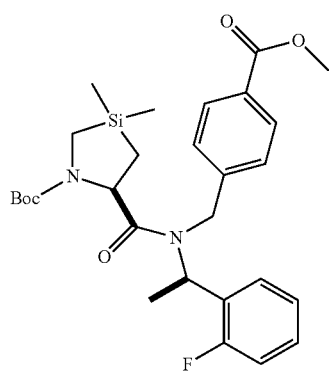 [SMILES: COC(=O)c1ccc(CN(C(=O)[C@@H]2C[Si](C)(C)CN2C(=O)OC(C)(C)C)[C@H](C)c2ccccc2F)cc1]

DCM (4 mL) was added HCl (4.0 M solution in dioxane, 1.5 mL, 6.0 mmol). The resulting reaction mixture was stirred at rt for 1 h and concentrated in vacuo to give the title compound as a HCl salt (74 mg, 99%, white solid). $^1$H NMR (DMSO-d$_6$) δ 7.92-7.74 (m, 1H), 7.68 (d, J=8.1 Hz, 1H), 7.60-7.41 (m, 1H), 7.35-7.06 (m, 3H), 7.03 (d, J=8.4 Hz, 1H), 6.96-6.75 (m, 1H), 5.71-5.43 (m, 1H), 4.85-4.41 (m, 2H), 4.37-4.12 (m, 1H), 3.88-3.77 (m, 3H), 3.73-3.48 (m, 1H), 2.70-2.54 (m, 1H), 2.34-2.13 (m, 1H), 1.73-1.56 (m, 2.5H), 1.47 (d, J=7.0 Hz, 0.5H), 1.39-1.17 (m, 1H), 1.00-0.63 (m, 1H), 0.45-0.17 (m, 6H); MS(ESI$^+$) m/z 429.8 (M+H)$^+$.

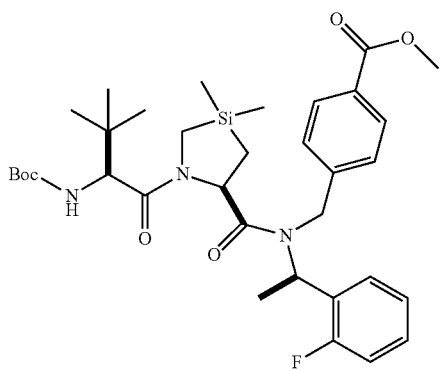 [SMILES: COC(=O)c1ccc(CN(C(=O)[C@@H]2C[Si](C)(C)CN2C(=O)[C@@H](NC(=O)OC(C)(C)C)C(C)(C)C)[C@H](C)c2ccccc2F)cc1]

C) Methyl 4-(((R)-1-((S)-2-((tert-butoxycarbonyl) amino)-3,3-dimethylbutanoyl)-N—((R)-1-(2-fluorophenyl)ethyl)-3,3-dimethyl-1,3-azasilolidine-5-carboxamido)methyl)benzoate To a solution of (S)-2-((tert-butoxycarbonyl)amino)-3,3-dimethylbutanoic acid (44 mg, 0.19 mmol) in DMF (1.5 mL) were added EDC (46 mg, 0.24 mmol) and 3H-[1,2,3]-triazolo[4,5-b]pyridin-3-ol (22 mg, 0.16 mmol). The reaction mixture was stirred at rt for 5 min and treated with a solution of methyl 4-(((R)—N—((R)-1-(2-fluorophenyl)ethyl)-3,3-dimethyl-1,3-azasilolidine-5-carboxamido)methyl)benzoate, HCl (74 mg, 0.16 mmol) in DMF (1.5 mL) followed by 4-methylmorpholine (0.05 mL, 0.48 mmol). The resulting reaction mixture was stirred at rt for 1.5 h and diluted with ethyl acetate and brine. The organic layer was separated, washed with saturated aq. NaHCO$_3$ solution, dried over MgSO$_4$ and concentrated in vacuo to give the title compound. This intermediate was used directly in the next step without purification. MS(ESI$^+$) m/z 642.6 (M+H)$^+$.

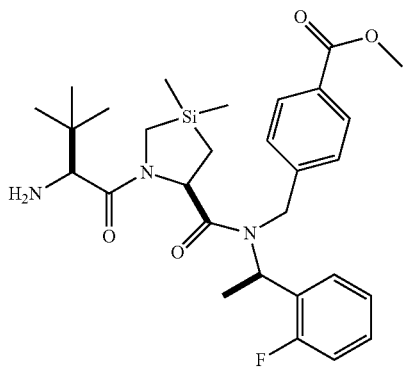 [SMILES: COC(=O)c1ccc(CN(C(=O)[C@@H]2C[Si](C)(C)CN2C(=O)[C@@H](N)C(C)(C)C)[C@H](C)c2ccccc2F)cc1]

D) Methyl 4-(((R)-1-((S)-2-amino-3,3-dimethylbutanoyl)-N—((R)-1-(2-fluorophenyl)ethyl)-3,3-dimethyl-1,3-azasilolidine-5-carboxamido)methyl)benzoate To a crude solution of methyl 4-(((R)-1-((S)-2-((tert-butoxycarbonyl)amino)-3,3-dimethylbutanoyl)-N—((R)-1-(2-fluorophenyl)ethyl)-3,3-dimethyl-1,3-azasilolidine-5-carboxamido)methyl)benzoate (100 mg, 0.16 mmol) in DCM (4 mL) was added HCl (4.0 M solution in dioxane, 1 mL). The reaction mixture was stirred at rt for 2 h and concentrated in vacuo to give the title compound as a HCl salt. MS(ESI$^+$) m/z 542.6 (M+H)$^+$.

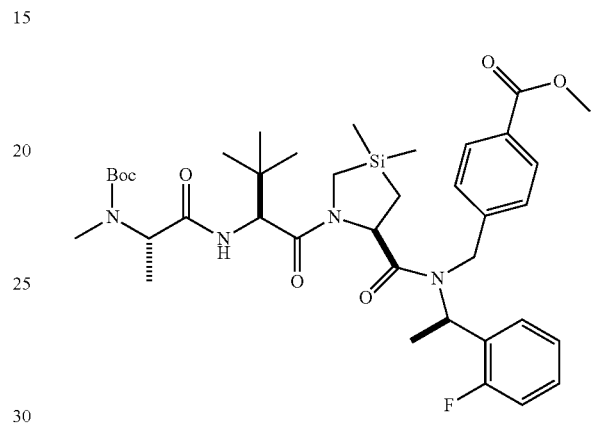

E) Methyl 4-(((R)-1-((S)-2-((S)-2-((tert-butoxycarbonyl)(methyl)amino)propanamido)-3,3-dimethylbutanoyl)-N—((R)-1-(2-fluorophenyl)ethyl)-3,3-dimethyl-1,3-azasilolidine-5-carboxamido)methyl) benzoate To a solution of (S)-2-((tert-butoxycarbonyl)(methyl)amino)propanoic acid (36 mg, 0.18 mmol) in DMF (2 mL) were added EDC (47 mg, 0.25 mmol) and 3H-[1,2,3]-triazolo[4,5-b]pyridin-3-ol (21 mg, 0.15 mmol). The reaction mixture was stirred at rt for 3 min and treated with a solution of methyl 4-(((R)-1-((S)-2-amino-3,3-dimethylbutanoyl)-N—((R)-1-(2-fluorophenyl)ethyl)-3,3-dimethyl-1,3-azasilolidine-5-carboxamido)methyl)benzoate, HCl (89 mg, 0.15 mmol) in DMF (2 mL) followed by DIEA (0.08 mL, 0.46 mmol). The resulting reaction mixture was stirred at rt for 1 h and diluted with ethyl acetate and brine. The organic layer was separated, washed successively with aq. NaHCO$_3$ solution and brine, dried over MgSO$_4$ and concentrated in vacuo. The residue was purified by flash column chromatography (eluting with 15% EtOAc/DCM) to afford the title compound as a white solid (85 mg, 76%). $^1$H NMR (CDCl$_3$) δ 8.04-7.96 (m, 2H), 7.79 (d, J=8.4 Hz, 1H), 7.40-7.10 (m, 3H), 7.08 (d, J=8.1 Hz, 1H), 7.04-6.85 (m, 1H), 5.97-5.66 (m, 1H), 5.12-4.86 (m, 1H), 4.74-4.50 (m, 1H), 4.28 (d, J=16.3 Hz, 0.5H), 3.94-3.84 (m, 3H), 3.79-3.58 (m, 0.5H), 3.31-2.97 (m, 2H), 2.78 (d, J=13.2 Hz, 3H), 1.95 (s, 2H), 1.64 (d, J=6.8 Hz, 2H), 1.53-1.44 (m, 10H), 1.37-1.22 (m, 4H), 1.09-0.86 (m, 10H), 0.38-0.09 (m, 6H); MS(ESI) m/z 727.7 (M+H)$^+$.

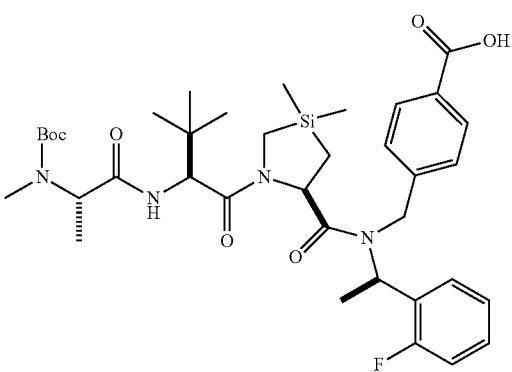 [SMILES: C[C@H](c1ccccc1F)N(Cc1ccc(C(=O)O)cc1)C(=O)[C@@H]1C[Si](C)(C)CN1C(=O)[C@@H](NC(=O)[C@H](C)N(C)C(=O)OC(C)(C)C)C(C)(C)C]

F) 4-(((R)-1-((S)-2-((S)-2-((tert-Butoxycarbonyl)
(methyl)amino)propanamido)-3,3-dimethylbu-
tanoyl)-N-(2-1-(2-fluorophenyl)ethyl)-3,3-dimethyl-
1,3-azasilolidine-5-carboxamido)methyl)benzoic
acid To a solution of methyl 4-((R)-1-((S)-2-((S)-2-((tert-bu-
toxycarbonyl)(methyl)amino)propanamido)-3,3-dimeth-
ylbutanoyl)-N—(R)-1-(2-fluorophenyl)ethyl)-3,3-dimethyl-
1,3-azasilolidine-5-carboxamido)methyl)benzoate (85 mg,
0.12 mmol) in THF (2 mL) and MeOH (1 mL) was added
LiOH (2.0 M aqueous solution, 1 mL, 3.00 mmol). The sus-
pension was stirred at rt overnight and acidified (1N HCl) to
pH 1. The resulting mixture was extracted with ethyl acetate
(twice). The organic layer was separated, dried over $MgSO_4$
and concentrated in vacuo to give the title compound as a
solid (72 mg, 86%). MS($ESI^+$) m/z 713.7 $(M+H)^+$.

G) (R)-1-((S)-3,3-Dimethyl-2-((S)-2-(methylamino)
propanamido)butanoyl)-N-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)benzyl)-N—
((R)-1-(2-fluorophenyl)ethyl)-3,3-dimethyl-1,3-
azasilolidine-5-carboxamide To a solution of 4-((R)-1-(S)-2-(S)-2-((tert-butoxycarbo-
nyl)(methyl)amino)propanamido)-3,3-dimethylbutanoyl)-
N—((R)-1-(2-fluorophenyl)ethyl)-3,3-dimethyl-1,3-aza-
silolidine-5-carboxamido)methyl)benzoic acid (70 mg, 0.10
mmol) in DMF (2 mL) were HATU (60 mg, 0.16 mmol),
tert-butyl ((S)-1-(((S)-1-((2S,4S)-4-amino-2-(((R)-1,2,3,4-
tetrahydronaphthalen-1-yl)carbamoyl)pyrrolidin-1-yl)-3,3-
dimethyl-1-oxobutan-2-yl)amino)-1-oxopropan-2-yl)(me-
thyl)carbamate (60 mg, 0.11 mmol) and DIEA (0.03 mL, 0.20
mmol). The reaction mixture was stirred at rt for 1 h and
directly purified by preparative HPLC. Fractions containing
the product were combined, and concentrated to give the
intermediate as a white solid (44 mg, 36%). MS($ESI^+$) m/z
1253.2 $(M+H)^+$.

To a solution of the above intermediate (44 mg, 0.04 mmol)
in DCM (3 mL) was added HCl (4.0 M solution in dioxane,
0.8 mL). The reaction mixture was stirred at rt for 2 h and
concentrated in vacuo. The residue was dissolved in water
and lyophilized to give the title compound as a 2TFA salt (32
mg, 76%, white solid). MS($ESI^+$) m/z 1053.9 $(M+H)^+$.

Examples 10 to 12

The following Examples were prepared using similar pro-
cedures as those described above.

| Ex. No. | Structure | Name | LCMS (M + H) |
|---|---|---|---|
| 10 | 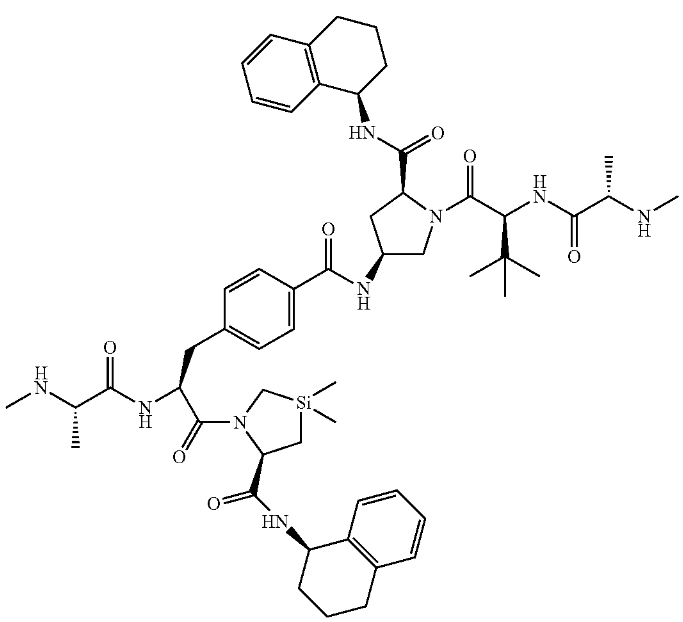 | (R)-1-((S)-3-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenyl)-2-((S)-2-(methylamino)propanamido)propanoyl)-3,3-dimethyl-N-((R)-1,2,3,4-tetrahydronaphthalen-1-yl)-1,3-azasilolidine-5-carboxamide | 1005.0 |

| Ex. No. | Structure | Name | LCMS (M + H) |
|---|---|---|---|
| 11 | 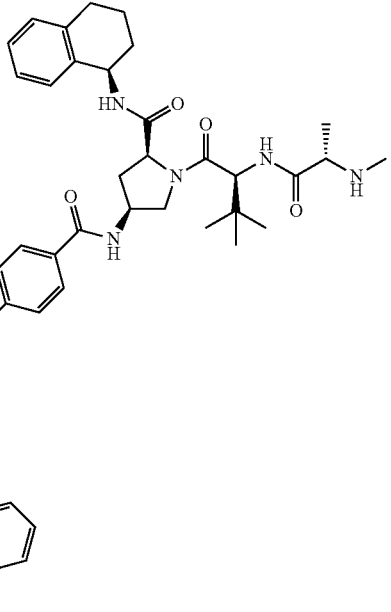 | N1-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N4-(4-((S)-3-((R)-3,3-dimethyl-5-(((R)-1,2,3,4-tetrahydronaphthalen-1-yl)carbamoyl)-1,3-azasilolidin-1-yl)-2-((S)-2-(methylamino)butanamido)-3-oxopropyl)phenyl)terephthalamide | 1138.9 |
| 12 | 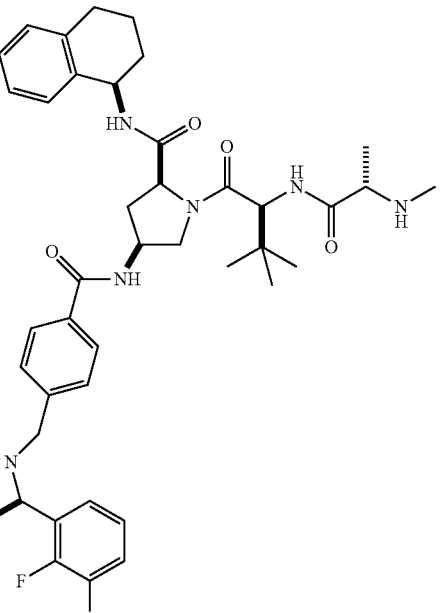 | (R)-N-((R)-1-(2,3-Difluorophenyl)ethyl)-1-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-3,3-dimethyl-1,3-azasilolidine-5-carboxamide | 1071.8 |

Evaluation of Biological Activity

Exemplary compounds were tested for inhibition of XIAP BIR3 and XIAP BIR2-3 activity. Experimental procedures and results are provided below.

A. XIAP-BIR3 SMAC Peptide Fluorescence Polarization Assay (FPA)

Assays were performed in black, flat-bottom, 384-well plates. The final assay volume was 50 μL prepared from additions of N-His-Tb-BIR3(241-356, XIAP), fluoresceinated modified SMAC peptide, and test compounds in assay buffer consisting of 20 mM sodium phosphate, 1 mM EDTA, 50 mM NaCl, and 0.05% PLURONIC® F68. The reaction was incubated at room temperature for 60 minutes and fluorescence polarization of the reaction was detected on the LJL Plate Reader. Inhibition data were calculated from mP values generated by the no protein control reactions for 100% inhibition and vehicle-only reactions for 0% inhibition. The final concentration of reagents in the assay was 130 nM N-His-Tb-BIR3(241-356, XIAP), 1.4 nM fluoresceinated modified SMAC peptide, and 1% DMSO. Dose response curves were generated to determine the concentration required for inhibiting 50% of polarization activity ($IC_{50}$). Compounds were dissolved at 10 mM in dimethylsulfoxide (DMSO) and evaluated at eleven concentrations. $IC_{50}$ values were derived by non-linear regression analysis.

B. XIAP-BIR3/SMAC Homogeneous Time Resolved Fluorescence (HTRF) Assay

Assays were performed in black, flat-bottom, 384-well plates. The final assay volume was 50 μL prepared from additions of His-BIR3 (241-356, XIAP), fluorescein labeled SMAC peptide, and test compounds in assay buffer consisting of 20 mM sodium phosphate, 1 mM EDTA, 50 mM NaCl, 50 μg/ml BSA, and 0.05% PLURONIC® F68. The reaction was incubated at room temperature for 60 minutes, following which 10 μl of mouse anti-6×His-terbium labeled Fab (Medarex, Cisbio) was added to the reaction (40 μl) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader Inhibition data were calculated from the 520/615 ratio generated by the no protein control reactions for 100% inhibition and vehicle-only reactions for 0% inhibition. The final concentration of reagents in the assay was 1 nM N-His-BIR3(241-356, XIAP), 5 nM fluorescein labeled SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

C. XIAP-BIR2/SMAC Peptide AlphaScreen Assay

Assays were performed in white, flat-bottom, 384-well ProxiPlates (Perkin Elmer). The final assay volume was 10 μL prepared from additions of His-BIR2 (124-240/C202A/C213G), Biotinylated SMAC peptide, and test compounds in assay buffer consisting of 25 mM Hepes, 100 mM NaCl, 0.1% BSA, and 5 mM $CaCl_2$. The reaction was incubated at room temperature for 60 minutes. After 60 minutes, 2.5 μL of Alphascreen detection reagent (Perkin Elmer) was added to the reaction mixture and incubated at room temperature in the dark for 120 minutes. The Alphascreen signal generated by the reaction was detected on the Envision Plate Reader Inhibition data were calculated from an Alphascreen signal generated by the no protein control reactions for 100% inhibition and vehicle-only reactions for 0% inhibition. The final concentration of reagents in the assay was 50 nM His-BIR2 (124-240/C202A/C213G), 50 nM.

Biotinylated SMAC peptide, 4 μg/mL Alphascreen detection reagents, and 0.5% DMSO. Dose response curves were generated to determine the concentration required for inhibiting 50% of the activity ($IC_{50}$). Compounds were dissolved at 10 mM in dimethylsulfoxide (DMSO) and evaluated at eleven concentrations. $IC_{50}$ values were derived by non-linear regression analysis.

D. XIAP-BIR2-3 Dimeric SMAC Peptide Homogeneous Time Resolved Fluorescence (HTRF) Assay Assays were performed in black, flat-bottom, 384-well plates. The final assay volume was 50 μL prepared from additions of His-BIR2-3 (125-356, C202A/C213G, XIAP), fluorescein labeled dimeric SMAC peptide, and test compounds in assay buffer consisting of 20 mM sodium phosphate, 1 mM EDTA, 50 mM NaCl, 50 μg/ml BSA, and 0.05% PLURONIC® F68. The reaction was incubated at room temperature for 60 minutes, following which 10 μl of mouse anti-6×His-Tb IgG (Medarex, Cisbio) was added to the reaction (40 μl) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader Inhibition data were calculated from the 520/615 ratio generated by the no protein control reactions for 100% inhibition and vehicle-only reactions for 0% inhibition. The final concentration of reagents in the assay was 0.5 nM N-His-BIR2-3(125-356, C202A/C213G, XIAP), 20 nM fluorescein labeled dimeric SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

Results

Results of the BIR2 and BIR2-3 assays are shown in the Table below.

Examples 1-11 were tested in B and D described above.

| Example No. | XIAP BIR3 $IC_{50}$ (μM) | XIAP BIR2-3 $IC_{50}$ (μM) |
|---|---|---|
| 1 | 0.012 | 0.004 |
| 2 | 0.016 | 0.006 |
| 3 | 0.014 | 0.005 |
| 4 | 0.014 | 0.004 |
| 5 | 0.103 | 0.341 |
| 6 | 0.084 | 0.205 |
| 7 | 0.093 | 0.307 |
| 8 | 0.003 | 0.004 |
| 9 | 0.052 | 0.009 |
| 10 | 0.008 | 0.005 |
| 11 | 0.030 | 0.006 |
| 12 | 0.17[#] | 0.59[*] |

([#])-XIAP BIR3 FPA ([*])-XIAP BIR2 alpha screen

What is claimed is:

1. A compound of Formula (I)

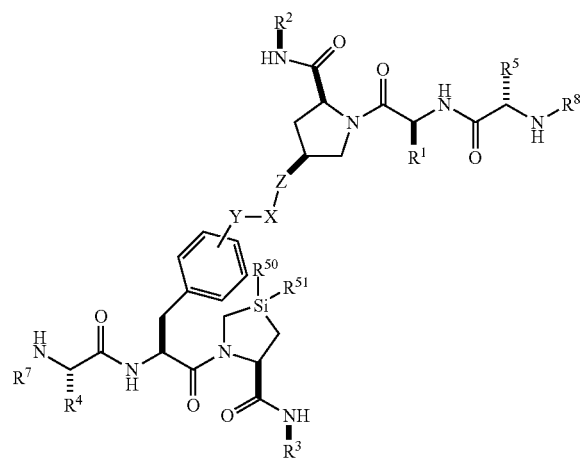

wherein:
X is —(CR$^{16}$R$^{17}$)$_m$,

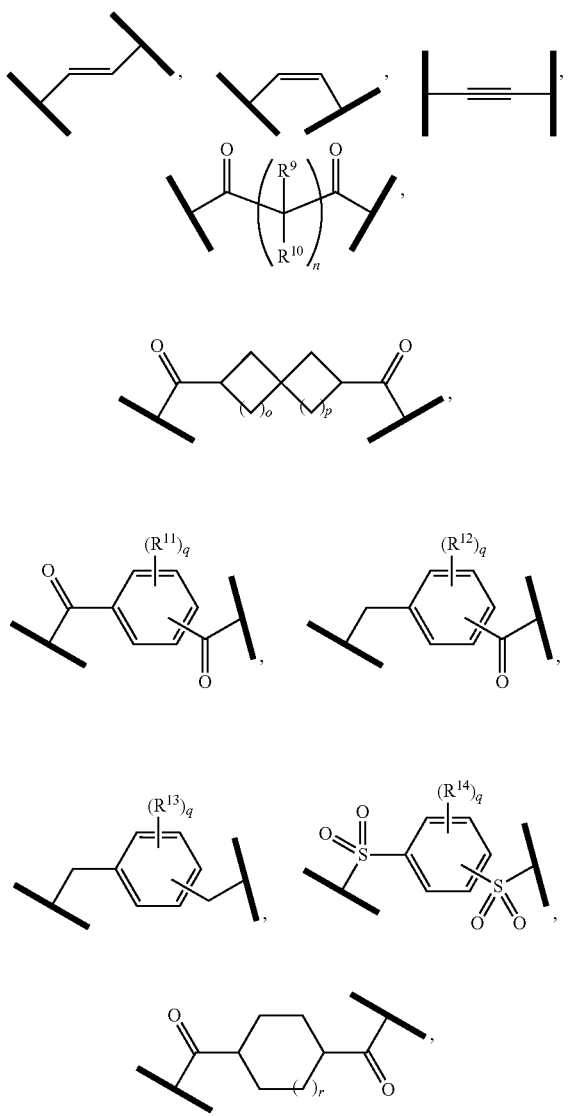

or X is absent;
Y and Z are independently —O—, C=O, NR$^6$ or are absent;
R$^1$ is optionally substituted alkyl, optionally substituted cycloalkyl, optionally substituted alkylaryl or optionally substituted aryl;
R$^2$ and R$^3$ are independently optionally substituted alkyl, optionally substituted cycloalkyl, optionally substituted cycloalkylalkyl, optionally substituted arylalkyl or optionally substituted aryl;
R$^4$ and R$^5$ are independently optionally substituted alkyl or optionally substituted cycloalkyl;
R$^6$ is hydrogen or (C$_1$-C$_3$)alkyl;
R$^7$ and R$^8$ are independently hydrogen, optionally substituted alkyl or optionally substituted cycloalkyl;
R$^9$ and R$^{10}$ are independently hydrogen, optionally substituted alkyl, or R$^9$ and R$^{10}$ may be taken together to form a ring;
R$^{11}$ to R$^{14}$ are independently hydrogen, halogen, optionally substituted alkyl or OR$^{15}$;

R$^{15}$ is hydrogen, optionally substituted alkyl or optionally substituted cycloalkyl;
R$^{16}$ and R$^{17}$ are independently hydrogen, halogen or optionally substituted alkyl;
R$^{50}$ and R$^{51}$ are independently optionally substituted alkyl, or R$^{50}$ and R$^{51}$ are taken together to form a ring;
m and n are independently an integer from 0-4;
o and p are independently an integer from 0-3;
q is an integer from 0-4; and
r is an integer from 0-1;
or a pharmaceutically acceptable salt, tautomer or stereoisomer thereof.

2. The compound according to claim 1 wherein:
X is

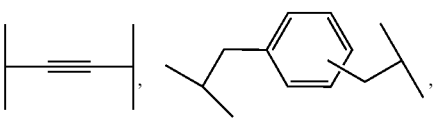

or X is absent;
R$^1$ is optionally substituted alkyl or optionally substituted alkylaryl;
R$^2$ and R$^3$ are independently optionally substituted alkyl, optionally substituted cycloalkyl, optionally substituted cycloalkylalkyl or optionally substituted arylalkyl;
R$^4$ and R$^5$ are independently optionally substituted alkyl;
R$^6$ is hydrogen or methyl;
R$^7$ and R$^8$ are independently hydrogen, optionally substituted alkyl or optionally substituted cycloalkyl;
or a pharmaceutically acceptable salt, tautomer or stereoisomer thereof.

3. The compound according to claim 2 wherein:
R$^1$ is (C$_1$-C$_6$)alkyl;
R$^2$ and R$^3$ are independently alkyl, cycloalkyl, cycloalkylalkyl or phenylalkyl, wherein the phenyl group is substituted with one or more alkyl or halogen groups;
R$^4$ and R$^5$ are independently (C$_1$-C$_3$)alkyl;
R$^7$ and R$^8$ are independently (C$_1$-C$_3$)alkyl;
or a pharmaceutically acceptable salt, tautomer or stereoisomer thereof.

4. The compound according to claim 3 wherein:
R$^1$ is t-butyl;
R$^2$ is 1,2,3,4-tetrahydronaphthalenyl;
R$^3$ is alkyl, cycloalkyl, cycloalkylalkyl or phenylalkyl, wherein the phenyl group is substituted with one or more fluoro groups;
R$^4$ and R$^5$ are independently methyl or ethyl;
R$^7$ and R$^8$ are independently methyl or ethyl;
R$^6$ is hydrogen;
R$^{50}$ and R$^{51}$ are independently methyl, ethyl or propyl;
or a pharmaceutically acceptable salt, tautomer or stereoisomer thereof.

5. A compound of Formula (II)

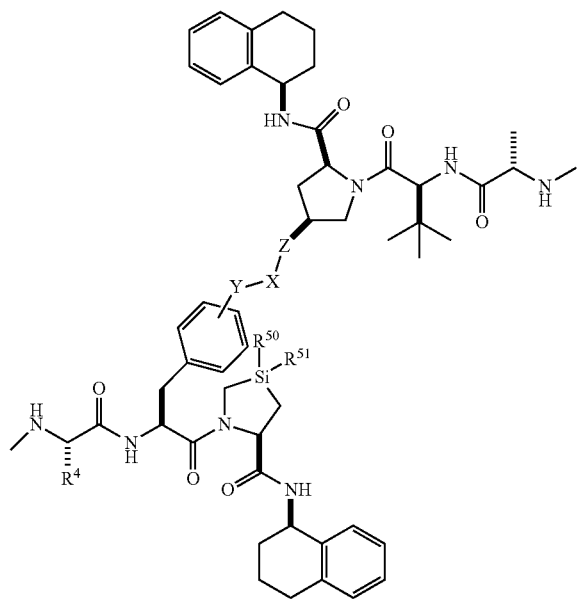

(II)

wherein:
X is —(CR$^{16}$R$^{17}$)$_m$,

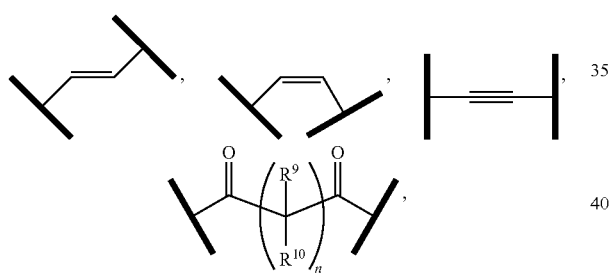

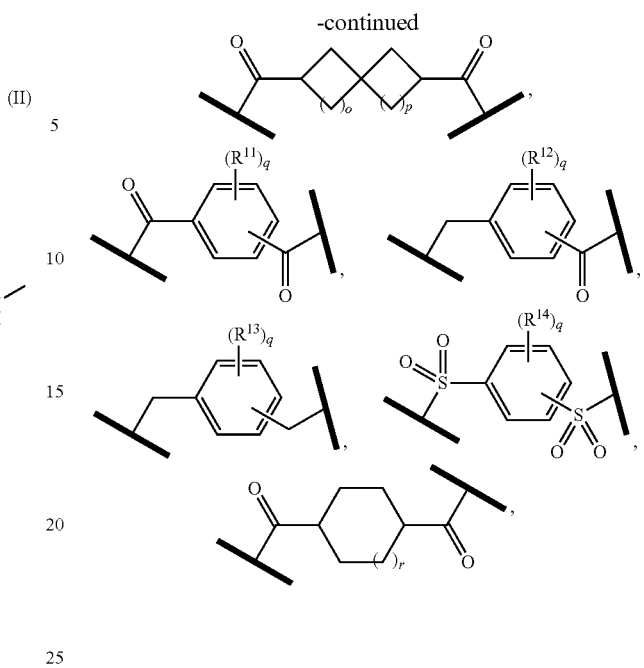

or X is absent;

Y and Z are independently —O—, C=O, NR$^6$ or are absent;

R$^4$ is optionally substituted alkyl or optionally substituted cycloalkyl;

R$^6$ is hydrogen or (C$_1$-C$_3$)alkyl;

R$^{50}$ and R$^{51}$ are independently methyl, ethyl or propyl;

or a pharmaceutically acceptable salt, tautomer or stereoisomer thereof.

6. A pharmaceutical composition comprising a compound of claim 1 and a pharmaceutically acceptable carrier.

7. A pharmaceutical composition comprising a compound of claim 5 and a pharmaceutically acceptable carrier.

* * * * *